US012583846B2

(12) United States Patent
Yang et al.

(10) Patent No.: US 12,583,846 B2
(45) Date of Patent: Mar. 24, 2026

(54) 2H-BENZOPYRAN DERIVATIVES AS CRAC INHIBITORS

(71) Applicant: CISEN PHARMACEUTICAL CO., LTD, Jining (CN)

(72) Inventors: Yaxun Yang, Shanghai (CN); Zhigan Jiang, Shanghai (CN); Jianhua Xia, Shanghai (CN); Wei Wei, Shanghai (CN); Haiying He, Shanghai (CN); Shuhui Chen, Shanghai (CN)

(73) Assignee: CISEN PHARMACEUTICAL CO., LTD

( * ) Notice: Subject to any disclaimer, the term of this patent is extended or adjusted under 35 U.S.C. 154(b) by 1010 days.

(21) Appl. No.: 17/763,438

(22) PCT Filed: Sep. 25, 2020

(86) PCT No.: PCT/CN2020/117670

§ 371 (c)(1),
(2) Date: Mar. 24, 2022

(87) PCT Pub. No.: WO2021/057890

PCT Pub. Date: Apr. 1, 2021

(65) Prior Publication Data

US 2022/0380356 A1 Dec. 1, 2022

(30) Foreign Application Priority Data

| | | |
|---|---|---|
| Sep. 25, 2019 | (CN) | 201910915379.1 |
| Sep. 30, 2019 | (CN) | 201910942170.4 |
| Oct. 18, 2019 | (CN) | 201910995175.3 |
| Apr. 2, 2020 | (CN) | 202010255852.0 |
| Apr. 28, 2020 | (CN) | 202010350260.7 |
| Jun. 11, 2020 | (CN) | 202010528780.2 |
| Jul. 7, 2020 | (CN) | 202010647083.9 |
| Aug. 28, 2020 | (CN) | 202010885601.0 |

(51) Int. Cl.

| | |
|---|---|
| ***C07D 413/04*** | (2006.01) |
| ***C07D 401/04*** | (2006.01) |
| ***C07D 405/04*** | (2006.01) |
| ***C07D 413/14*** | (2006.01) |
| ***C07D 417/14*** | (2006.01) |
| ***C07F 9/141*** | (2006.01) |

(52) U.S. Cl.

CPC ......... *C07D 413/04* (2013.01); *C07D 401/04* (2013.01); *C07D 405/04* (2013.01); *C07D 413/14* (2013.01); *C07D 417/14* (2013.01); *C07F 9/141* (2013.01)

(58) Field of Classification Search

CPC .................... C07D 413/04
USPC .................... 514/76
See application file for complete search history.

(56) References Cited

U.S. PATENT DOCUMENTS

| | | | | |
|---|---|---|---|---|
| 2011/0263612 | A1 | 10/2011 | Whitten et al. | |
| 2014/0256771 | A1 | 9/2014 | Cao et al. | |
| 2015/0322012 | A1* | 11/2015 | Whitten | C07D 409/04 546/281.1 |

FOREIGN PATENT DOCUMENTS

| | | | | |
|---|---|---|---|---|
| CN | 101083985 | A | 12/2007 | |
| CN | 101163478 | A | 4/2008 | |
| CN | 107530333 | A | 1/2018 | |
| JP | 2008513508 | A | 5/2008 | |
| JP | 2008528520 | A | 7/2008 | |
| JP | 2013525433 | A | 6/2013 | |
| JP | 2018506553 | A | 3/2018 | |
| JP | 2018529650 | A | 10/2018 | |
| WO | 2006034402 | A2 | 3/2006 | |
| WO | 2006081391 | A2 | 8/2006 | |
| WO | 2011139489 | A2 | 11/2011 | |
| WO | 2014207648 | A1 | 12/2014 | |
| WO | 2016138472 | A1 | 9/2016 | |
| WO | 2017027400 | A1 | 2/2017 | |
| WO | 2018140796 | A1 | 8/2018 | |
| WO | WO-2019126253 | A1 * | 6/2019 | A61K 31/454 |

OTHER PUBLICATIONS

Written Opinion of International Searching Authority in related Application No. PCT/CN2020/117670, dated Dec. 21, 2020, 6 pages.
International Searching Report in related Application No. PCT/CN2020/117670, dated Dec. 21, 2020, 10 pages.
Chinese Second Office Action issued in Chinese Patent Application No. CN202080056888.4, Aug. 26, 2023, 6 pages.
European Supplementary Search Report issued in European Patent Application No. EP20867063.8, Sep. 25, 2023, 9 pages.
Notice of Reasons for Refusal issued in Japanese Patent Application No. 2022-519088, Oct. 31, 2023, 6 pages.
First Chinese Office Action issued in related Chinese Patent Application No. CN202080056888.4, Mar. 31, 2023, 7 pages.
Chinese Search Report issued in related Chinese Patent Application No. CN202080056888.4, Mar. 28, 2023, 4 pages.
Notice of Reasons for Refusal issued in related Japanese Patent Application No. 2022-519088, May 30, 2023, 6 pages.

* cited by examiner

*Primary Examiner* — Jeffrey H Murray
*Assistant Examiner* — Rilla Marie Samsell
(74) *Attorney, Agent, or Firm* — Dilworth IP, LLC

(57) ABSTRACT

A class of compounds that have a pyrazine structure, specifically disclosed is a compound represented by formula, isomers or pharmaceutically acceptable salts thereof, and an application thereof in the preparation of CRAC inhibitors.

16 Claims, 2 Drawing Sheets

2H-BENZOPYRAN DERIVATIVES AS CRAC INHIBITORS

The present application claims the following priorities:
CN201910915379.1, filed on Sep. 25, 2019;
CN201910942170.4, filed on Sep. 30, 2019;
CN201910995175.3, filed on Oct. 18, 2019;
CN202010255852.0, filed on Apr. 2, 2020;
CN202010350260.7, filed on Apr. 28, 2020;
CN202010528780.2, filed on Jun. 11, 2020;
CN202010647083.9, filed on Jul. 7. 2020;
CN202010885601.0, filed on Aug. 28. 2020.

TECHNICAL FIELD

The present disclosure relates to a class of compounds having a 2H-benzopyran structure, and specifically discloses a compound represented by formula (VII), an isomer thereof or a pharmaceutically acceptable salt thereof, and a use thereof in the manufacture of a medicament related to CRAC inhibitors.

BACKGROUND

Acetylcholine receptors (AchR) and cholecystokinin receptors (CCKR) are present on the plasma membrane of pancreatic acinar cells, both of which are dependent on $Ca^{2+}$ channels. Under the action of acetylcholine, acetylcholine receptor activates phospholipase (PLC) to generate inositol 1,4,5-triphosphate ($IP_3$). Under the action of cholecystokinin, the cholecystokinin receptor binds to adenosine diphosphate-ribosyl cyclase (ADP-ribosyl cyclase) via an unknown pathway to generate nicotinic acid adenine dinucleotide phosphate (NAADP) and cyclic adenosine diphosphate ribose (CADPR). $IP_3$ and ryanodine receptors on the endoplasmic reticulum, activated by $IP_3$ and NAADP/CADPR, respectively, release stored $Ca^{2+}$ from the endoplasmic reticulum into the cytoplasm. As intracellular $Ca^{2+}$ is depleted, the depletion of $Ca^{2+}$ pool causes the $Ca^{2+}$ receptor STIM1 protein located in endoplasmic reticulum to oligomerize and moves to the nearest endoplasmic reticulum-cell membrane junction; Orail channel located in plasma membrane opens and allows $Ca^{2+}$ influx, leading to excessive intracellular $Ca^{2+}$ and premature activation of proenzyme, inducing the production of intracellular inflammatory factors.

Alcohol and stones and other factors may induce the release of $Ca^{2+}$ from endoplasmic reticulum, and the decrease of endoplasmic reticulum $Ca^{2+}$ storage stimulates the hyperactivation of cellular CRAC channel (specifically Orai channel), leading to a large amount of $Ca^{2+}$ influx. The significant increase of intracellular calcium concentration in pancreatic acinar cells can cause the premature activation of zymogen particles to pancreatic protein, and the pancreatic protein in turn activates other pancreatic digestive enzymes and finally results in the digestion and necrosis of pancreas. CRAC inhibitors can inhibit the influx of $Ca^{2+}$ and thus prevent the necrosis of pancreas. CRAC inhibitors can inhibit the release of $Ca^{2+}$ and thus prevent necrosis of the pancreas.

In developed countries, obstruction of the common bile duct by stones and alcohol use is the most common cause of acute pancreatitis, accounting for 70-80% of cases. Cholelithiasis-induced pancreatitis is caused by duct obstruction and the action of bile acids on pancreatic acinar cells. Gallstones allow bile to flow back into the pancreatic ductal system, and once in the pancreatic acinar cells, bile acids activate calcium into these cells via CRAC channels, causing acute pancreatitis and pancreatic exocrine cell necrosis through unregulated digestive enzyme activation, cytokine production and infiltration of the pancreas by inflammatory cells. Alcohol use is the second most common cause of acute pancreatitis, but the correlation between alcohol and pancreatitis remains not fully understood. Although alcohol use is commonly associated with acute and chronic pancreatitis, alcohol itself does not cause pancreatitis. In contrast, it appears that metabolic by-products of alcohol may be the cause of disease in some patients. Researchers have shown that specific ethanol metabolites, called fatty acid ethyl esters (FAEEs), may induce a sustained release of intracellular calcium within calcium ion cells to activate CRAC channels, resulting in high intracellular calcium levels inducing disease in the same way as gallstones.

CONTENT OF THE PRESENT INVENTION

The present disclosure provides a compound represented by formula (VII), an isomer thereof or a pharmaceutically acceptable salt thereof, (VII)

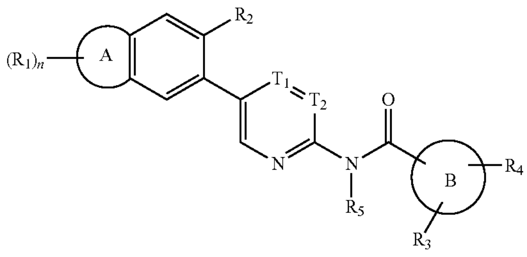

wherein, each of $T_1$ and $T_2$ is independently selected from CH and N;

each of $R_1$ is independently selected from H, $C_{3-10}$ cycloalkyl and 3- to 10-membered heterocycloalkyl, and each of the $C_{3-10}$ cycloalkyl and 3- to 10-membered heterocycloalkyl is independently optionally substituted with 1, 2, or 3 $R_a$;

$R_2$ is selected from H, F, Cl, Br, I and $C_{1-3}$ alkyl, and the $C_{1-3}$ alkyl is optionally substituted with 1, 2, or 3 $R_b$;

$R_3$ is selected from H, F, Cl, Br, I, CN and $C_{1-3}$ alkyl, and the $C_{1-3}$ alkyl is optionally substituted with 1, 2, or 3 $R_c$;

$R_4$ is selected from H, F, Cl, Br, I, CN and $C_{1-3}$ alkyl, and the $C_{1-3}$ alkyl is optionally substituted with 1, 2, or 3 $R_d$;

$R_5$ is selected from H,

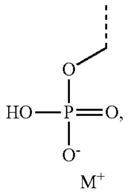
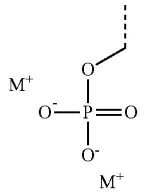
and
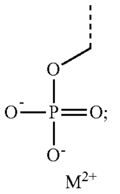

each of $M^+$ is independently selected from $Na^+$, $NH_4^+$, $K^+$, choline,

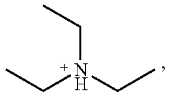, 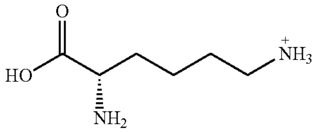 and

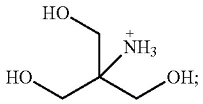;

each of $M^{2+}$ is independently selected from $Ca^{2+}$, $MG^{2+}$, $Zn^{2+}$ and

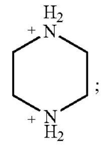;

ring A is selected from 5- to 6-membered heteroaryl, and $R_1$ is not H when ring A is 5-membered heteroaryl;

ring B is selected from $C_{6-12}$ aryl, 5- to 10-membered heteroaryl, $C_{3-10}$ cycloalkyl and 3- to 10-membered heterocycloalkyl;

n is selected from 1 and 2;

each of $R_a$, $R_b$, $R_c$ and $R_d$ is independently selected from F, Cl, Br, I, OH, $NH_2$ and $C_{1-3}$ alkyl, and the $C_{1-3}$ alkyl is optionally substituted with 1, 2, or 3 R;

each of R is independently selected from F, Cl, Br and I;

each of the 5- to 10-membered heteroaryl, 5- to 6-membered heteroaryl and 3- to 10-membered heterocycloalkyl independently contains 1, 2, or 3 heteroatoms or heteroatom groups independently selected from —O—, —NH—, —S— and N.

In some embodiments of the present disclosure, each of $R_a$, $R_b$, $R_c$ and $R_d$ is independently selected from F, Cl, Br, I, $CH_3$, $CF_3$, $CHF_2$, $CH_2F$, $CH_2CH_3$, $CH_2CF_3$, $CH_2CH_2CH_3$,

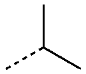 and 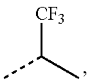, and the other variables are defined herein.

In some embodiments of the present disclosure, the $R_1$ is selected from H, F, Cl, Br, I, $C_{3-6}$ cycloalkyl and 4- to 6-membered heterocycloalkyl, and each of the $C_{3-6}$ cycloalkyl and 4- to 6-membered heterocycloalkyl is independently optionally substituted with 1, 2, or 3 $R_a$; and the other variables are defined herein.

In some embodiments of the present disclosure, the $R_1$ is selected from H, F, Cl, Br, I, cyclopropyl and oxetanyl, and each of the cyclopropyl and oxetanyl is independently optionally substituted with 1, 2, or 3 $R_a$, and the other variables are defined herein.

In some embodiments of the present disclosure, the $R_1$ is selected from H, F, Cl, Br, I,

 and 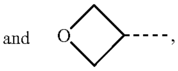, and each of the

 and 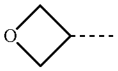

is independently optionally substituted with 1, 2, or 3 $R_a$, and the other variables are defined herein.

In some embodiments of the present disclosure, the $R_1$ is selected from H,

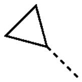 and 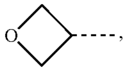, and the other variables are defined herein.

In some embodiments of the present disclosure, the $R_2$ is selected from H, F, Cl, Br, I, $CH_3$, $CF_3$, $CHF_2$, $CH_2F$, $CH_2CH_3$, $CH_2CF_3$, $CH_2CH_2CH_3$,

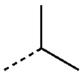 and 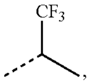, and the other variables are defined herein.

In some embodiments of the present disclosure, the $R_2$ is selected from Cl, and the other variables are defined herein.

In some embodiments of the present disclosure, the $R_3$ is selected from H, F, Cl, Br, I, CN, $CH_3$, $CF_3$, $CH_2F$, $CH_2CH_3$, $CH_2CF_3$, $CH_2CH_2CH_3$,

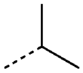 and 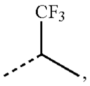, and the other variables are defined herein.

In some embodiments of the present disclosure, the $R_3$ is selected from H, F, $CH_3$ and CN, and the other variables are defined herein.

In some embodiments of the present disclosure, the $R_4$ is selected from H, F, Cl, Br, I, CN, $CH_3$, $CF_3$, $CHF_2$, $CH_2F$, $CH_2CH_3$, $CH_2CF_3$, $CH_2CH_2CH_3$,

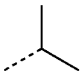 and 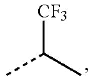, and the other variables are defined herein.

In some embodiments of the present disclosure, the $R_4$ is selected from H, F, $CH_3$ and CN, and the other variables are defined herein.

In some embodiments of the present disclosure, the $R_5$ is selected front H,

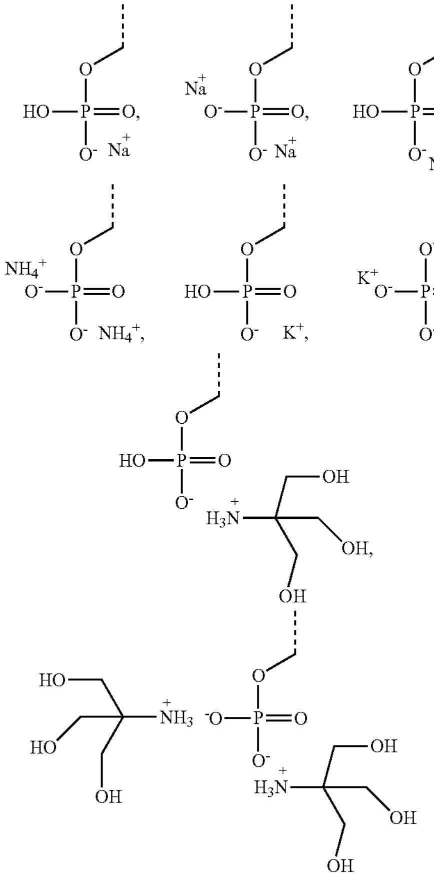

and

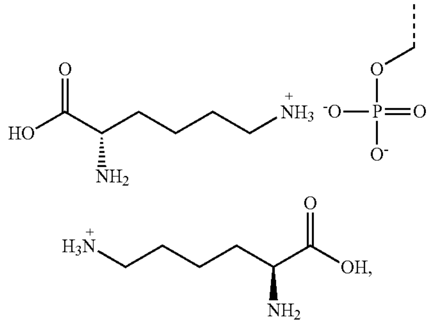

and the other variables are defined herein.

In some embodiments of the present disclosure, the ring A is selected from oxazolyl, isoxazolyl, furanyl, pyridinyl and 1,2,3-triazolyl, and the other variables are defined herein.

In some embodiments of the present disclosure, the structural unit

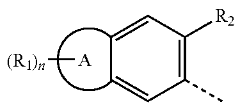

is selected from

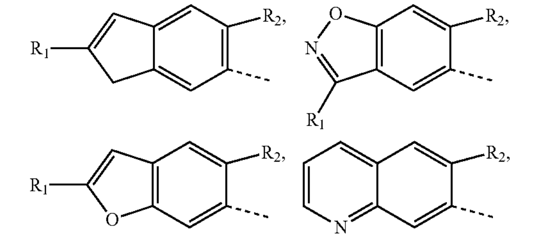

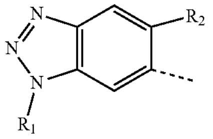

and

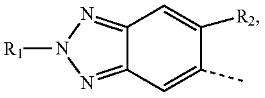

and the other variables are defined herein.

In some embodiments of the present disclosure, the structural unit

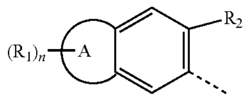

is selected from

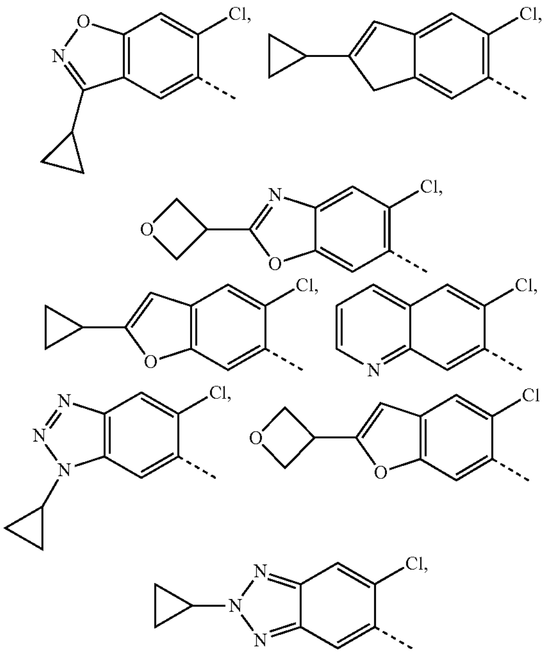

and the other variables are defined herein.

in some embodiments of the present disclosure, the ling B is selected from $C_{6-10}$ aryl, 5- to 6-membered heteroaryl, $C_{3-6}$ cycloalkyl and 4- to 6-membered heterocycloalkyl, and the other variables are defined herein.

in some embodiments of the present disclosure, the ring B is selected from phenyl,

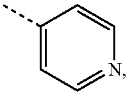
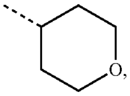
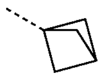
and
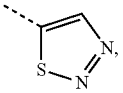

and the other variables are defined herein.

In some embodiments of the present disclosure, the structural unit

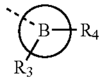

is selected from

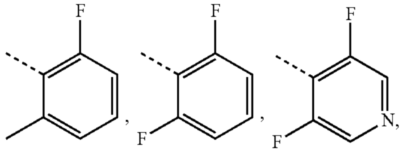
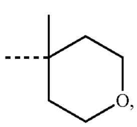
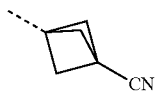
and
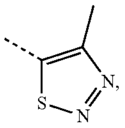

and the other variables are defined herein.

The present disclosure provides a compound represented by formula (I), an isomer thereof or a pharmaceutically acceptable salt thereof,

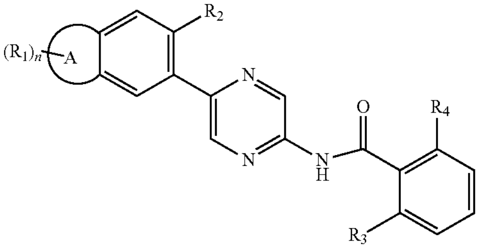
(I)

wherein, each of $R_1$ is independently selected from H, F, Cl, Br, F $C_{3-10}$ cycloalkyl and 3- to 10-membered heterocycloalkyl, and each of the $C_{3-10}$ cycloalkyl and 3- to 10-membered heterocycloalkyl is independently optionally substituted with 1, 2, or 3 $R_a$;

$R_2$is selected from H, F, Cl, Br, I and $C_{1-3}$ alkyl, and the $C_{1-3}$ alkyl is optionally substituted with 1, 2, or 3 $R_b$;

$R_3$ is selected from H, F, Cl, Br, I and $C_{1-3}$ alkyl, and the $C_{1-3}$ alkyl is optionally substituted with 1, 2, or 3 $R_c$;

$R_4$ is selected from H, F, Cl, Br, I and $C_{1-3}$ alkyl, and the $C_{1-3}$ alkyl is optionally substituted with 1, 2, or 3 $R_d$;

ring A is selected from 5- to 6-membered heteroaryl, n is selected from 1 and 2;

each of $R_a$, $R_b$, $R_c$ and $R_d$ is independently selected from F, Cl, Br, I, OH, $NH_2$ and $C_{1-3}$ alkyl, and the $C_{1-3}$ alkyl is optionally substituted with 1, 2, or 3 R;

R is independently selected from F, Cl, Br and I;

each of the 5- to 6-membered heteroaryl and 3- to 10-membered heterocycloalkyl independently contains 1, 2, or 3 heteroatoms or heteroatom groups independently selected from —O—, —NH—, —S— and N.

The present disclosure also provides a compound represented by formula (II), an isomer thereof or a pharmaceutically acceptable salt thereof, (II)

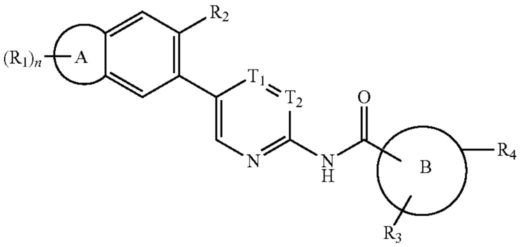

wherein, each of $T_1$ and $T_2$ is independently selected from CH and N;

each of $R_1$ is independently selected from H, $C_{3-10}$ cycloalkyl and 3- to 10-membered heterocycloalkyl, and each of the $C_{3-10}$ cycloalkyl and 3- to 10-membered heterocycloalkyl is independently optionally substituted with 1, 2, or 3 $R_a$;

$R_2$ is selected from H, F, Cl, Br, I and $C_{1-3}$ alkyl, and the $C_{1-3}$ alkyl is optionally substituted with 1, 2, or 3 $R_b$;

$R_3$ is selected from H, F, Cl, Br, I, CN and $C_{1-3}$ alkyl, and the $C_{1-3}$ alkyl is optionally substituted with 1, 2, or 3 $R_c$;

$R_4$ is selected from H, F, Cl, Br, I, CN and $C_{1-3}$ alkyl, and the $C_{1-3}$ alkyl is optionally substituted with 1, 2, or 3 $R_d$;

ring A is selected from 5- to 6-membered heteroaryl, and $R_1$ is not H when ring A is 5-membered heteroaryl;

ring B is selected from $C_{6-12}$ aryl, $C_{3-10}$ cycloalkyl and 3- to 10-membered heterocycloalkyl;

n is selected from 1 and 2;

each of $R_a$, $R_b$, $R_c$ and $R_d$ is independently selected from F, Cl, Br, I, OH, $NH_2$ and $C_{1-3}$ alkyl, and the $C_{1-3}$ alkyl is optionally substituted with 1, 2, or 3 R;

each of R is independently selected from F, Cl, Br and I;

each of the 5- to 6-membered heteroaryl and 3- to 10-membered heterocycloalkyl. independently contains 1, 2, or 3 heteroatoms or heteroatom groups independently selected from —O—, —NH—, —S— and N.

The present disclosure also provides a compound represented by formula (II), an isomer thereof or a pharmaceutically acceptable salt thereof, (II)

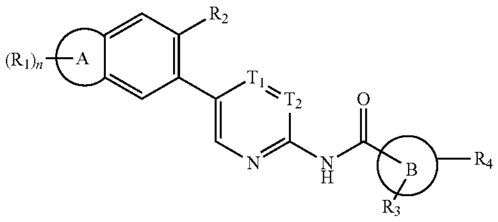

wherein, each of $T_1$ and $T_2$ is independently selected from CH and N;

each of $R_1$ is independently selected from H, $C_{3-10}$ cycloalkyl and 3- to 10-membered heterocycloalkyl, and each of the $C_{3-10}$ cycloalkyl and 3- to 10-membered heterocycloalkyl is independently optionally substituted with 1, 2, or 3 $R_a$;

$R_2$ is selected from H, F, Cl, Br, I and $C_{1-3}$ alkyl, and the $C_{1-3}$ alkyl is optionally substituted with 1, 2, or 3 $R_b$;

$R_3$ is selected from H, F, Cl, Br, I, CN and $C_{1-3}$ alkyl, and the $C_{1-3}$ alkyl is optionally substituted with 1, 2, or 3 $R_c$;

$R_4$ is selected from H, F, Cl, Br, I, CN and $C_{1-3}$ alkyl, and the $C_{1-3}$ alkyl is optionally substituted with 1, 2, or 3 $R_d$;

ring A is selected from 5- to 6-membered heteroaryl, and $R_1$ is not H when ring A is 5-membered heteroaryl;

ring B is selected from $C_{6-12}$ aryl; 5- to 10-membered heteroaryl, $C_{3-10}$ cycloalkyl and 3- to 10-membered heterocycloalkyl;

n is selected from 1 and 2;

each of $R_a$, $R_b$, $R_c$ and $R_d$ is independently selected from F, Cl, Br, I, OH, $NH_2$ and $C_{1-3}$ alkyl, and the $C_{1-3}$ alkyl is optionally substituted with 1, 2, or 3 R;

each of R is independently selected from F, Cl, Br and I;

each of the 5- to 10-membered heteroaryl, 5- to 6-membered heteroaryl and 3- to 10-membered heterocycloalkyl independently contains 1, 2, or 3 heteroatoms or heteroatom groups independently selected from —O—, —NH—, —S— and N.

The present disclosure provides a compound represented by formula (VII), an isomer thereof or a pharmaceutically acceptable salt thereof, (VII)

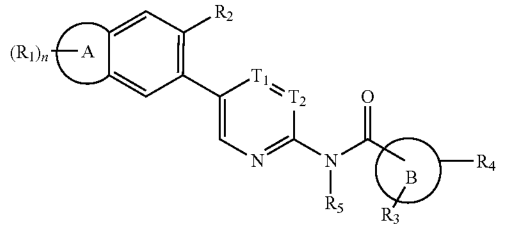

wherein, each of $T_1$ and $T_2$ is independently selected from CH and each of $R_1$ is independently selected from H, $C_{3-10}$ cycloalkyl and 3- to 10-membered heterocycloalkyl, and each of the $C_{3-10}$ cycloalkyl and 3- to 10-membered heterocycloalkyl is independently optionally substituted with 1, 2, or 3 $R_a$;

$R_2$ is selected from H, F, Cl, Br, I and $C_{1-3}$ alkyl, and the $C_{1-3}$ alkyl is optionally substituted with 1, 2, or 3 $R_b$;

$R_3$ is selected from H, F, Cl, Br, I, CN and $C_{1-3}$ alkyl, and the $C_{1-3}$ alkyl is optionally substituted with 1, 2, or 3 $R_c$;

$R_4$ is selected from H, F, Cl, Br, I, CN and $C_{1-3}$ alkyl, and the $C_{1-3}$ alkyl is optionally substituted with 1, 2, or 3 $R_d$;

$R_5$ is selected from H and

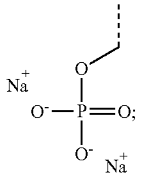

ring A is selected from 5- to 6-membered heteroaryl, and $R_1$ is not H when ring A is 5-membered heteroaryl;

ring B is selected from $C_{6-12}$ aryl, 5- to 10-membered heteroaryl, $C_{3-10}$ cycloalkyl and 3- to 10-membered heterocycloalkyl;

n is selected from 1 and 2;

each of $R_a$, $R_b$, $R_c$ and $R_d$ is independently selected from F, Cl, Br, I, OH, $NH_2$ and $C_{1-3}$ alkyl, and the $C_{1-3}$ alkyl is optionally substituted with 1, 2, or 3 R;

each of R is independently selected from F, Cl, Br and I;

each of the 5- to 10-membered heteroaryl, 5- to 6-membered heteroaryl and c heterocycloalkyl independently contains 1, 2, or 3 heteroatoms or heteroatom groups independently selected from —O—, —NH—, —S— and N.

The present disclosure provides a compound represented by formula (VII), an isomer thereof or a pharmaceutically acceptable salt thereof, (VII)

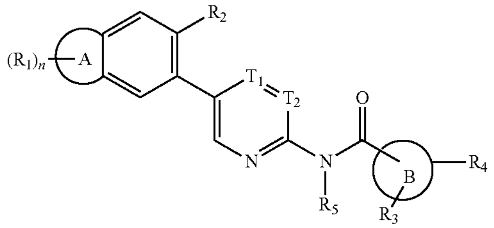

wherein, each of $T_1$ and $T_2$ is independently selected from CH and N;

each of $R_1$ is independently selected from H, $C_{3-10}$ cycloalkyl and 3- to 10-membered heterocycloalkyl, and each of the $C_{3-10}$ cycloalkyl and 3- to 10-membered heterocycloalkyl is independently optionally substituted with 1, 2, or 3 $R_a$;

$R_2$ is selected from H, F, Cl, Br, I and $C_{1-3}$ alkyl, and the $C_{1-3}$ alkyl is optionally substituted with 1, 2, or 3 $R_b$;

$R_3$ is selected from H, F, Cl, Br, I, CN and $C_{1-3}$ alkyl, and the $C_{1-3}$ alkyl is optionally substituted with 1, 2, or 3 $R_c$;

$R_4$ is selected from H, F, Cl, Br, I, CN and $C_{1-3}$ alkyl, and the $C_{1-3}$ alkyl is optionally substituted with 1, 2, or 3 $R_d$;

$R_5$ is selected from H,

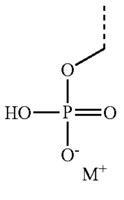

and

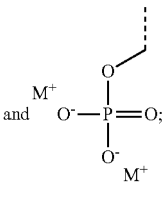

each of $M^+$ is independently selected from $Na^+$, $NH_4^+$ and $K^+$;

ring A is selected from 5- to 6-membered heteroaryl, and $R_1$ is not H when ring A is 5-membered heteroaryl;

ring B is selected from $C_{6-12}$ aryl, 5- to 10-membered heteroaryl; $C_{3-10}$ cycloalkyl and 3- to 10-membered heterocycloalkyl;

n is selected from 1 and 2;

each of $R_a$, $R_b$, $R_c$ and $R_d$ is independently selected from F, Cl, Br, OH, $NH_2$ and $C_{1-3}$ alkyl, and the $C_{1-3}$ alkyl is optionally substituted with 1, 2, or 3 R;

each of R is independently selected from F, Cl, Br and I;

each of the 5- to 10-membered heteroaryl, 5- to 6-membered .heteroaryl and 3- to 10-membered heterocycloalkyl independently contains 1, 2, or 3 heteroatoms or heteroatom groups independently selected from —O—, —NH—, —S— and N.

The present disclosure provides a compound represented by formula (VII), an isomer thereof or a pharmaceutically acceptable salt thereof, (VII)

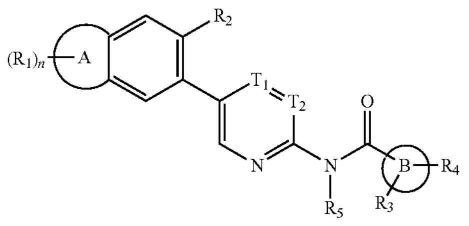

wherein;

each of $T_1$ and $T_2$ is independently selected from CH and N;

each of $R_1$ is independently selected from H, $C_{3-10}$ cycloalkyl and 3- to 10-membered heterocycloalkyl, and each of the $C_{3-10}$ cycloalkyl and 3- to 10-membered heterocycloalkyl is independently optionally substituted with 1, 2, or 3 $R_a$;

$R_2$ is selected from H, F, Cl, Br, I and $C_{1-3}$ alkyl, and the $C_{1-3}$ alkyl is optionally substituted with 1, 2, or 3 $R_b$;

$R_3$ is selected from H, F, Cl, Br, I, CN and $C_{1-3}$ alkyl, and the $C_{1-3}$ alkyl is optionally substituted with 1, 2, or 3 $R_c$;

$R_4$ is selected from H, F, Cl, Br, I. CN and $C_{1-3}$ alkyl, and the $C_{1-3}$ alkyl is optionally substituted with 1, 2, or 3 $R_d$;

$R_5$ is selected from H,

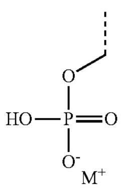

and

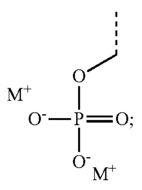

each of $M^+$ is independently selected from $Na^+$, $NH_4^+$, $K^+$ and

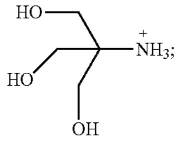

ring A is selected from 5- to 6-membered heteroaryl, and $R_1$ is not H when ring A is 5-membered heteroaryl;

ring B is selected from $C_{6-12}$ acyl, 5- to 10-membered heteroaryl, $C_{3-10}$ cycloalkyl and 3- to 10-membered heterocycloalkyl;

n is selected from 1 and 2;

each of $R_a$, $R_b$, $R_c$ and $R_d$ is independently selected from F, Cl, Br, OH, $NH_2$ and $C_{1-3}$ alkyl, and the $C_{1-3}$ alkyl is optionally substituted with 1, 2, or 3 R;

each of R is independently selected from F, Cl, Br and I;

each of the 5- to 10-membered heteroaryl, 5- to 6-membered heteroaryl and 3- to 10-membered heterocycloalkyl independently contains 1, 2, or 3 heteroatoms or heteroatom groups independently selected from —O—, —NH—, —S— and N.

In some embodiments of the present disclosure, each of $R_a$, $R_b$, $R_c$ and $R_d$ is independently selected from F, Cl, Br, I, $CH_3$, $CF_3$, $CHF_2$, $CH_2F$, $CH_2CH_3$, $CH_2CF_3$, $CH_2CH_2CH_3$,

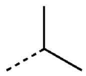

and

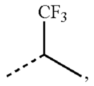

and the other variables are defined herein,

In some embodiments of the present disclosure, the $R_a$ is selected from F, Cl, Br, I, $CH_3$, $CF_3$, $CHF_2$, $CH_2F$, $CH_2CH_3$, $CH_2CF_3$, $CH_2CH_2CH_3$,

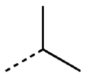

and

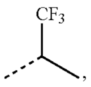

and the other variables are defined herein.

In some embodiments of the present disclosure, the $R_b$ is selected from F, Cl, Br, I, $CH_3$, $CF_3$, $CHF_2$, $CH_2F$, $CH_2CH_3$, $CH_2CF_3$, $CH_2CH_2CH_3$,

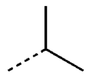

and

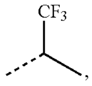

and the other variables are defined herein.

In some embodiments of the present disclosure, the $R_c$ is selected from F, Cl, Br, I, $CH_3$, $CF_3$, $CHF_2$, $CH_2F$, $CH_2CH_3$, $CH_2CF_3$, $CH_2CH_2CH_3$,

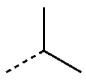

and

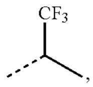

and the other variables are defined herein.

In some embodiments of the present disclosure, the $R_d$ is selected from F, Cl, Br, I, $CH_3$, $CF_3$, $CHF_2$, $CH_2F$, $CH_2CH_3$, $CH_2CF_3$, $CH_2CH_2CH_3$,

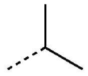 and 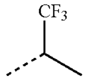, and the other variables are defined herein.

In some embodiments of the present disclosure, the $R_1$ is selected from H, F, Cl, Br, I, $C_{3-6}$ cycloalkyl and 4- to 6-membered heterocycloalkyl, and each of the $C_{3-6}$ cycloalkyl and 4- to 6-membered heterocycloalkyl is independently optionally substituted with 1, 2, or 3 $R_a$, and the other variables are defined herein.

In some embodiments of the present disclosure, the $R_1$ is selected. from H, F, Cl, Br, I, cyclopropyl and oxetanyl, and each of the cyclopropyl and oxetanyl is independently optionally substituted with 1, 2, or 3 $R_a$, and the other variables are defined herein.

In some embodiments of the present disclosure, the $R_1$ is selected from H, F, Cl, Br, I,

 and 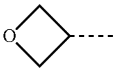, and each of the

 and 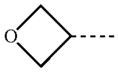

is independently optionally substituted with 1, 2, or 3 $R_a$, and the other variables are defined herein.

In some embodiments of the present disclosure, the $R_1$ is selected from H,

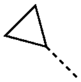 and 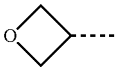, and the other variables are defined herein.

In some embodiments of the present disclosure, the $R_1$ is selected from

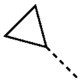 and 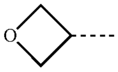, and the other variables are defined herein.

In some embodiments of the present disclosure, the $R_2$ is selected from H, F, Cl, Br, I, $CH_3$, $CF_3$, $CHF_2$, $CH_2F$, $CH_2CH_3$, $CH_2CF_3$, $CH_2CH_2CH_3$,

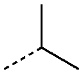 and 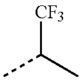, and the other variables are defined herein.

In some embodiments of the present disclosure, the $R_2$ is selected from Cl, and the other variables are defined herein.

In some embodiments of the present disclosure, the $R_3$ is selected from H, F, Cl, Br, I, CN, $CH_3$, $CF_3$, $CHF_2$, $CH_2F$, $CH_2CH_3$, $CH_2CF_3$, $CH_2CH_2CH_3$,

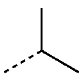 and 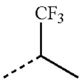, and the other variables are defined herein.

In some embodiments of the present disclosure, tale $R_3$ is selected from H, F, Cl, Br, I, $CH_3$, $CF_3$, $CHF_2$, $CH_2F$, $CH_2CH_3$, $CH_2CF_3$, $CH_2CH_2CH_3$,

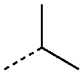 and 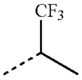, and the other variables are defined herein.

In some embodiments of the present disclosure, the $R_3$ is selected from H, F, $CH_3$ and CN, and the other variables are defined herein, In some embodiments of the present disclosure, the $R_3$ is selected from F, CN and $CH_3$, and the other variables are defined herein.

In some embodiments of the present disclosure, the $R_3$ is selected from F, and the other variables are defined herein.

In some embodiments of the present disclosure, the $R_4$ is selected from H, F, Cl, Br, I, CN, $CH_3$, $CF_3$, $CHF_2$, $CH_2F$, $CH_2CH_3$, $CH_2CF_3$, $CH_2CH_2CH_3$,

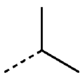 and 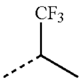, and the other variables are defined herein.

In some embodiments of the present disclosure, the $R_4$ is selected from H, F, Cl, Br, I, $CH_3$, $CF_3$, $CHF_2$, $CH_2F$, $CH_2CH_3$, $CH_2CF_3$, $CH_2CH_2CH_3$,

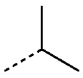 and 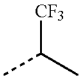, and the other variables are defined herein.

In some embodiments of the present disclosure, the $R_4$ is selected from H, F, Cl, Br, I, $CH_3$, $CF_3$, $CHF_2$, $CH_2F$, $CH_2CH_3$, $CH_2CF_3$, $CH_2CH_2CH_3$,

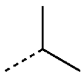

and

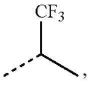

, and the other variables are defined herein.

In some embodiments of the present disclosure, the $R_4$ is selected from H. F, $CH_3$ and CN, and the other variables are defined herein.

In sonic embodiments of the present disclosure, the $R_4$ is selected from F, CN and $CH_3$, and the other variables are defined herein.

In some embodiments of the present disclosure, the $R_4$ is selected from F and $CH_3$, and the other variables are defined herein.

In some embodiments of the present disclosure, the $R_5$ is selected from H,

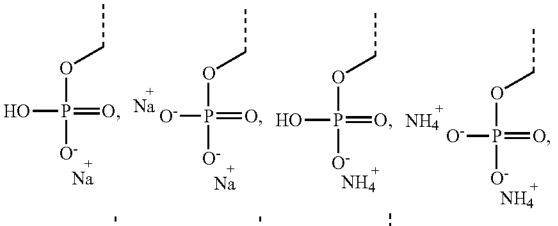

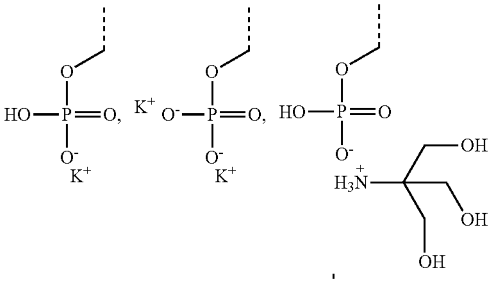

and

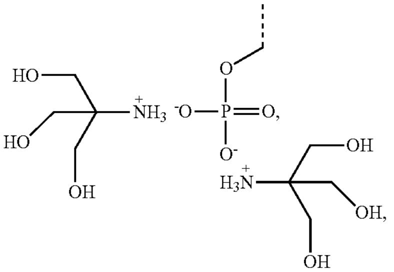

and the other variables are defined herein.

In some embodiments of the present disclosure, the $R_5$ is selected from H,

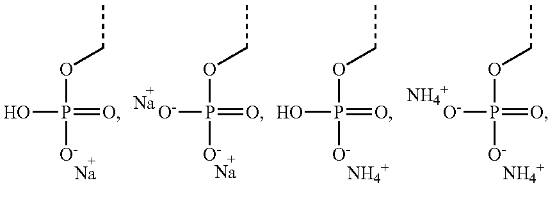

-continued

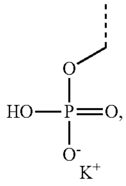

and

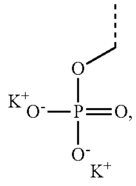

and the other variables are defined herein.

In some embodiments of the present disclosure, the ring A is selected from oxazolyl, isoxazolyl, furanyl, pyridinyl and 1,2,3-triazolyl, and the other variables are defined herein.

In some embodiments of the present disclosure, the ring A is selected from oxazolyl, isoxazolyl, furanyl and pyridinyl, and the other variables are defined herein.

In some embodiments of the present disclosure, the ring A is selected from oxazolyl, isoxazolyl and furanyl, and the other variables are defined herein. In some embodiments of the present disclosure, the ring A is selected from oxazolyl and isoxazolyl, and the other variables are defined herein.

In some embodiments of the present disclosure, the structural unit

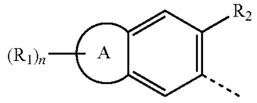

is selected from

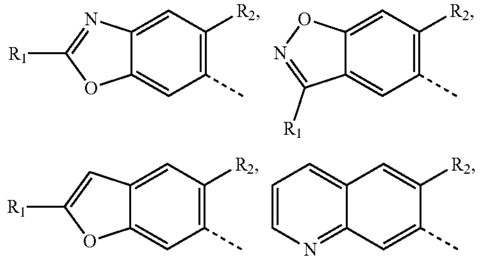

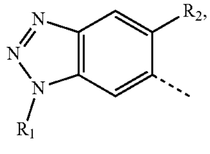

and

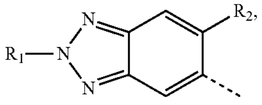

and the other variables are defined herein.

In some embodiments of the present disclosure, the structural unit

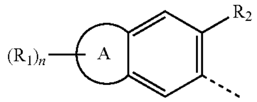

is selected from

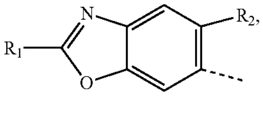 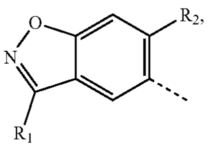

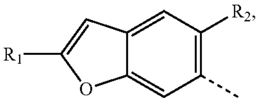 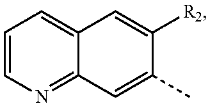 and

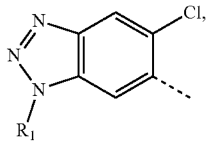

and the other variables are defined herein.

In some embodiments of the present disclosure, the structural unit

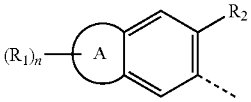

is selected from

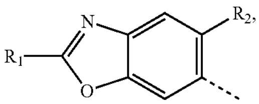 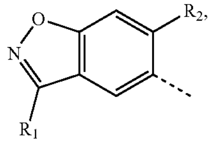

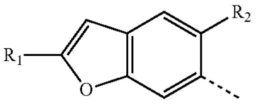 and 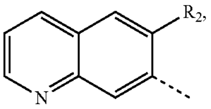

and the other variables are defined herein.

In some embodiments of the present disclosure, the structural unit

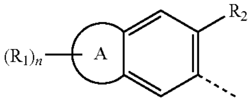

is selected from

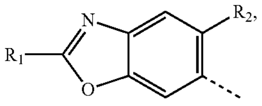 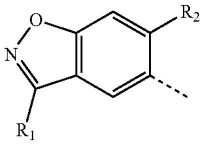 and

-continued

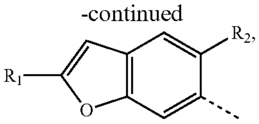

and the other variables are defined herein.

In some embodiments of the present disclosure, the structural unit

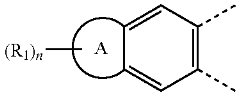

is selected from

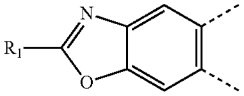 and 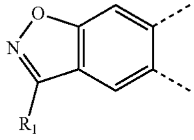, and the other variables are defined herein.

In some embodiments of the present disclosure, the structural unit

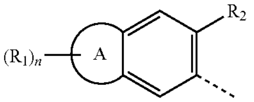

is selected from

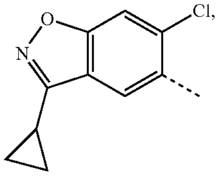 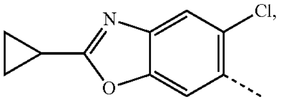

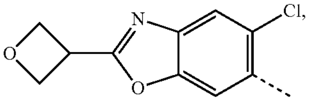

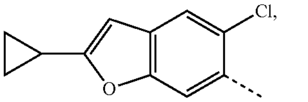 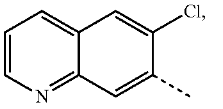

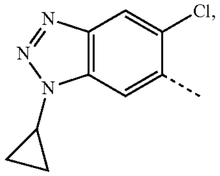

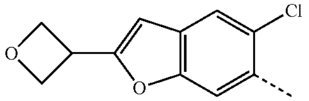 and

-continued

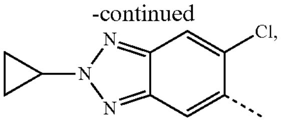

and the other variables are defined herein.

In some embodiments of the present disclosure, the structural unit

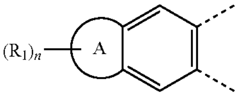

is selected from

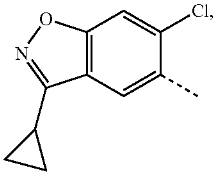
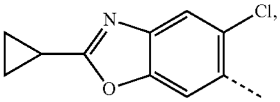
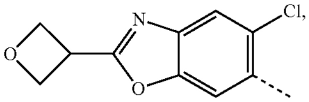
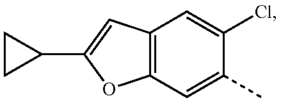
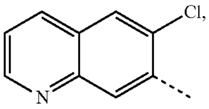
and
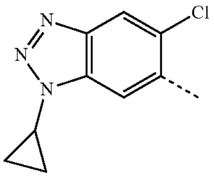
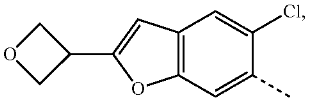

and the other variables are defined herein.

In some embodiments of the present disclosure, the structural unit

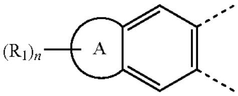

is selected from

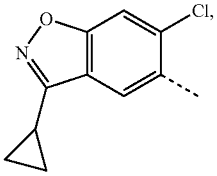
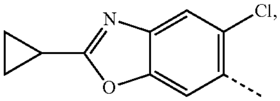

-continued

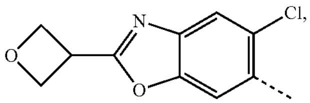
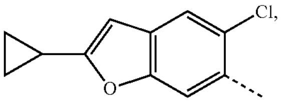
and
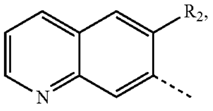

and the other variables are defined herein.

In some embodiments of the present disclosure, the structural unit

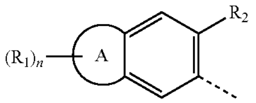

is selected from

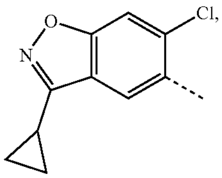
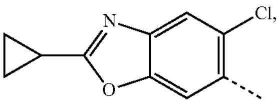
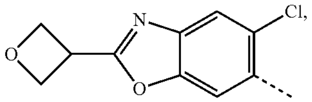
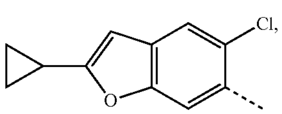
and
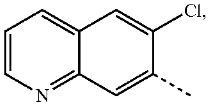

and the other variables are defined herein.

In some embodiments of the present disclosure, the structural unit

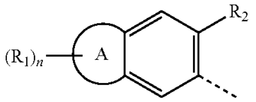

is selected from

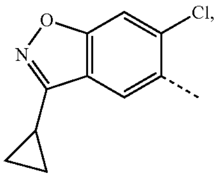
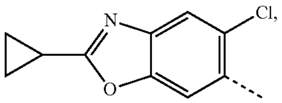
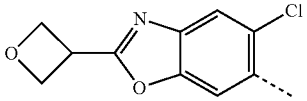
and

-continued

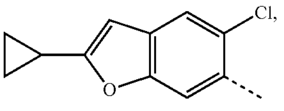

and the other variables are defined herein.

In some embodiments of the present disclosure, the structural unit

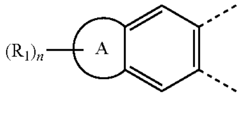

is selected from

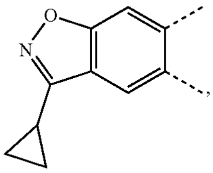 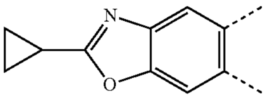 and

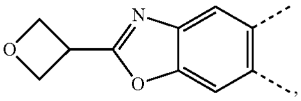

and the other variables are defined herein.

In some embodiments of the present disclosure, the ring B is selected from $C_{6-10}$ aryl, $C_{3-6}$ cycloalkyl and 4- to 6-membered heterocycloalkyl, and the other variables are defined herein.

In some embodiments of the present disclosure, the ring B is selected from $C_{6-10}$ aryl, 5- to 6-membered heteroaryl, $C_{3-6}$ cycloalkyl and 4- to 6-membered heterocycloalkyl, and the other variables are defined herein.

In some embodiments of the present disclosure, the ring B is selected from phenyl,

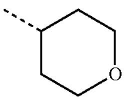 and 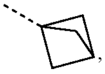

and the other variables are defined herein.

In some embodiments of the present disclosure, the ring B is selected from phenyl,

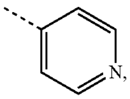 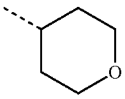 and 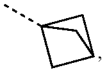

and the other variables are defined herein.

In some embodiments of the present disclosure, the ring B is selected from phenyl,

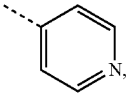 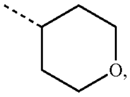 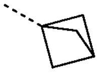 and

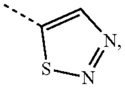

and the other variables are defined herein.

In some embodiments of the present disclosure, the structural unit is

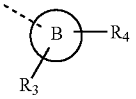

selected from

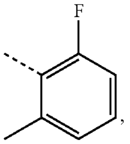 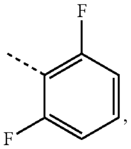 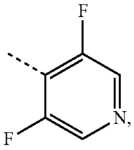

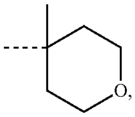 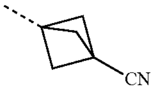 and 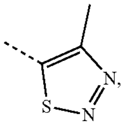

and the other variables are defined herein.

The present disclosure provides a compound represented by formula (P) isomer thereof or a pharmaceutically acceptable salt thereof, (P)

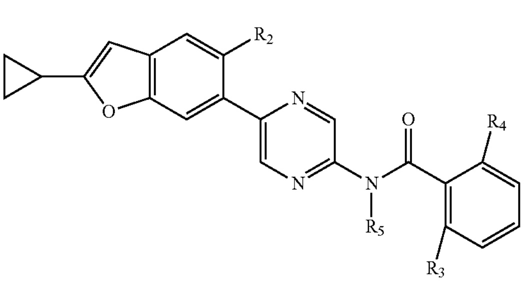

wherein, $R_2$ is selected from H, F, Cl, Br and I;

$R_3$ is selected from H, F, Cl, Br, I, CN and $CH_3$;

$R_4$ is selected from H. F, Cl, Br, I, CN and $CH_3$;

$R_5$ is selected from

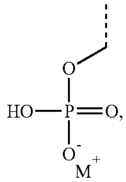

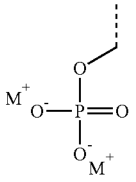

and

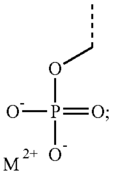

each of $M^+$ is independently selected from $Na^+$, $NH_4^+$, $K^+$, choline,

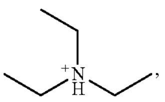

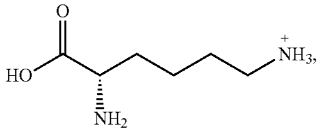

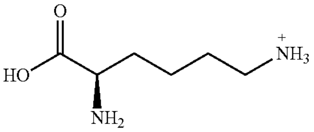

and

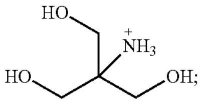

each of $M^{2+}$ is independently selected from $Ca^{2+}$, $MG^{2+}$, $Zn^{2+}$ and

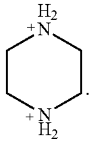

In some embodiments of the present disclosure, the $R_2$ is selected from Cl, and the other variables are defined herein.

In some embodiments of the present disclosure, the $R_3$ is selected from H, F, $CH_3$ and CN, and the other variables are defined herein.

In some embodiments of the present disclosure, the $R_4$ is selected from H, F, $CH_3$ and CN, and the other variables are defined herein.

In some embodiments of the present disclosure, the $R_5$ is selected from H,

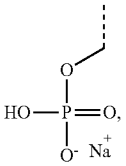

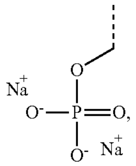

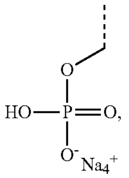

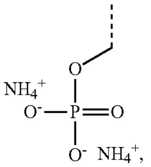

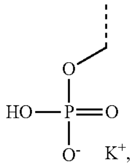

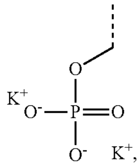

-continued

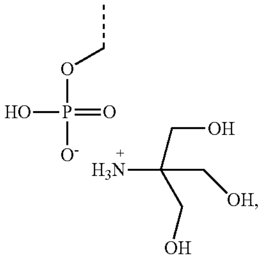

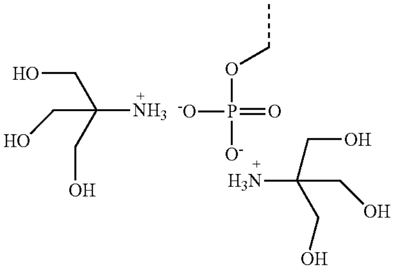

and

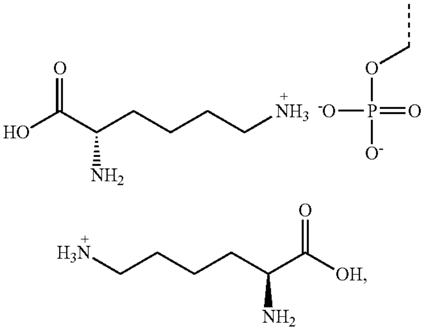

and the other variables are defined herein.

In some embodiments of the present disclosure, the compound, the isomer thereof, or the pharmaceutically acceptable salt thereof, and the compound is selected from (I-1)

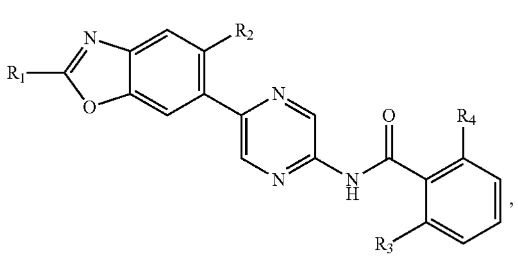

(I-2)

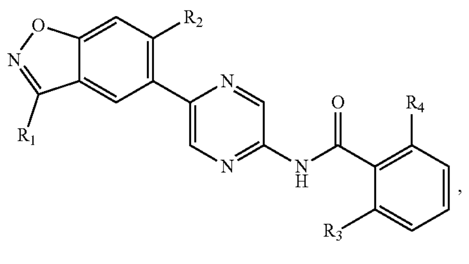

-continued
(I-3)
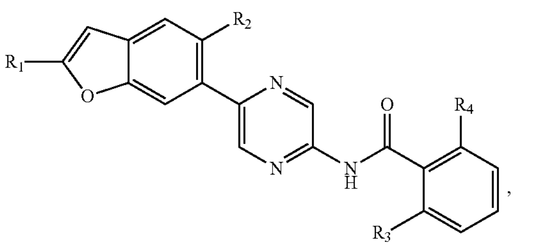
(II-1)
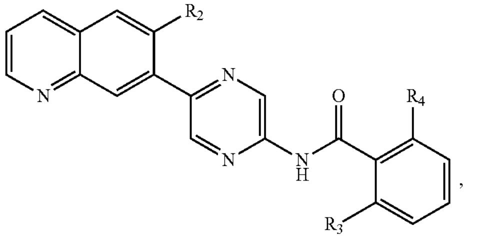
(II-2)
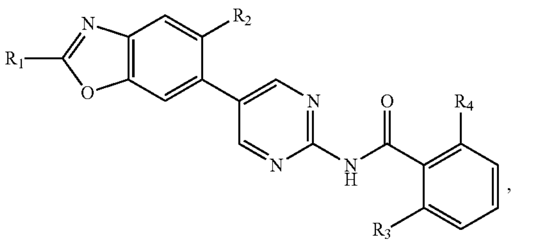
(II-3)
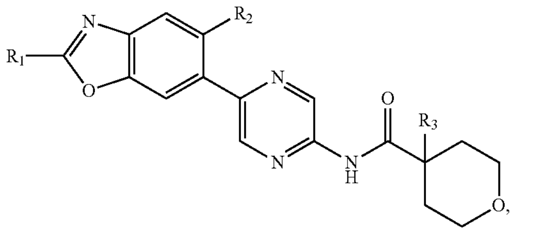
(II-4)
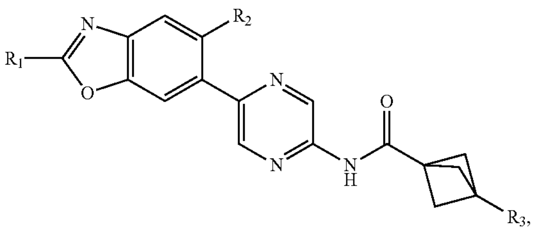
(III-1)
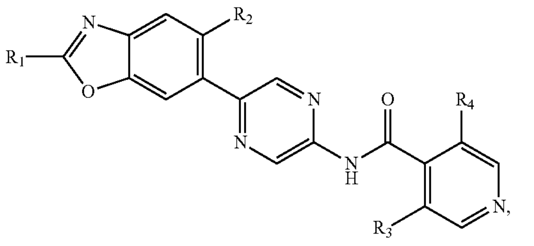
-continued
(V-1)
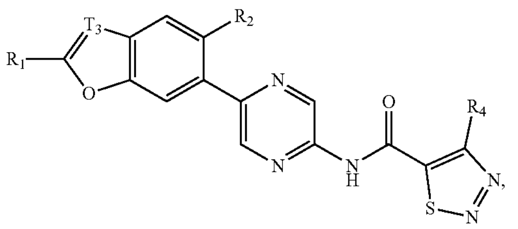
(VI-1)
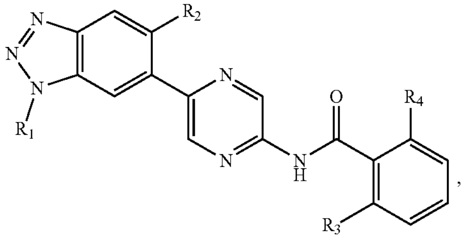
(VII-1)
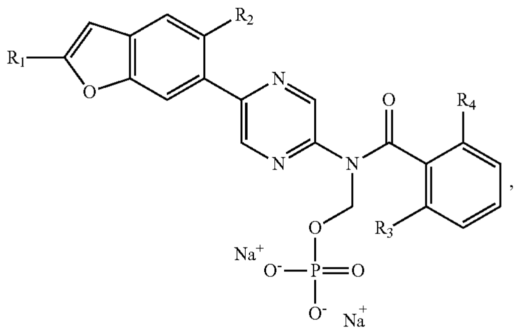
(VIII-1)
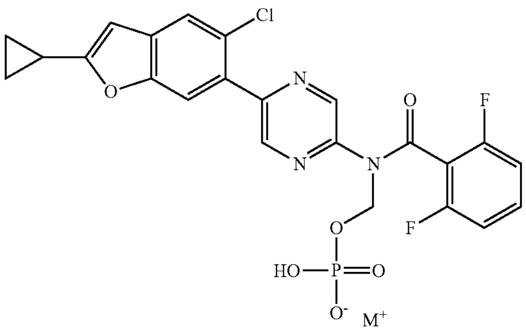
and
(VIII-2)
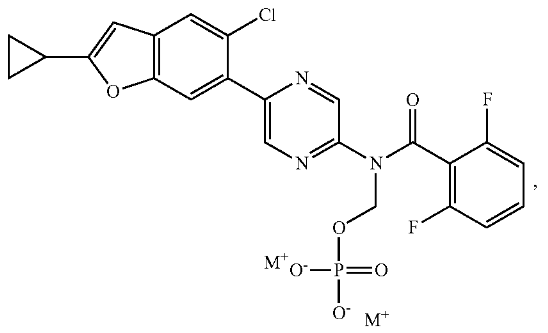
wherein, $T_3$ is selected from CH and N; $R_1$, $R_2$, $R_3$, $R_4$ and $M^+$ are defined herein.

Still other embodiments of the present disclosure result from any combination of the above variables.
The present disclosure also provides a compound represented by the following formula or a pharmaceutically acceptable salt thereof,
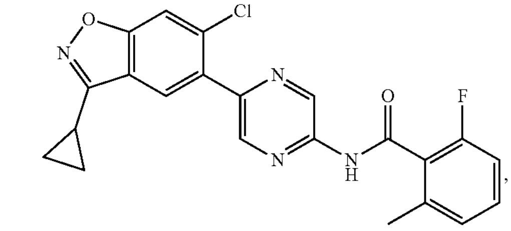
,
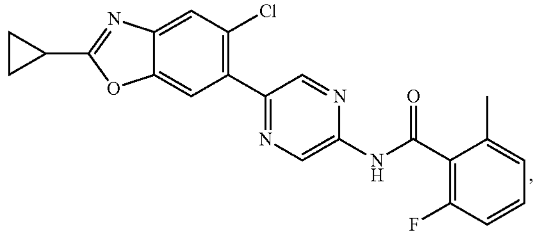
,
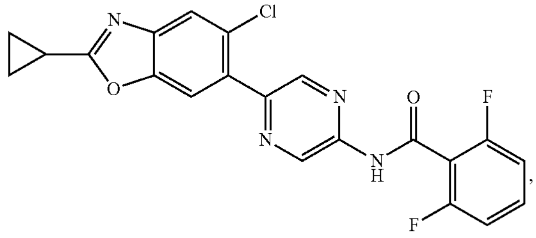
,
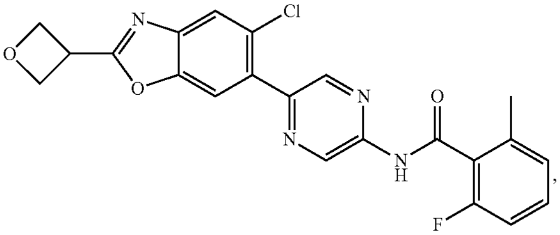
,
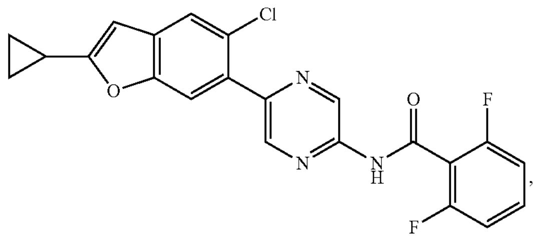
,
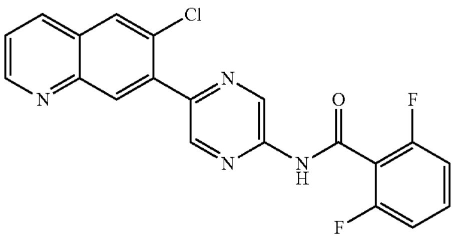
,
-continued
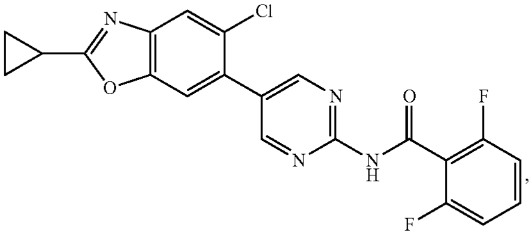
,
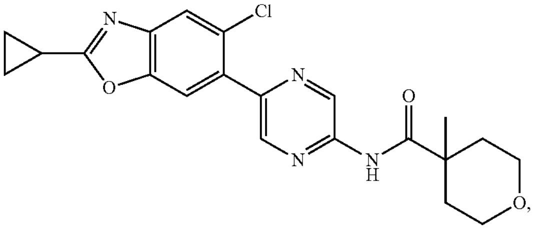
,
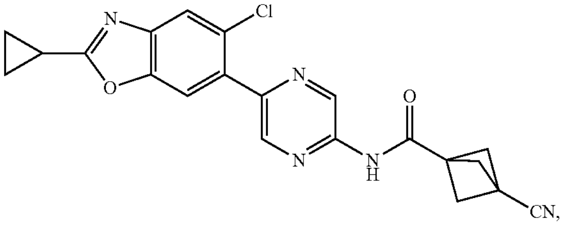
,
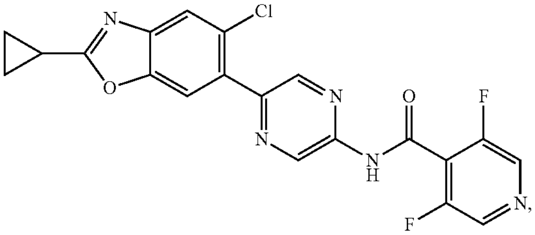
,
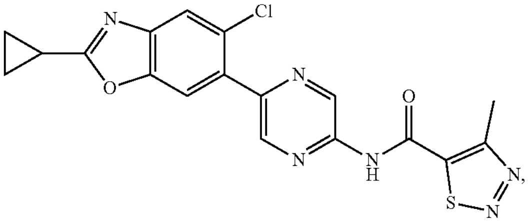
,
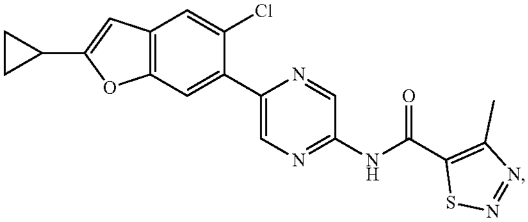
,
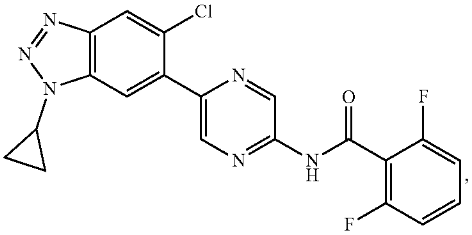
, -continued

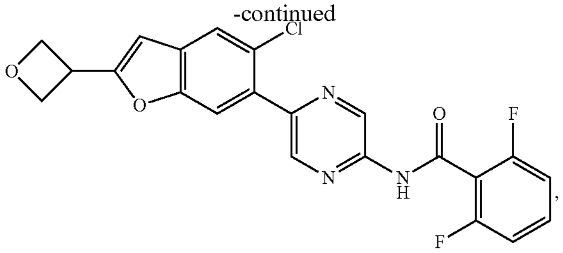

,

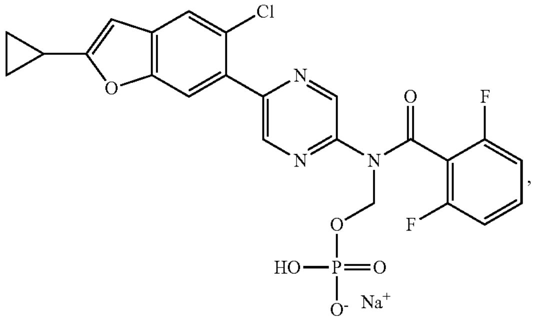

,

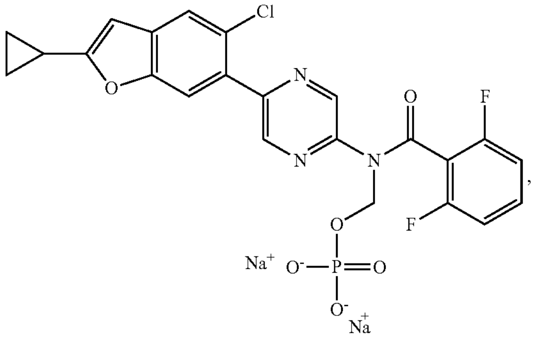

,

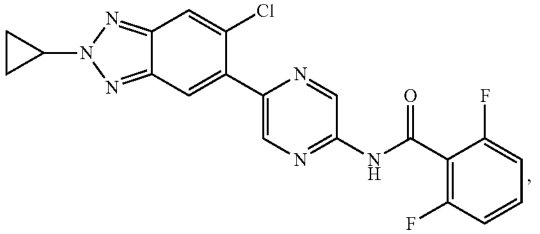

,

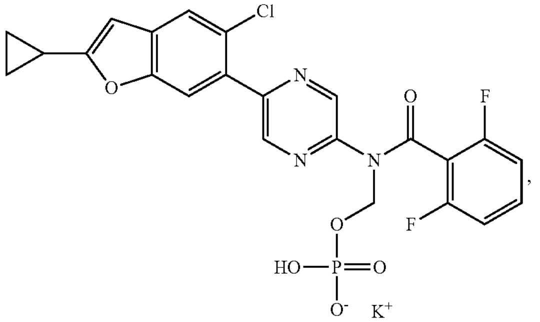

,

-continued

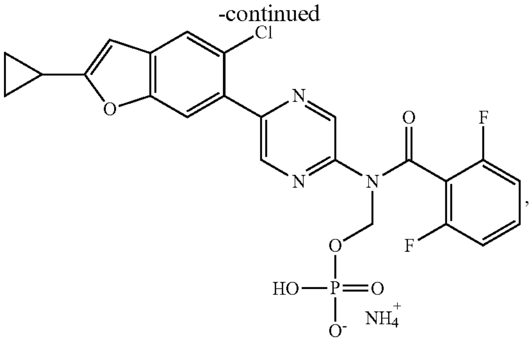

,

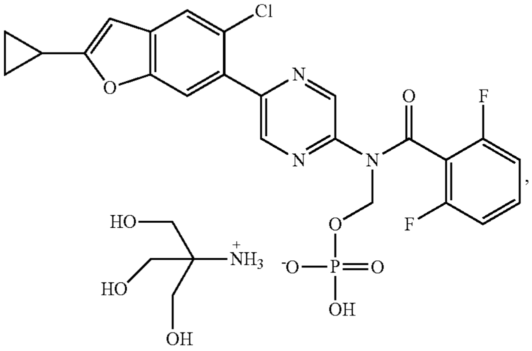

,

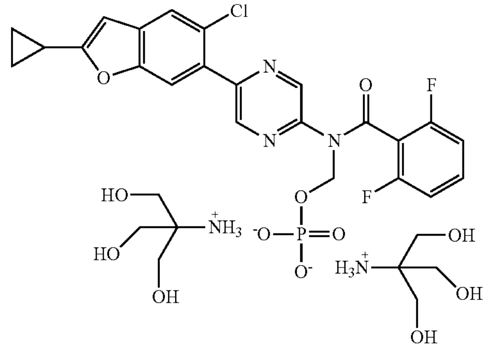

and

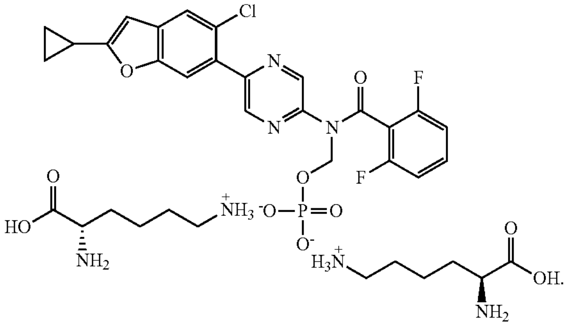

The present disclosure also provides a pharmaceutical composition comprising a therapeutically effective amount of the compound described above or the pharmaceutically acceptable salt thereof as an active ingredient and a pharmaceutically acceptable carrier.

The present disclosure also provides a pharmaceutical composition comprising a therapeutically effective amount of the compound described above, the isomer thereof or the pharmaceutically acceptable salt thereof as an active ingredient and a pharmaceutically acceptable carrier.

The present disclosure also provides a use of the compound described above or the pharmaceutically acceptable salt thereof in the manufacture of a medicament related to CRAC inhibitors.

The present disclosure also provides a use of the compound described above, the isomer thereof or the pharmaceutically acceptable salt thereof in the manufacture of a medicament related to CRAC inhibitors.

The present disclosure also provides a use of the pharmaceutical composition described above in the manufacture of a medicament related to CRAC inhibitors.

Technical Effect

The compounds of the present disclosure have significant inhibitory effects on CRAC and inflammatory cytokines, can alleviate typical symptoms of acute pancreatitis, and have excellent pharmacokinetic properties.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral firm of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

For a drug or pharmacologically active agent, the term "effective amount" or "therapeutically effective amount" refers to an amount of the drug or agent that is nontoxic but sufficient to achieve the desired effect. For oral dosage forms of the present disclosure, an "effective amount" of one active substance in a composition refers to the amount required to achieve the desired effect when combined with another active substance in the composition. Determination of the effective amount will vary from person to person, depending on the age and general condition of the recipient, and also on the particular active substance, and suitable effective amounts in each case may be determined by one skilled in the art according to routine experimentation.

The compounds of the present disclosure may exist in specific geometric or stereoisomeric forms. The present disclosure contemplates all such compounds, including cis and trans isomers, (−)-and (+)-enantiomers, (R)-and (S)-enantiomers, diastereomers isomers, (D)-isomers, (L)-isomers, and racemic and other mixtures thereof, such as enantiomers or diastereomerc enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomers" or "optical isomers" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which the molecules have two or more chiral centers and are not minor images of each other.

Unless otherwise specified, "(+)" refers to dextrorotation, "(−)" refers to levorotation, and or "(±)" refers to racemic.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ), a wave line ( ) is used to represent a wedged solid bond ( ) or a wedged dashed bond ( ), or the wave line ( ) is used to represent a straight solid bond ( ) and a straight dashed bond ( ).

The compounds of the present disclosure may exist in specific. Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

Unless otherwise specified, the term "$C_{1-3}$ alkyl" refers to a linear or branched saturated hydrocarbon group consisting of 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, "$C_{3-10}$ cycloalkyl" refers to a saturated cyclic hydrocarbon group consisting of 3 to 10 carbon atoms, including monocyclic, bicyclic and tricyclic ring systems, wherein bicyclic and tricyclic ring systems include spiro rings, fused rings and bridged rings. The $C_{3-10}$ cycloalkyl includes $C_{3-8}$, $C_{3-6}$, $C_{3-5}$, $C_{4-10}$, $C_{4-8}$, $C_{4-6}$, $C_{4-5}$, $C_{5-8}$, or $C_{5-6}$ and the like; it may be monovalent, divalent or polyvalent. Examples of $C_{3-10}$ cycloalkyl include, but are not limited to, cyclopropyl, cyclobutyl, cyclopentyl, cyclohexyl, cycloheptyl, norbomyl, [2.2.2]bicyclooctyl, [4.4.0]bicyclodecyl, and the like.

Unless otherwise specified, "$C_{3-6}$ cycloalkyl" refers to a saturated cyclic hydrocarbon group consisting of 3 to 6 carbon atoms, including monocyclic, bicyclic and tricyclic ring systems, wherein bicyclic and tricyclic ring systems include spiro rings, fused rings and bridged rings. The $C_{3-6}$ cycloalkyl includes $C_{3-5}$, $C_{4-5}$, and $C_{5-6}$ cycloalkyl and the like; it may be monovalent, divalent or polyvalent. Examples of $C_{3-6}$ cycloalkyl include, but are not limited to, cyclopropyl, cyclobutyl, cyclopentyl, cyclohexyl, and the like.

Unless otherwise specified, the term "3- to 10-membered heterocycloalkyl" by itself or in combination with other terms means refers to a saturated cyclic group consisting of 3 to 10 ring atoms; 1, 2, 3, or 4 ring atoms of which are heteroatoms independently selected from O, S and N, and the remaining ring atoms are carbon atoms; wherein the nitrogen atom is optionally quaternized and the nitrogen and sulfur heteroatoms may optionally be oxidized (i.e., NO and $S(O)_p$, p is 1 or 2). It includes monocyclic, bicyclic and tricyclic ring systems, wherein bicyclic and tricyclic ring systems include spiro rings, fused rings, and bridged rings. In addition, in terms of the "3- to 10-membered heterocycloalkyl", the heteroatom can occupy the position of attachment of the heterocycloalkyl to the rest of the molecule. The 3- to 10-membered heterocycloalkyl includes 3- to 8-membered, 3- to 6-membered, 3- to 5-membered, 4- to 6-membered, 5- to 6-membered, 4-membered, 5-membered and 6-membered heterocycloalkyl, and the like. Examples of 3- to 10-membered heterocycloalkyl include, but are not limited to, azetidinyl, oxetanyl, pyrrolidinyl, pyrazolidinyl, imidazolidinyl, tetrahydrothienyl (including tetrahydrothien-2-yl and tetrahydrothien-3-yl, etc), tetrahydrofuranyl (including tetrahydrofuran-2-yl, etc.), tetrahydropyranyl, piperidinyl (including 1-piperidinyl, 2-piperidinyl, and 3-piperidinyl, etc.). piperazinyl (including 1-piperazinyl and 2-piperazinyl, etc.), morpholinyl (including 3-morpholinyl and 4-morpholinyl, etc), dioxanyl, dithianyl, isoxazolidinyl, isothiazolidinyl, 1,2-oxazinyl, 1,2-thiazinyl, hexahydropyridazinyl, homopiperazinyl, homopiperidinyl, or dioxepanyl, and the like.

Unless otherwise specified, the term "4- to 6-membered heterocycloalkyl" by itself or in combination with other terms refers to a saturated cyclic group consisting of 4 to 6 ring atoms; 1, 2, 3, or 4 ring atoms of which are heteroatoms independently selected from O, S and N, and the remaining ring atoms are carbon atoms; wherein the nitrogen atom is optionally quatemized, and the nitrogen and sulfur heteroatoms may optionally be oxidized (i.e., NO and $S(O)_p$, p is 1 or 2). It includes monocyclic and bicyclic ring systems, wherein bicyclic ring systems include spiro rings, fused rings, and bridged rings. In addition, in terms of the "4- to 6-membered heterocycloalkyl", the heteroatom can occupy the position of attachment of the heterocycloalkyl to the rest of the molecule. The 4- to 6-membered heterocycloalkyl includes 5- to 6-membered, 4-membered, 5-membered, and 6-membered heterocycloalkyl and the like. Examples of 4- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl and tetrahydrothien-3-yl, etc.), tetrahydrofuranyl (including tetrahydrofuran-2-yl, etc.), tetrahydropyranyl, piperidinyl (including 1-piperidinyl, 2-piperidinyl, and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, or homopiperidinyl, and the like.

Unless otherwise specified, the terms "5- to 10-membered heteroaromatic ring" and "5- to 10-membered heteroaryl" are used interchangeably herein; and the term "5- to 10-membered heteroaryl" refers to a cyclic group consisting of 5 to 10 ring atoms having a conjugated π-electron system; 1, 2, 3, or 4 ring atoms of which are heteroatoms independently selected from O, S and N, and the remaining ring atoms are carbon atoms. It may be a monocyclic, fused bicyclic or fused tricyclic ring system, wherein each ring is aromatic. Wherein the nitrogen atoms are optionally quatemized, and the nitrogen and sulfur heteroatoms may optionally be oxidized (i.e., NO and $S(O)_p$, p is 1 or 2). The 5- to 10-membered heterocyclyl may be attached to the rest of the molecule through a heteroatom or a carbon atom. The 5- to 10-membered heteroaryl includes 5- to 8-membered, 5- to 7-membered, 5- to 6-membered, 5-membered, 6-membered heteroaryl, and the like. Examples of the 5- to 10-membered heteroaryl include, but are not limited to, pyrrolyl (including N-pyrrolyl, 2-pyrrolyl and 3-pyrrolyl, pyrazolyl (including 2-pyrazolyl and 3-pyrazolyl, imidazolyl (including N-imidazolyl, 2-imidazolyl, 4-imidazolyl and 5-imidazolyl, etc.), oxazolyl (including 2-oxazolyl, 4-oxazolyl, and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl, and 5-isoxazolyl, etc.), thiazolyl (including 2-thiazolyl, 4-thiazolyl, and 5-thiazolyl, etc.), furanyl (including 2-furanyl and 3-furanyl, etc.), thienyl (including 2-thienyl and 3-thienyl, etc.), pyridinyl (including 2-pyridinyl, 3-pyridinyl, and 4-pyridinyl, etc.), pyrazinyl, pyrimidinyl (including 2-pyrimidinyl and 4-pyrimidinyl, etc.), benzothiazolyl (including 5-benzothiazolyl, etc.), purinyl, benzimidazolyl (including 2-benzimidazolyl, etc.), benzoxazolyl, indolyl (including 5-indolyl, etc.), isoquinolinyl (including 1-isoquinolinyl and 5-isoquinolinyl, etc.), quinoxalinyl (including 2-quinoxalinyl and 5-quinoxalinyl, etc.), or quinolinyl (including 3-quinolinyl and 6-quinolinyl, etc.).

Unless otherwise specified, the terms "5- to 6-membered heteroaromatic ring" and "5- to 6-membered heteroaryl" are used interchangeably herein, and the term "5- to 6-membered heteroaryl" refers to a monocyclic group consisting of 5 to 6 ring atoms having a conjugated a-electron system; 1, 2, 3, or 4 ring atoms of which are heteroatoms independently selected from O, S and N, and the remaining ring atoms are carbon atoms. Wherein the nitrogen atoms are optionally quaternized, and the nitrogen and sulfur heteroatoms may optionally be oxidized (i.e., NO and $S(O)_p$, p is 1 or 2). The 5- to 6-membered heteroaryl may be attached to the rest of the molecule through a heteroatom or a carbon atom. The 5- to 6-membered heteroaryl includes 5-membered and 6-membered heteroaryl. Examples of the 5- to 6-membered heteroaryl include, but are not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 4-imidazolyl and 5-imidazolyl, etc.), oxazolyl (including 2-oxazolyl, 4-oxazolyl, and 5-oxazolyl, triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl, and 5-isoxazolyl, etc.), thiazolyl (including 2-thiazolyl, 4-thiazolyl, and 5-thiazolyl, etc), furanyl (including 2-furanyl and 3-furanyl, etc.), thienyl (including 2-thienyl and 3-thienyl, etc.), pyridinyl (including 2-pyridinyl, 3-pyridinyl, and 4-pyridinyl, etc.), pyrazinyl, or pyrimidinyl (including 2-pyrimidinyl and 4-pyrimidinyl, etc.).

Unless otherwise specified, the terms "$C_{6-12}$ aromatic ring" and "$C_{6-12}$ aryl" are used interchangeably herein, and the terms "$C_{6-12}$ aromatic ring" or "$C_{6-12}$ aryl" refers to a cyclic hydrocarbon group consisting of 6 to 12 carbon atoms having a conjugated π-electron system. It may be a monocyclic, fused bicyclic, or fused tricyclic ring system, wherein each ring is aromatic. It can be monovalent, divalent, or polyvalent, and $C_{6-12}$ aryl includes $C_{6-10}$, $C_{6-9}$, $C_{6-8}$, $C_{12}$, $C_{10}$, and $C_6$ aryl, and the like. Examples of $C_{6-12}$ alkyl groups include, but are not limited to, phenyl, naphthyl (including 1-naphthyl and 2-naphthyl, etc).

Unless otherwise specified, $C_{n-n+m}$ or $C_{n-Cn+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n-membered to n+m-membered means that the number of atoms on the ring is from n to n+m, for example, 3- to 12-membered ring includes 3-membered ring; 4-membered ring, 5-membered ring, 6-membered ring, 7-membered ring, 8-membered ring, 9-membered ring, 10-membered ring, 11-membered ring, and 12-membered ring, and any range from n to is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring and the like.

The term "leaving group" refers to a functional group or atom which can be replaced by another functional group or atom through a substitution reaction (such as affinity substitution reaction). For example, representative leaving groups include trill ate; chlorine, bromine, and iodine; sulfonate group, such as mesylate, tosylate, p-bromobenzenesulfonate, toluenesulfonates and the like; acyloxy, such as acetoxy, trifluoroacetoxy and the like.

The term "protecting group" includes; but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl, such as methyl, ethyl, and tern-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvents used in the present disclosure are commercially available. The following abbreviations are used in the present disclosure: HATU refers to O-(7-azabenzotriazol-1-yl)-N,N,N',N'-tetramethyluronium hexafluorophosphate; eq refers to equivalents and equal quantity; M refers to mol/L; PE refers to petroleum ether; DMF refers to N,N-dimethylformamide; DMSO refers to dimethyl sulfoxide; MeOH refers to methanol; CBz refers to benzyloxycarbonyl, an amine protecting group; HCl refers to hydrochloric acid; ACN refers to acetonitrile; $NH_4HCO_3$ refers to ammonium bicarbonate; AMY refers to amylase; LPS refers to lipase; PE in fluorescein PE refers to phycoerythrin; Solutol refers to polyethylene glycol-15 hydroxystearate; PEG400 refers to polyethylene glycol-400.

The compounds are named according to common nomenclature in the art or using ChemDraw® software, and the commercially available compounds adopt the name of supplier catalogue.

DETAILED DESCRIPTION OF THE PREFERRED EMBODIMENT

Figure 1:
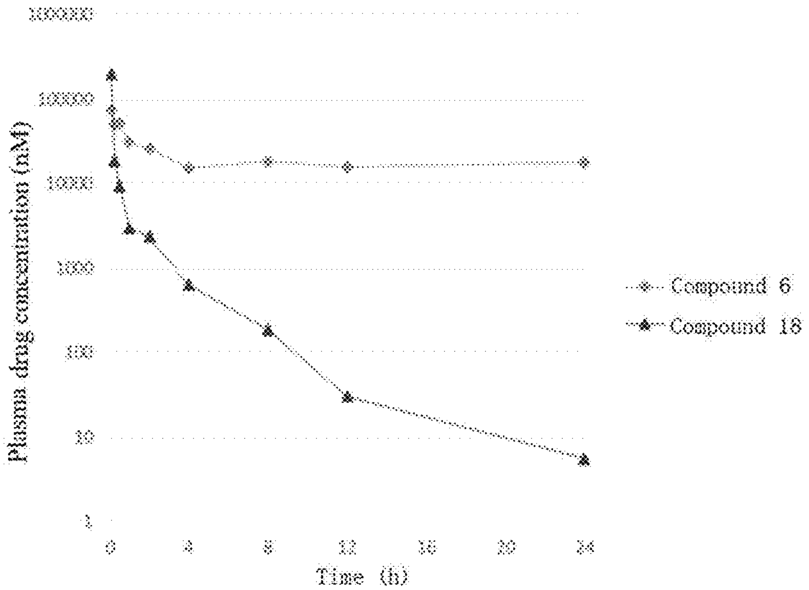
FIG. 1 shows a drug-time curve of compound 18 in mice pharmacokinetic evaluation experiment.

The following embodiments describe the present disclosure in detail, but they are not meant to impose any unfavorable limitation on the present disclosure. The present disclosure has been described in detail herein, and its specific embodiments are also disclosed. It will be apparent to those skilled in the art that various changes and modifications can be made to the specific embodiments without departing from the spirit and scope of the present disclosure.

Reference Embodiment 1: Fragment BB-1

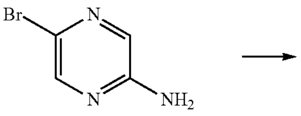

BB-1-1

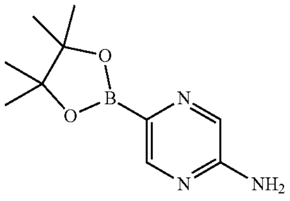

BB-1

Step 1: Synthesis of BB-1

BB-1-1 (2 g, 15.44 mmol), bis(pinacolato)diboron (4.31 g, 16.98 mmol), potassium acetate (3.79 g, 38.60 mmol), tricyclohexyl phosphine (173.18 mg, 617.53 μmol), and 1,4-dioxane were added to a reaction flask, and the reaction system was replaced with nitrogen three times, and then palladium acetate (69.32 mg, 308.77 μmol) was added; the reaction system was replaced with nitrogen three times again, then the mixture was stirred at 110° C. for 16 hours. The temperature was lowered to room temperature after the reaction was completed, then the reaction mixture was filtered, and the filtrate was concentrated under reduced pressure to obtain a crude product. The crude product was purified by flash column chromatography (petroleum ether: ethyl acetate (V/V)=1:0-1:1, V/V) to obtain a purified product. Product BB-1 was obtained. MS m/z: 140[M−81]$^+$, $^1$H NMR (400 MHz, DMSO-$d_6$) δ=8.10 (s, 1 H), 7.98 (d, J=1.2 Hz, 1 H), 6.78 (s, 2 H), 1.26 (s, 12 H).

Reference Embodiment 2: Fragment BB-2

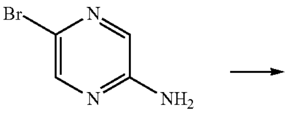

BB-2-1

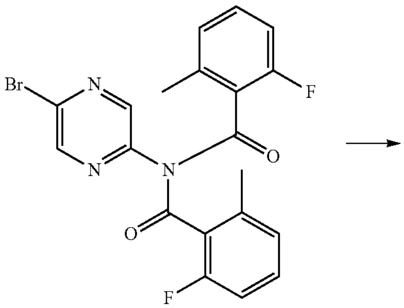

BB-2-2

-continued

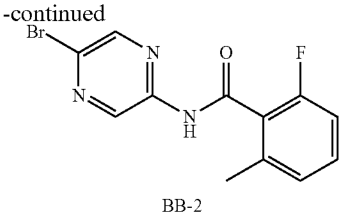

BB-2

Step 1: Synthesis of BB-2-2

Starting material BB-2-1 (5 g, 28.74 mmol) and solvent dichloromethane (30 mL) were added to a pre-dried flask, then reagents N,N-diisopropylethylamine (9.28 g, 71.84 mmol) and 4-(dimethylamino)pyridine (351.07 mg, 2.87 mmol) were added, and then starting material 2-fluoro-6-methyl-benzoyl chloride (10.91 g, 63.22 mmol) was added, and the mixture was stirred at 25° C. for 5 hours. The reaction mixture was concentrated directly under reduced pressure to obtain a crude product. The crude product was purified by flash column chromatography (petroleum ether: ethyl acetate (V/V)=10:1-1:1) to obtain BB-2-2. MS m/z: 446[M+H]$^+$.

Step 2: Synthesis of BB-2

Starting material BB-2-2 (12 g, 26.89 mmol) and solvents tetrahydrofuran (60 mL) and methanol (60 mL) were added to a pre-dried flask, then sodium hydroxide aqueous solution (2 M, 60 mL) was added, and the mixture was stirred at 25° C. for 1 hour. 50 mL of water was added to the reaction system, and the resulting mixture was extracted with ethyl acetate (150 mL×3); the organic phases were combined, washed with 20 mL of saturated brine, dried over anhydrous sodium sulfate, filtered, and concentrated under reduced pressure to obtain a crude product. The crude product was purified by silica gel column chromatography (petroleum ether:ethyl acetate (V/V)=1:0-5:1) to obtain BB-2. MS m/z: 310[M+H]$^+$.

Reference Embodiment 4: Fragment BB-3

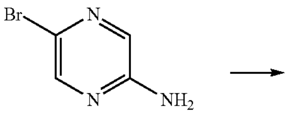

BB-3-1

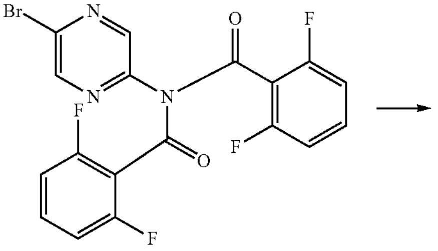

BB-3-2

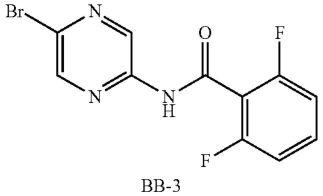

BB-3

Step 1: Synthesis of Compound BB-3-2

Starting material BB-3-1 (2 g, 11.49 mmol) and anhydrous dichloromethane (50 mL) were added to a pre-dried single-neck flask, then triethylamine (3.49 g, 34.48 mmol, 4.80 mL), N,N-dimethylaminopyridine (140.43 mg, 1.15 mmol), and 2,6-difluorobenzoyl chloride (4.46 g, 25.29 mmol, 3.19 mL) were added, and the mixture was reacted at 40° C. for 3 hours, directly concentrated under reduced pressure to obtain a crude product. The crude product was purified by flash column chromatography (petroleum ether: ethyl acetate=10:1-5:1) to obtain BB-3-2. MS m/z: 453.9 [M+H]$^+$.

Step 2: Synthesis of Compound BB-3

Starting material BB-3-2 (5 g, 11.01 mmol) and solvents tetrahydrofuran (60 mL) and methanol (60 mL) were added to a pre-dried flask, then sodium hydroxide aqueous solution (2 M, 24.56 mL) was added, and the mixture was stirred at 25° C. for 1 hour. 50 mL of water was added to the system, and the resulting mixture was extracted with ethyl acetate (150 mL×3); the organic phases were combined, washed with 20 mL of saturated brine, dried over anhydrous sodium sulfate, filtered, and concentrated under reduced pressure to obtain a crude product. The crude product was purified by silica gel column chromatography (petroleum ether:ethyl acetate=3:1-2:1) to obtain BB-3. MS m/z: 314[M+H]$^+$. $^1$NMR (400 MHz, $CDCl_3$) δ ppm 9.50 (s, 1 H), 8.53 (br s, 1 H), 8.34 (d, J=1.60 Hz, 1 H), 7.52 (tt, J=8.40, 6.00 Hz, 1 H), 7.07 (t, J=8.00 Hz, 2 H).

Reference Embodiment 5: Fragment BB-4

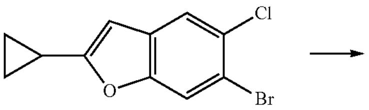

6-3

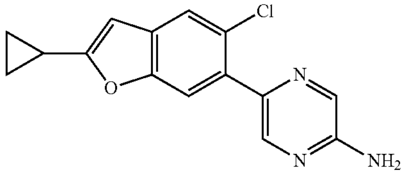

BB-4

Step 1: Synthesis of Compound BB-4

Compound 6-3 (5 g, 18.41 mmol) and BB-1 (8.14 g, 36.83 mmol) were dissolved in tetrahydrofuran (150 mL) and water (30 mL), then to the resulting mixture were added potassium phosphate (9.77 g, 46.03 mmol) and 1,1'-bis(di-tert-butylphosphino)ferrocene palladium dichloride (1.80 g, 2.76 mmol) under the protection of nitrogen. After the reaction was stirred at 85° C. for 12 hours, the reaction mixture was diluted with water (200 mL), and extracted with ethyl acetate (150 mL×3); the organic phases were combined, washed with saturated brine, dried over anhydrous sodium sulfate, filtered, and concentrated to obtain a crude product. The crude product was purified by silica gel column chromatography (petroleum ether:ethyl acetate (V/V)=1:1-0:1) to obtain compound BB-4.

Embodiment 1: Preparation of Compound 2

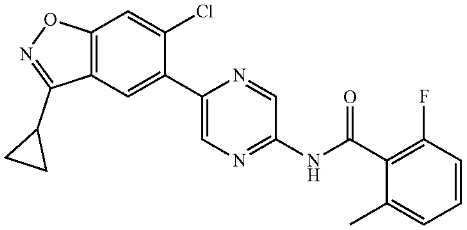

2

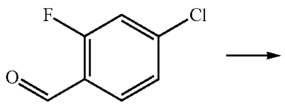

2-1

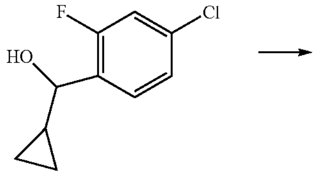

2-2

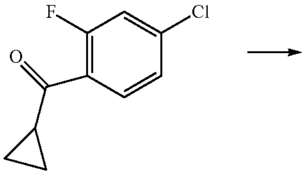

2-3

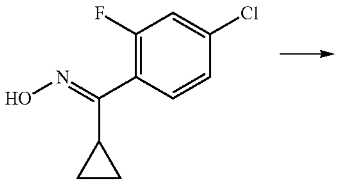

2-4

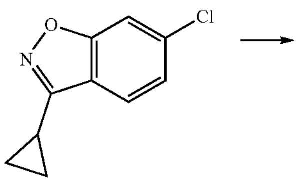

2-5

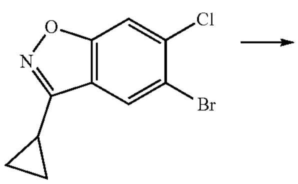

2-6

-continued

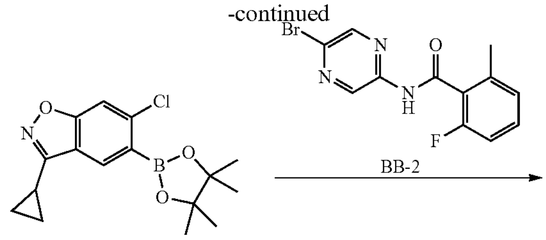

2-7

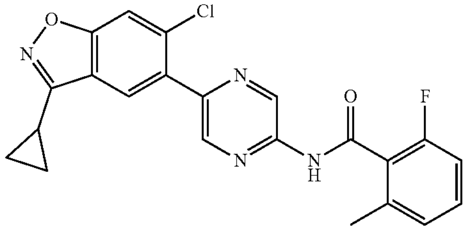

2

Step 1: Synthesis of Compound 2-2

2-1 (5.0 g, 31.53 mmol) and tetrahydrofuran (50 mL) were added to a reaction flask. The reaction mixture was cooled to −70° C., and cyclopropylmagnesium bromide (0.5 M, 151.36 mL) was added. The resulting mixture was continued to stir at −70° C. for 1 hour, then slowly warmed to 25° C., and stirred at 25° C. for 1 hour. To the reaction mixture was added saturated ammonium chloride aqueous solution (200 mL), and the mixture was extracted with ethyl acetate (200 mL×3); the organic phases were combined, dried over anhydrous sodium sulfate, and concentrated under reduced pressure to obtain 2-2. MS m/z: 183 $[M-17]^+$.

Step 2: Synthesis of Compound 2-3

2-2 (4.0 g, 19.94 mmol) and dichloromethane (50 mL) were added to a reaction flask, then Dess-Martin periodinane (10.15 g, 23.92 mmol) was added at 25° C., and the reaction was stirred at 25° C. for 2 hours. A solution of saturated sodium bicarbonate and 15% sodium sulfite (1:1) was added to the reaction mixture until both phases became clear. The mixture was allowed to stand to form two separate layers, and the aqueous phase was extracted with dichloromethane (200 mL×3); the organic phases were combined, dried over anhydrous sodium sulfate, and concentrated wider reduced pressure to obtain a crude product. The crude product was separated and purified by flash column chromatography (gradient elution: petroleum ether:ethyl acetate (V/V)=1:0-10:1) to obtain 2-3. MS m/z: 199 $[M+H]^+$.

Step 3: Synthesis of Compound 2-4

2-3 (4.0 g, 20.14 mmol) and pyridine (28 mL) were added to a reaction flask, then hydroxylamine hydrochloride (9.52 g, 136.94 mmol) was added, and the reaction was stirred at 120° C. for 3 hours. The reaction mixture was concentrated on an oil pump under reduced pressure, then 100 mL of water was added, and the resulting mixture was extracted with dichloromethane (50 mL×3); the organic phases were combined, dried over anhydrous sodium sulfate, and concentrated under reduced pressure to obtain a crude product. The crude product was separated and purified by flash column chromatography (gradient elution: petroleum ether: ethyl acetate (V/V)=1:0-10:1) to obtain purified product. 2-4 was obtained. MS m/z: 214 $[M+H]^+$, $^1H$ NMR (400 MHz, $CDCl_3$) δ ppm 11.25 (s, 1 H), 7.46 (m, 1 H), 7.23-7.31 (m, 2 H), 1.75-2.42 (m , 1 H), 0.83-0.85 (m, 1 H) 0.76-0.83 (m, 1 H), 0.57-0.58 (m, 1 H), 0.31-0.57 (m, 1 H)

Step 4: Synthesis of Compound 2-5

NaH (936.17 mg, 23.40 mmol) and tetrahydrofuran (30 mL) were added to a reaction flask, then a solution of 2-4 (2.0 g, 9.36 mmol) in N,N-dimethylformamide (5.5 mL) was added dropwise, and the reaction was stirred at 80° C. for 16 hours. To the reaction mixture was added saturated ammonium chloride (150 mL), and the resulting mixture was extracted with ethyl acetate (50 mL×3); the organic phases were combined, dried over anhydrous sodium sulfate, and concentrated under reduced pressure to obtain a crude product. The crude product was separated and purified by flash column chromatography (gradient elution: petroleum ether:ethyl acetate (V/V)=0-10:1) to obtain purified product. 2-5 was obtained. MS m/z: 194[M+H]$^+$, $^1$H NMR (400 MHz, DMSO-$d_6$) δ ppm 7.45-7.51 (m, 2 H), 7.19 (dd, J=1.2, 8.4 Hz, 1 H), 2.08-2.13 (m, 1 H), 1.08-1.14 (m, 4 H).

Step 5: Synthesis of Compound 2-6

2-5 (300 mg, 1.55 mmol) and concentrated sulfuric acid (3 mL) were added to a reaction flask, then N-bromosuccinimide (827.26 mg, 4.65 mmol) was added, and the reaction was stirred at 25° C. for 16 hours. To the reaction mixture was added 150 mL of dichloromethane, then the resulting mixture was neutralized by washing with saturated sodium bicarbonate aqueous solution until pH=7, and then extracted with dichloromethane (100 mL×3); the organic phases were combined, dried over anhydrous sodium sulfate, and concentrated under reduced pressure to obtain a crude product. The crude product was separated by flash column chromatography (gradient elution: petroleum ether: ethyl acetate (V/V)=1:0-5:1) to obtain 2-6. MS m/z: 272 [M+H]$^+$, $^1$H NMR (400 MHz, DMSO-$d_6$) δ ppm 8.40 (s, 1 H), 8.16 (s, 1 H), 2.39-2.44 (m, 1 H), 1.15-1.17 (m, 2 H), 1.09-1.11 (m, 2 H).

Step 6: Synthesis of Compound 2-7

2-6 (10 mg, 322.91 μmol), bis(pinacolato)diboron (123.00 mg, 484.36 μmol), potassium acetate (95.07 mg, 968.72 μmol), and 1,4-dioxane (6 mL) were added to a reaction flask; after the reaction system was replaced with nitrogen three times, [1,1-bis(diphenylphosphino)ferrocene] dichloropalladium dichloromethane (26.37 mg, 32.29 μmol) was added, and the reaction was stirred at 95° C. for 16 hours. The reaction mixture was filtered through celite, and 30 mL of aqueous solution was added to the filtrate, and the mixture was extracted with dichloromethane (10 mL×3); the organic phases were combined, dried over anhydrous sodium sulfate, and concentrated under reduced pressure to obtain 2-7. MS m/z: 320 [M+H]$^+$.

Step 7: Synthesis of Compound 2

2-7 (103 mg, 257.83 μmol), BB-2 (119.94 mg, 386.75 μmol), potassium carbonate (106.90 mg, 773.49 μmol), 1,4-dioxane and water (6 mL) were added to a reaction flask; after the reaction system was replaced with nitrogen three times, [1,1-bis(diphenylphosphino)ferrocene] dichloropalladium dichloromethane (21.06 mg, 25.78 μmol) was added, and the reaction was stirred at 100° C. for 3 hours. The reaction mixture was filtered through celite, and the filter cake was washed with dichloromethane (10 mL×3); the filtrate was concentrated under reduced pressure to obtain a crude product. The crude product was separated by flash column chromatography (gradient elution: petroleum ether: ethyl acetate (V/V)=1:0-1:1), and then separated and purified again by HPLC (column: Waters Xbridge 150*25 mm*5 μm; mobile phase: [water (10 mM $NH_4HCO_3$)-ACN], ACN %: 40%-70%, 12 min) to obtain compound 2. MS m/z: 423[M+H]$^+$, $^1$NMR (400 MHz, DMSO-$d_6$) δ ppm 11.61 (br s, 1 H), 9.57 (s, 1 H), 8.75 (d, J=1.2 Hz, 1 H), 8.17 (s, 1 H), 8.13 (s, 1 H), 7.40-7.44 (m, 1 H), 7.14-7.19 (m, 2 H), 2.44-2.45 (m, 1 H), 2.38 (s, 3 H), 1.14-1.20 (m, 4 H).

Embodiment 2: Preparation of Compound 3

3

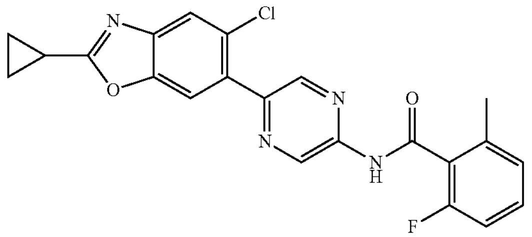

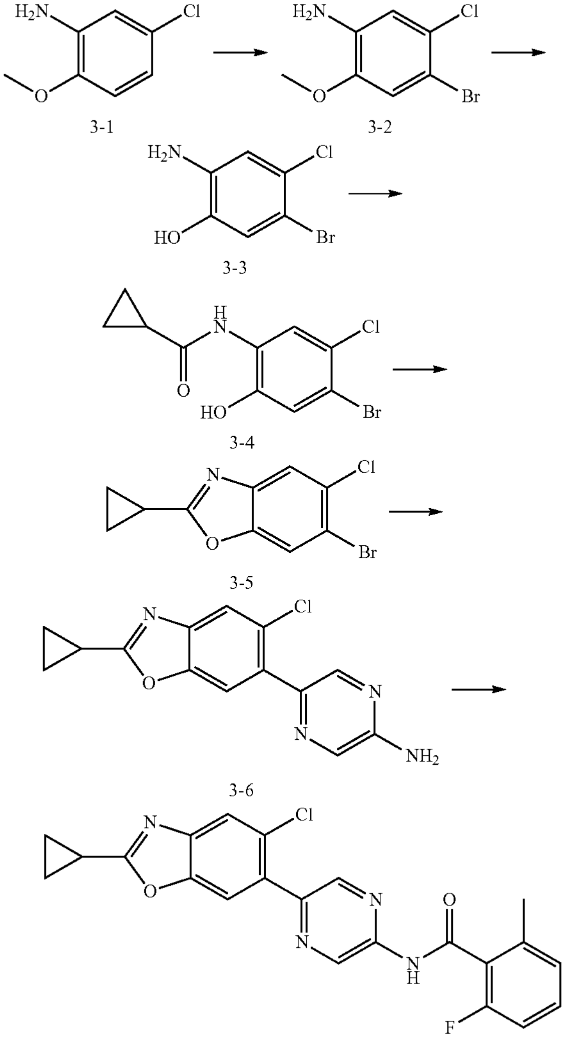

3-1

3-2

3-3

3-4

3-5

3-6

3

Step 1: Synthesis of Compound 3-2

Compound 3-1 (10 g, 63.45 mmol) and solvent acetonitrile (80 mL) were added to a reaction flask, then a solution of N-bromosuccinimide (12.42 g, 69.80 mmol) in acetonitrile (40 mL) was slowly added dropwise, and the mixture was reacted at 25° C. for 12 hours. The reaction mixture was concentrated under reduced pressure, diluted with 30 mL of water, extracted with ethyl acetate (30 mL×2), washed with 15 mL of saturated brine, dried over anhydrous sodium sulfate, and filtered; the organic phases were concentrated to obtain a crude product. The crude product was purified by flash column chromatography (petroleum ether:ethyl acetate (V/V)=5:1) to obtain compound 3-2. $^1$H NMR (400 MHz, $CDCl_3$) δ ppm 6.94 (s, 1 H), 6.78 (s, 1 H), 3.84 (s, 3 H).

Step 2: Synthesis of Compound 3-3

Compound 3-2 (5 g, 21.14 mmol) and solvent dichloromethane (50 mL) were added to a reaction flask, and a solution of boron tribromide (13.24 g, 52.86 mmol) in dichloromethane (10 mL) was added at 0° C., and the mixture was reacted at 25° C. for 12 hours. The reaction mixture was quenched with 50 mL of saturated sodium bicarbonate solution at 0° C., extracted with ethyl acetate (60 mL×3); the organic phase was washed with 30 mL of saturated brine, dried over anhydrous sodium sulfate, filtered, and concentrated to obtain compound 3-3. $^1$H NMR (400 MHz, $CDCl_3$) δ ppm 6.97 (s, 1 H), 6.84 (s, 1 H).

Step 3: Synthesis of Compound 3-4

Compound 3-3 (1 g, 4.50 mmol) and solvent tetrahydrofuran (10 mL) were added to a reaction flask, then reagents triethylamine (682.28 mg, 6.74 mmol) and cyclopropanecarbonyl chloride (704.83 mg, 6.74 mmol; were added at 0° C., and the mixture was reacted at 25° C. for 12 hours. The reaction mixture was quenched with 10 mL of water, extracted with ethyl acetate (15 mL×2), and the organic phase was washed with 15 mL of saturated brine, dried over anhydrous sodium sulfate, filtered, and concentrated to obtain a, crude product. The crude product was dissolved in methanol (15 mL) and water (5 mL), then potassium carbonate (1.08 g, 7.81 mmol) was added, and the mixture was stirred at 25° C. for 2 hours. The reaction mixture was diluted with 20 mL of water, extracted with ethyl acetate (20 mL×2), and the organic phase was washed with 20 mL of saturated brine, dried over anhydrous sodium sulfate, and filtered, and concentrated to obtain compound 3-4.

Step 4: Synthesis of compound 3-5

Compound 3-4 (0.35 g, 1.20 mmol) and solvent chloroform (10 mL) were added to a reaction flask, then phosphorus oxychloride (369.42 mg, 2.41 mmol) was added, and the mixture was reacted at 80° C. for 5 hours. The reaction was quenched with 10 mL of water, then the aqueous phase was extracted with ethyl acetate (10 mL×2); and the organic phases were combined, washed with 10 mL of saturated brine, dried over anhydrous sodium sulfate, filtered, and concentrated to obtain a crude product. The crude product was purified by silica get column chromatography (petroleum ether:ethyl acetate (V/V)=3:1) to obtain compound 3-5.

Step 5: Synthesis of Compound 3-6

Compound 3-5 (0.18 g, 0.66 mmol) and solvents 1,4-dioxane (2 mL), acetonitrile (2 mL), and water (2 mL) were added to a reaction flask, then BB-1 (175.21 mg, 0793 mmol), potassium phosphate (280.40 mg, 1.32 mmol), and dichloro bis[di-tert-butyl-(4-dimethylaminophenyl)phosphine]palladium (Aphos) (46.77 mg, 0.066 mmol) were added respectively, and the mixture was reacted at 90° C. for 6 hours. The reaction was quenched with 10 mL of water, then the aqueous phase was extracted with ethyl acetate (15 mL×2); and the organic phases were combined, washed with 10 mL of saturated brine, dried over anhydrous sodium sulfate, filtered, and concentrated to obtain a crude product. The crude product was purified by silica gel column chromatography (petroleum ether:ethyl acetate (V/V)=0:1) to obtain compound 3-6.

Step 6: Synthesis of Compound 3

Compound 3-6 (0.11 g, 0.384 mmol) and dichloromethane (3 mL) were added to a reaction flask, and reagent pyridine (60.69 mg, 0.767 mmol) was added, then 2-fluoro-6-methylbenzoyl chloride (66.21 mg, 0.383 mmol) was added dropwise, and the mixture was reacted at 25° C. for 12 hours. The reaction mixture was quenched with 10 mL of water, then the aqueous phase was extracted with ethyl acetate (10 mL×2), and the organic phases were combined, washed with 10 mL of saturated brine, dried over anhydrous sodium sulfate, filtered, and concentrated to obtain a crude product. The crude product was purified by preparative HPLC (Phenomenex Lμna. C18 100*30 mm*5 μm; mobile phase: [water (0.05% HCl)-ACN]; ACN %: 55%-80%, 10 min) to obtain compound 3. $^1$H NMR (400 MHz, $CDCl_3$) δ ppm 9.81 (s, 1 H), 8.61 (s, 1 H), 8.47 (s, 1 H), 7.73 (d, J=2.8 Hz, 2 H), 7.34 (q, J=8.0, 6.0 Hz, 1 H), 7.10 (d, J=8.0 Hz, 1 H), 7.02 (t, J=9.2 Hz, 1 H), 2.53 (s, 3 H), 2.21-2.29 (m, 1 H), 1.30-1.37 (m, 2 H) 1.22-1.28 (m, 2 H).

Embodiment 3: Preparation of Compound 4

4

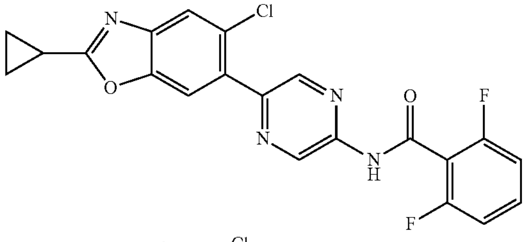

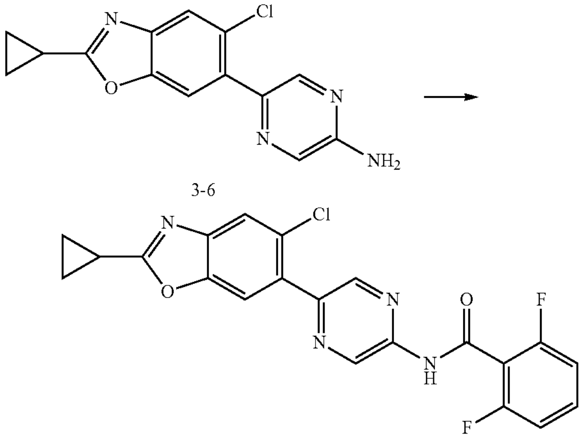

3-6

4

Step 1: Synthesis of Compound 4

Compound 3-6 (0.05 g, 0.174 mmol) and dichloromethane (3 mL) were added to a reaction flask, and reagent pyridine (27.6 mg, 0.348 mmol) was added, then 2,6-difluorobenzoyl chloride (33.87 mg, 0.192 mmol) was added dropwise, and the mixture was reacted at 25° C. for 12 hours. The reaction mixture was quenched with 10 mL of water, then the aqueous phase was extracted with ethyl acetate (10 mL×2), and the organic phases were combined, washed with 10 mL of saturated brine, dried over anhydrous sodium sulfate, filtered, and concentrated to obtain a crude product. The crude product was purified by preparative HPLC (column: Phenomenex Luna C18 150*30 mm*5 μm; mobile phase: [water (0.05% HCl)-ACN]; ACN %: 45%-70%, 10 min) to obtain compound 4. $^1$H NMR (400 MHz, $CDCl_3$) δ ppm 9.79 (s, 1 H), 8.71 (s, 1 H), 8.46 (s, 1 H), 7.73

(d, J=1.6 Hz, 2 H), 7.46-7.58 (m, 1 H), 7.07 (t, J=8.4 Hz, 2 H), 2.20-2.30 (m, 1 H), 1.30-1.37 (m, 2 H), 1.21-1.29 (m, 2 H).

Embodiment 4: Preparation of Compound 5

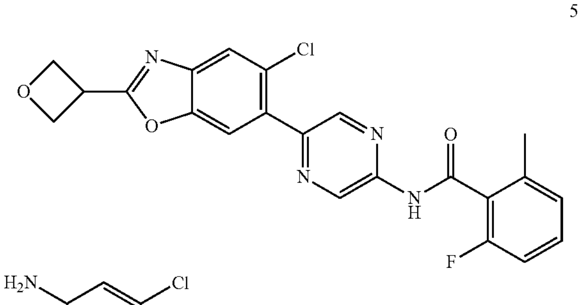

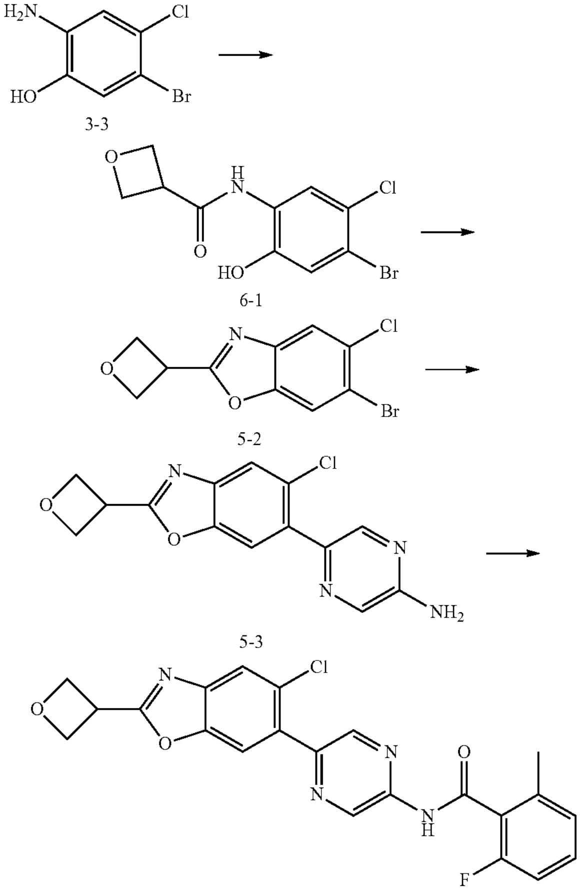

3-3

6-1

5-2

5-3

5

Step 1: Synthesis of Compound 5-1

Compound 3-3 (1.01 g, 4.52 mmol) and solvent N,N-dimethylformamide (10 mL) were added to a reaction flask, then reagents 3-oxetanecarboxylic acid (0.6 g, 5.88 mmol), N,N-diisopropylethylamine (1.17 g, 9.04 mmol) and HATU (2.58 g, 6.78 mmol) were added at 25° C. and the mixture was reacted at 25° C. for 3 hours. The reaction mixture was quenched with 10 mL, of water, extracted with ethyl acetate (15 mL×2), and the organic phase was washed with 10 mL, of saturated brine, dried over anhydrous sodium sulfate, filtered, and concentrated to obtain a crude product. The crude product was dissolved in methanol (20 mL) and water (7 mL), then potassium carbonate (1.2 g, 8.70 mmol) was added, and the mixture was stirred at 25° C. for 2 hours. The reaction mixture was adjusted to pH=4-5 with 1 mol/L hydrochloric acid, and then 10 mL of saturated sodium bicarbonate solution was added to adjust pH=7-8; the resulting mixture was diluted with 20 mL of ethyl acetate, and the phases were separated; the aqueous phase was extracted with ethyl acetate (20 mL×2), and the organic phase was washed with 20 mL of saturated brine, dried over anhydrous sodium sulfate, and filtered, and concentrated to obtain compound 5-4. $^1$H NMR (400 MHz, $CDCl_3$) δ ppm 9.40 (s, 1 H), 8.27 (s, 1 H), 7.16 (s, 1 H), 4.69-4.64 (m, 4 H), 4.18-4.11 (m, 1 H).

Step 2: Synthesis of Compound 5-2

Compound 5-1 (0.9 g, 2.94 mmol) and solvent tetrahydrofuran (15 mL) were added to a reaction flask, then triphenylphosphine (1.69 g, 6.46 mmol) and diisopropyl azodicarboxylate (1.31 g, 6.46 mmol) were added at 0° C., and the mixture was reacted at 25° C. for 3 hours. The reaction was quenched with 20 mL of $H_2O$, then the aqueous phase was extracted with ethyl acetate (30 mL×2), and the organic phases were combined, washed with 10 mL of saturated brine, dried over anhydrous sodium sulfate, filtered, and concentrated to obtain a crude product. The crude product was purified by flash column chromatography (petroleum ether:ethyl acetate (V/V)=1:1) to obtain compound 5-2.

Step 3: Synthesis of Compound 5-3

Compound 5-2 (0.45 g, 1.56 mmol) and solvents 1.4-dioxane (2 mL), acetonitrile (2 mL), and water (2 mL) were added to a reaction flask, then BB-1 (517.17 mg, 2.34 mmol), potassium phosphate (662.14 mg, 3.12 mmol), and dichloro bis[di-tert-butyl-(4-dimethylaminophenyl)phosphine] palladium (Aphos) (110.44 mg, 0.156 mmol) were added respectively, and the mixture was reacted at 90° C. for 6 hours. The reaction was quenched with 10 mL of water, then the aqueous phase was extracted with ethyl acetate (15 mL×2), and the organic phases were combined, washed with 10 mL of saturated brine, dried over anhydrous sodium sulfate, filtered, and concentrated to obtain a crude product. The crude product was purified by flash column chromatography (petroleum ether:ethyl acetate (V/V)=0:1) to obtain compound 5-3.

Step 4: Synthesis of Compound 5

Compound 5-3 (0.13 g, 0.429 mmol) and solvent pyridine (2 mL) were added to a reaction flask, then 2-fluoro-6-methylbenzoyl chloride (111.17 mg, 0.644 mmol) was added dropwise, and the mixture was reacted at 45° C. for 3 hours. The reaction mixture was quenched with 10 mL of water, then the aqueous phase was extracted with ethyl acetate (10 mL×2), and the organic phases were combined, washed with 10 mL of saturated brine, dried over anhydrous sodium sulfate, filtered, and concentrated to obtain a crude product. The crude product was purified by preparative HPLC (column: Welch Xtimate C18 150*25 mm*5 μm; mobile phase: [water (10 mM $NH_4HCO_3$)-ACN]; ACN %: 45%-65%, 10.5 min) to obtain compound 5. $^1$H NMR (400 MHz, $CDCl_3$) δ ppm 9.82 (s, 1 H), 8.61 (d, J=1.2 Hz, 1 H), 7.87 (s, 1 H), 7.84 (s, 1 H), 7.34 (q, J=8.0, 6.4 Hz, 1 H), 7.27 (s, 1 H), 7.11(d, J=7.2 Hz, 1 H), 7.02(d, J=9.2 Hz, 1 H), 5.07-5.15 (m, 4 H), 4.59 (m, 1 H), 2.53 (s, 3 H).

Embodiment 5: Preparation of Compound 6

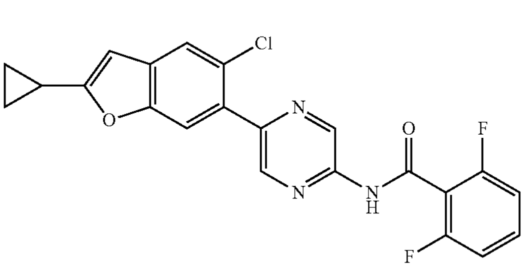

6

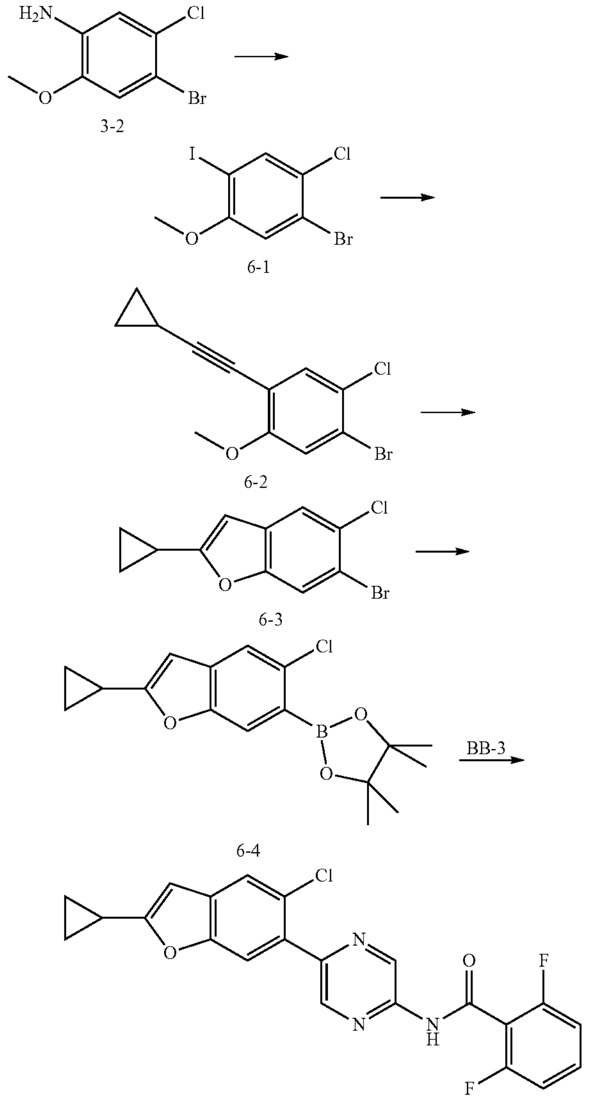

3-2

6-1

6-2

6-3

6-4

6

Step 1: Synthesis of compound 6-1

Starting material 3-2 (0.1 g, 422.84 μmol) and solvent acetonitrile (2 mL) were added to a pre-dried flask, then reagents p-toluenesulfonic acid (218.44 mg, 1.27 mmol), sodium nitrite (58.35 mg, 845.69 μmol), and potassium iodide (175.48 mg, 1.06 mmol) were added, and the mixture was stirred at 25° C. for 0.5 hours. To the system was added 10 mL of saturated sodium bicarbonate aqueous solution, then the resulting mixture was extracted with ethyl acetate (30 mL*3), and the organic phases were combined, washed with 5 mL of saturated brine, dried over anhydrous sodium sulfate, filtered, and concentrated under reduced pressure to obtain a crude product. The crude product was purified by silica gel column chromatography (petroleum ether) to obtain 6-4. $^1$H NMR (400 MHz, $CDCl_3$) δ ppm 7.75 (s, 1 H), 6.94 (s, 1 H). 3.66-3.85 (m, 3 H).

Step 2: Synthesis of compound 6-2

Starting material 6-1 (0.07 g, 201.51 mmol) and solvent diisopropylamine (2 mL) were added to a pre-dried flask, then reagents dichloro bis(triphenylphosphine) palladium (7.07 mg, 10.08 μmol), cuprous iodide (3.84 mg, 20.15 μmol), and triphenylphosphine (5.29 mg, 20.15 μmol) were added, the mixture was stirred at 25° C. for 0.5 hours; then cyclopropyl acetylene (13.32 mg, 201.51 μmol, 16.71 μL) was added, and the mixture was stirred at 70° C. for 12 hours; to the system was added 5 mL of water, and the resulting mixture was extracted with ethyl acetate (20 mL*3); the organic phases were combined, washed with 5 mL of saturated brine, dried over anhydrous sodium sulfate, filtered, and concentrated under reduced pressure to obtain a crude product. The crude product was purified by silica gel column chromatography (petroleum ether) to obtain 6-2. $^1$H NMR (400 MHz, $CDCl_3$) δ ppm 7.32 (s, 1 H), 6.99 (s, 1 H), 3.78 (s, 3 H), 1.35-1.51 (m, 1 H), 0.80-0.86 (m, 2 H), 0.73-0.79 (m, 2 H).

Step 3: Synthesis of Compound 6-3

Starting material 6-2 (0.05 g, 175.09 μmol) and anhydrous ethanol (3 mL) were added to a pre-dried microwave tube, then reagent p-toluenesulfonic acid monohydrate (33.31 mg, 175.09 μmol) was added, and the mixture was reacted under microwave irradiation at 125° C. for 1 hour, concentrated directly under reduced pressure, and purified by silica gel column chromatography (petroleum ether) to obtain 6-3. $^1$H NMR (400 MHz, $CDCl_3$) δ ppm 7.54 (s, 1 H), 7.43 (s, 1 H), 6.20 (s, 1 H), 1.84-2.01 (m, 1 H), 0.92-0.98 (m, 2 H), 0.85-0.92 (m, 2 H).

Step 4: Synthesis of Compound 6-4

Starting material 6-3 (0.1 g, 368.27 μmol), bis(pinacolato) diboron (140.28 mg, 552.41 μmol) and anhydrous dioxane (2 mL) were added to a pre-dried flask, then potassium acetate (108.43 mg, 1.10 mmol), [1,1-bis(diphenylphosphino)ferrocene] dichloropalladium dichloromethane (30.07 mg, 36.83 μmol) were added, and the mixture was stirred at 100° C. for 12 hours; to the system was added 5 mL of water, then the resulting mixture was extracted with ethyl acetate (20 mL*3), and the organic phases were combined, washed with 5 mL of saturated brine, dried over anhydrous sodium sulfate, filtered, and concentrated under reduced pressure to obtain 6-4. MS m/z: 319[M+H]$^+$.

Step 5: Synthesis of Compound 6

Starting material 6-4 (0.1 g, 313.87 μmol), BB-3 (65.72 mg, 209.25 μmol) and solvents dioxane (2 mL)/acetonitrile (1 mL)/water (0.5 mL) were added to a pre-dried flask, then reagents potassium carbonate (57.84 mg, 418.49 μmol), [1,1-bis(diphenylphosphino)ferrocene] dichloropalladium dichloromethane (17.09 mg, 20.92 μmol) were added, and the mixture was stirred at 100° C. for 2 hours; to the system was added 5 of water, then the resulting mixture was extracted with ethyl acetate (30 mL*3), and the organic phases were combined, washed with 5 mL of saturated brine, dried over anhydrous sodium sulfate, filtered, and concentrated under reduced pressure to obtain a crude product. The crude product was purified by preparative HPLC (column: Phenomenex Gemini-NX C18 75*30 mm*3 μm; mobile phase: [water (10 mM $NH_4HCO_3$)-ACN]; ACN % : 50%-80%, 10.5 min) to obtain 6. $^1$H NMR (400 MHz, $CDCl_3$) δ ppm 9.79 (s, 1 H), 8.71 (d, J=1.60 Hz, 1 H), 8.44 (br s, 1 H), 7.67 (s, 1 H), 7.58 (s, 1 H), 7.44-7.56 (m, 1 H), 7.08 (t, J=8.00 Hz, 2 H), 6.38 (s, 1 H), 2.01-2.14 (m, 1 H), 0.95-1.13 (m, 4 H). FNMR (400 MHz, $CDCl_3$) δ ppm −110.929.

Embodiment 6: Preparation of Compound 11

11

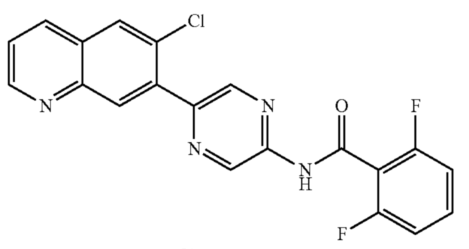

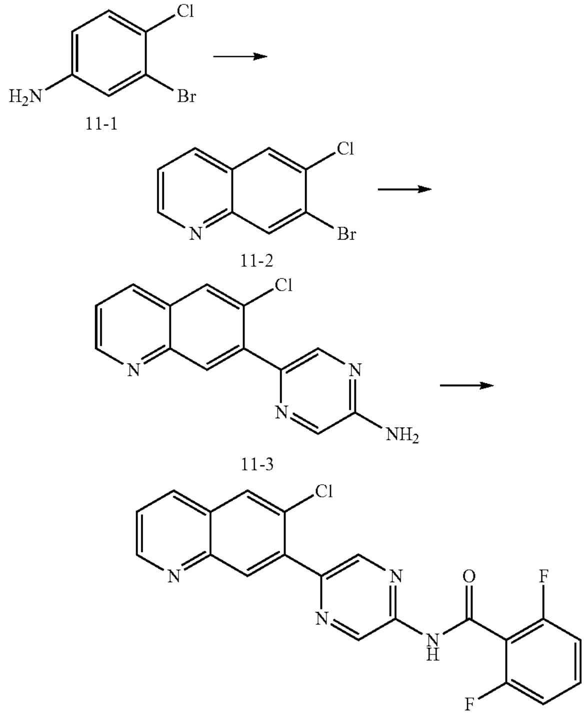

11-1

11-2

11-3

11

Step 1: Synthesis of Compound 11-2

11-1 (1 g, 4.84 mmol), acrolein acetal (1.58 g, 12.11 mmol, 1.85 mL) and hydrochloric acid (100 mL) were added to a reaction flask; after the reaction system was replaced with nitrogen three times, the reaction was stirred at 120° C. for 16 hours. The reaction mixture was adjusted to pH=9 with sodium carbonate, extracted with 3×30 mL of dichloromethane, then 15 mL of saturated brine was added, and the organic phases were combined, dried over anhydrous sodium sulfate, and concentrated under reduced pressure to obtain a crude product. The crude product was separated and purified by silica gel column chromatography (gradient elution: petroleum ether:ethyl acetate (V/V)=10:1, 3:1) to obtain compound 11-2. MS m/z: 242[M+H]$^+$; $^1$H NMR (400 MHz, $CDCl_3$) δ=8.94 (d, J=8.6, 1 H), 8.60 (d, J=8.4, 1 H), 8.04 (d, J=8.8, 1 H) 7.78 (d, J=9.2, 1 H), 7.54-7.57 (m, 1 H).

Step 2: Synthesis of Compound 11-3

11-2 (50 mg, 206.19 μmol), BB-1 (91.16 mg, 412.37 μmol), potassium carbonate (56.99 mg, 412.37 μmol), and 1,4-dioxane:water (2 mL, 4:1) were added to a reaction flask; after the reaction system was replaced with nitrogen three times, [1,1-bis(diphenylphosphino)ferrocene] dichloropalladium dichloromethane (10.10 mg, 12.37 μmol) was added, and the reaction was stirred at 90° C. for 16 hours. The reaction was filtered through celite, dried, and concentrated under reduced pressure to obtain a crude product. The crude product was separated and purified by silica gel column chromatography (gradient elution: petroleum ether: ethyl acetate (V/V)=20:1, 10:1) to obtain compound 11-3. MS m/z: 257[M+H]$^+$, $^1$H NMR (400 MHz, $CDCl_3$) δ=8.96 (d, J=2.4, 1 H), 8.42 (s, 1 H), 8.29 (s, 1 H), 8.16 (s, 1 H), 8.12 (d, J=8.8, 1 H), 7.64-7.65 (m, 2 H), 7.35 (s, 2 H).

Step 3: Synthesis of Compound 11

11-3 (30 mg, 116.87 μmol), 2,6-difluorobenzoyl chloride (41.27 mg, 233.74 μmol, 29.48 μL) and dichloromethane (2 mL) were added to a reaction flask, and the mixture was stirred, then 4-dimethylaminopyridine (1.43 mg, 11.69 μmol) was added, and the reaction was stirred at 25° C. for 16 hours. To the reaction mixture was added water (10 mL), then the resulting mixture was extracted with dichloromethane (3×10 mL), and the organic phases were combined, dried over anhydrous sodium sulfate, and concentrated under reduced pressure to obtain a crude product. The crude product was separated and purified by preparative HPLC (column: Phenomenex Luna C18 150*30 mm*5 μm mobile phase: [water (0.05% HCl)-ACN]; ACN %; 20-50%, 12 min) to obtain compound 11. MS m/z: 397[M+H]$^+$; $^1$H NMR (400 MHz, DMSO) δ ppm 11.89 (s, 1 H), 9.57 (s, 1 H), 9.08 (d, J=3.6. 1 H), 8.87 (s, 1 H), 8.58 (d, J=8.4, 1 H), 8.43 (s, 1 H), 8.36 (s, 1 H), 7.74-7.78 (m, 1 H), 7.61-7.63 (m, 1 H), 7.25-7.29 (m, 2 H).

Embodiment 7: Preparation of Compound 12

12

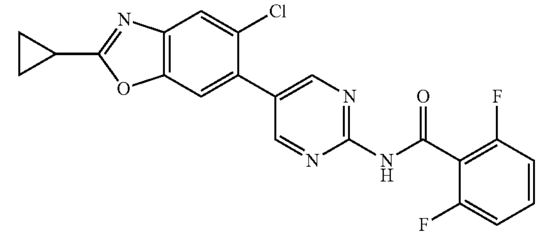

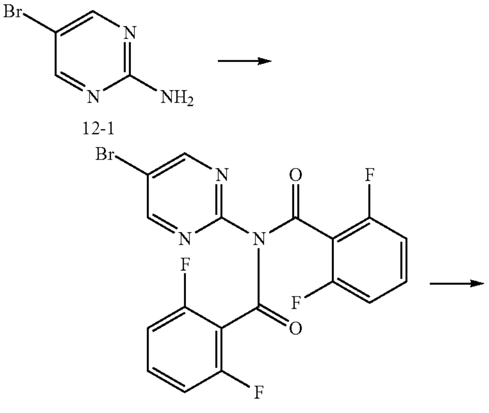

12-1

12-2

-continued

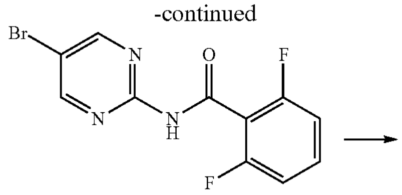

12-3

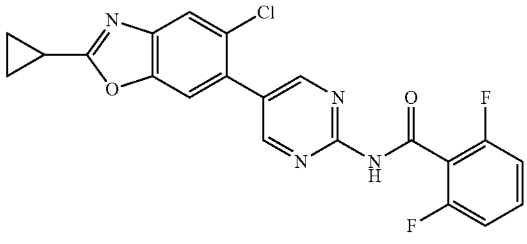

12

Step 1: Synthesis of compound 12-2

12-1 (100 mg, 574.72 μmol), 2,6-difluorobenzoyl chloride (304.39 mg, 1.72 mmol, 217.42 μL), triethylamine (290.78 mg, 2.87 mmol, 399.97 μL), and dichloromethane (1 mL) were added to a reaction flask, and the reaction was stirred at 25° C. for 16 hours. To the reaction mixture was added water (10 mL), then the mixture was allowed to stand to form two separate layers, and the aqueous phase was extracted with dichloromethane (3×10 mL), and the organic phases were combined, dried over anhydrous sodium sulfate, and concentrated under reduced pressure to obtain crude product 12-2. The product was directly used in the next step without purification. MS m/z: 454[M+H]$^+$;

Step 2: Synthesis of Compound 12-3

12-2 (10 g, 22.02 mmol), tetrahydrofuran (50 mL) and methanol solution (50 mL) were added to a reaction flask, then the mixture was stirred, and sodium hydroxide (2 M, 50.00 mL) was added, and the reaction was stirred at 25° C. for 16 hours. The reaction was concentrated and extracted with dichloromethane, and the organic phases were combined, dried over anhydrous sodium sulfate and concentrated under reduced pressure to obtain a crude product. The crude product was recrystallized with petroleum ether:ethyl acetate=1:1 to obtain compound 12-3. MS m/z: 313.9, 315.8[M+H]$^+$; $^1$H NMR (400 MHz, DMSO) δ=11.66 (s, 1 H), 8.81 (s, 2 H), 7.52-7.60 (m, 1 H), 7.17-7.21 (m, 2 H).

Step 3: Synthesis of Compound 12

12-3 (200 mg, 636.77 μmol), compound 3-5 (407.01 mg, 764.12 μmol), potassium carbonate (176.02 mg, 1.27 mmol) and 1,4-dioxane:water (4 mL, 4:1) were added to a reaction flask; after the reaction system was replaced with nitrogen three times, [1,1-bis(diphenylphosphino)ferrocene] dichloropalladium dichloromethane (52.00 mg, 63.68 μmol) was added, and the reaction was stirred at 90° C. for 16 hours. The reaction mixture was filtered through celite and concentrated under reduced pressure to obtain a crude product. The crude product was purified by silica gel column chromatography (eluent petroleum ether:ethyl acetate 20:1-10:1) to obtain a product, and the product was separated and purified by preparative HPLC (column: Welch Xtimate C18 150*25 mm*5 μm; mobile phase: [phase A-10 mM, $NH_4HCO_3$ aqueous solution; phase B-ACN] ACN %: 40%-70%, 10.5 min]) to obtain compound 12. MS m/z: 427[M+H]$^+$; $^1$H NMR (400 MHz, $CDCl_3$) δ ppm 8.71 (s, 2 H), 8.61 (s, 1 H), 7.75 (s, 1 H), 7.44-7.49 (m, 1 H), 7.39 (s, 1 H), 7.00-7.04 (m, 2 H), 2.22-2.28 (m, 1 H), 1.25-1.33 (m, 4 H).

Embodiment 8: Preparation of Compound 9

9

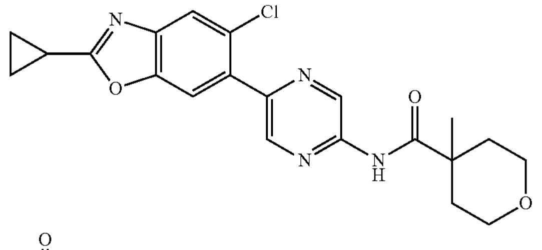

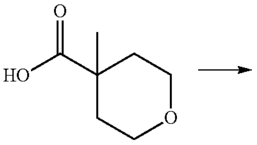

9-1

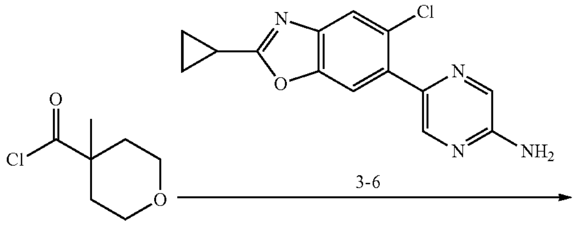

9-2

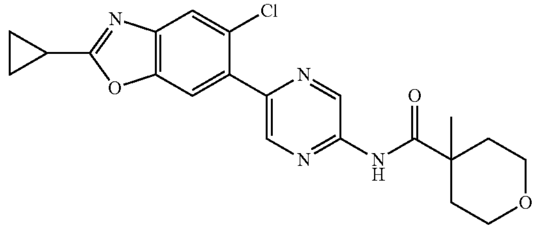

9

Step 1: Synthesis of Compound 9-2

Compound 9-1 (0.11 g, 0.763 mmol) and solvent dichloromethane (2 mL) were added to a reaction flask, then oxalyl chloride (290.54 mg, 2.29 mmol) was added dropwise, and a drop of N,N-dimethylformamide was added to catalyze the reaction, then the mixture was reacted at 25° C. for 2 hours. The reaction mixture was concentrated directly to obtain compound 9-2.

Step 2: Synthesis of Compound 9

Compound 3-6 (0.149 g, 0.520 mmol) and solvent dichloromethane (3 mL) were added to a reaction flask, then pyridine (164.64 mg, 2.08 mmol) and compound 9-2 (0.11 g, 0.676 mmol) were added dropwise, and the mixture was reacted at 25° C. for 12 hours. The reaction mixture was quenched with 10 mL of water, then the aqueous phase was extracted with ethyl acetate (10 mL×2), and the organic phases were combined, washed with 10 mL of saturated brine, dried over anhydrous sodium sulfate, filtered, and concentrated to obtain a crude product. The crude product was purified by preparative HPLC (column: Welch Xtimate C18 150*25 mm*5 μm; mobile phase: [water (10 mM $NH_4HCO_3$)-ACN]; ACN %: 40%-70%, 10.5 min) to obtain compound 9. $^1$H NMR (400 MHz, $CDCl_3$) δ ppm 9.68 (s, 1

H), 8.67 (s, 1 H), 8.02 (s, 1 H), 7.72 (s, 1 H), 7.71 (s, 1 H), 3.79-3.88 (m, 2 H), 3.72 (m, 2 H), 2.21-2.28 (m, 1 H), 2.17 (m, 2 H), 1.66-1.75 (m, 2 H), 1.42 (s, 3 H), 1.29-1.35 (m, 2 H), 1.21-1.27 (m, 2 H).

Embodiment 9: Preparation of Compound 10

10

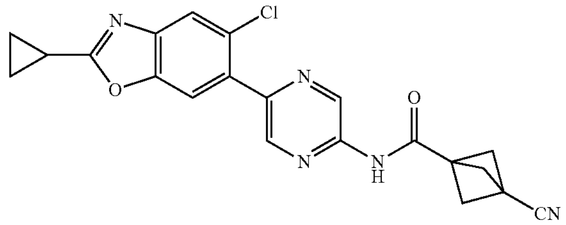

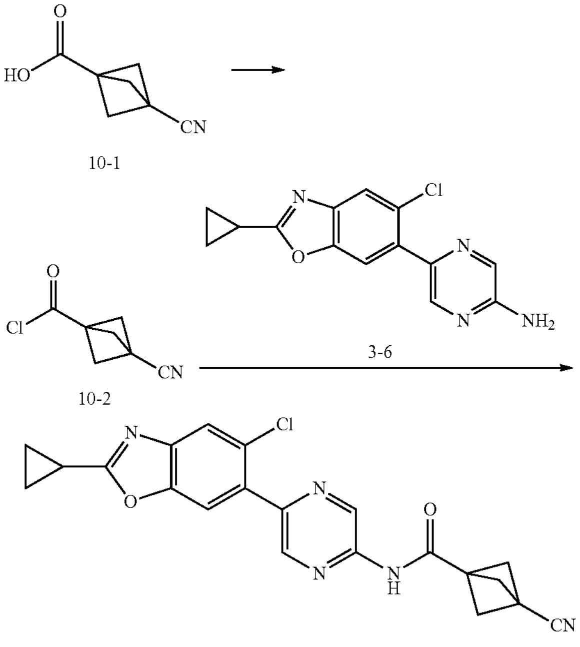

10-1

3-6

10-2

10

Step 1: Synthesis of compound 10-2

Compound 10-1 (0.03 g, 0.219 mmol) and solvent dichloromethane (2 mL) were added to a reaction flask, then thionyl chloride (65.06 mg, 0.547 mmol) was added dropwise, and a drop of N,N-dimethylformamide was added to catalyze the reaction, then the mixture was reacted at 25° C. for 2 hours. The reaction was concentrated directly to obtain compound 10-2.

Step 2: Synthesis of Compound 10

Compound 3-6 (0.046 g, 0.161 mmol) and solvent dichloromethane (2mL) were added to a reaction flask, then pyridine (50.84 mg, 0.643 mmol) and compound 7-2 (0.03 g, 0.193 mmol) were added dropwise, and the mixture was reacted at 25° C. for 12 hours. The reaction mixture was quenched with 10 mL of water, then the aqueous phase was extracted with ethyl acetate (10 mL×2), and the organic phases were combined, washed with 10 mL of saturated brine, dried over anhydrous sodium sulfate, filtered, and concentrated to obtain a crude product. The crude product was purified by preparative HPLC (column: Welch Xtimate C18 150*25 mm*5 μm; mobile phase: [water (10 mM $NH_4HCO_3$)-ACN]; ACN %: 40%-70%, 10.5 min) to obtain compound 10, [1] $^1$H NMR (400 MHz, $CDCl_3$) δ ppm 9.59 (s, 1 H), 8.70 (s, 1 H), 7.91 (s, 1 H), 7.72 (s, 1 H), 7.71 (s, 1 H), 2.66 (s, 6 H), 2.19-2.29 (m, 1 H), 1.29-1.35 (m, 2 H), 1.21 - 1.28 (m, 2 H).

Embodiment 10: Preparation of Compound 13

13

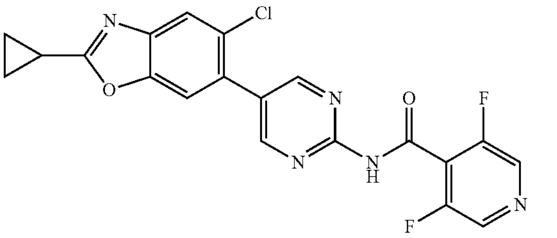

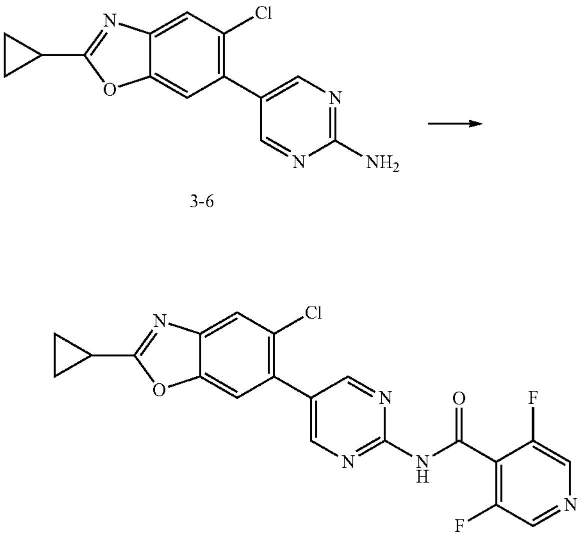

3-6

13

Step 1: Synthesis of Compound 13

Compound 3-6 (148.04 mg, 516.33 μmol), dichloromethane (3 mL) were added to a reaction flask, and reagent pyridine (163.37 mg, 2.07 mmol) was added, then 3,5-difluorobenzoyl chloride (0.11 g, 0.619 mmol) was added dropwise, and the mixture was reacted at 25° C. for 12 hours. The reaction mixture was quenched with 10 mL of water, then the aqueous phase was extracted with ethyl acetate (10 mL×2), and the organic phases were combined, washed with 10 mL of saturated brine, dried over anhydrous sodium sulfate, filtered, and concentrated to obtain a crude product. The crude product was purified by preparative HPLC (column: Welch Xtimate C18 150*25 mm*5 μm; mobile phase: [water (10 mM $NH_4HCO_3$)-ACN], ACN %: 45%-65%, 10.5 min) to obtain compound 13. $^1$H NMR (400 MHz, $CDCl_3$) δ ppm 9.75 (s, 1 H), 8.76 (d, J=1.2 Hz, 1 H), 8.57 (s, 2 H), 8.48 (s, 1 H), 7.74 (s, 2 H), 2.20-2.29 (m, 1 H), 1.31-1.36 (m, 2 H), 1.22-1.29 (m, 2 H).

Embodiment 11: Preparation of Compound 14

14

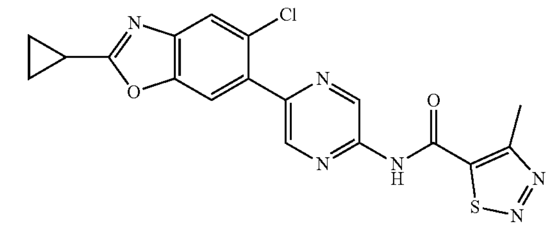

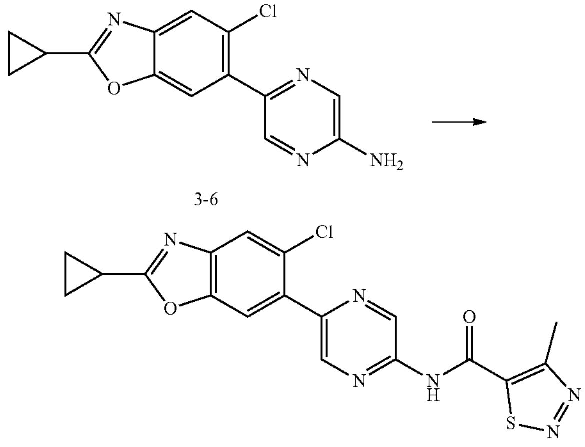

3-6

14

Step 1: Synthesis of Compound 14

Compound 3-6 (130.0 mg, 453.41 μmol), dichloromethane (2.5 mL) were added to a reaction flask, and reagent pyridine (89.66 mg, 1.13 mmol) was added, then 4-methyl-1,2,3-thiadiazole-5-carbonyl chloride (0.11 g, 0.680 mmol) was added, and the mixture was reacted at 25° C. for 3 hours. The reaction mixture was quenched with 10 mL of water, then the aqueous phase was extracted with ethyl acetate (10 mL×2), and the organic phases were combined, washed with 10 mL of saturated brine, dried over anhydrous sodium sulfate, filtered, and concentrated to obtain a crude product. The crude product was purified by preparative HPLC (neutral) to obtain compound 14, $^{1}$H NMR (400 MHz, $CDCl_3$) δ ppm 9.69 (s, 1 H), 8.76 (s, 1 H), 8.30 (s, 1 H). 7.74 (s. 2 H), 3.07 (s, 3 H), 2.21-2.31 (m, 1 H), 1.31-1.37 (m, 2 H), 1.23-1.29 (m, 2 H).

Embodiment 12: Preparation of Compound 15

15

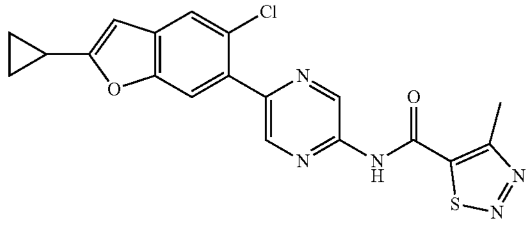

-continued

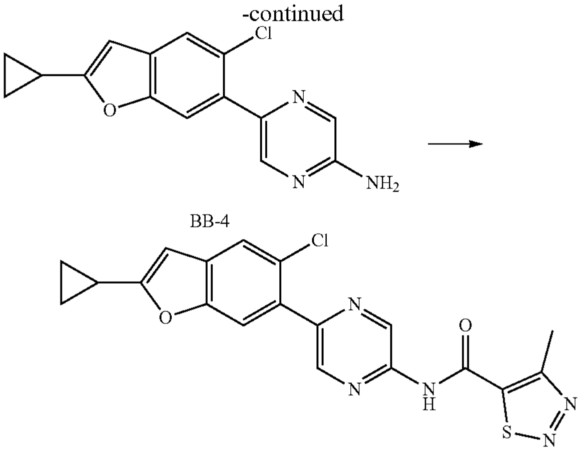

BB-4

15

Step 1: Synthesis of Compound 15

Compound BB-4 (130.0 mg, 454.98 μmol), dichloromethane (2.5 mL) were added to a reaction flask, and reagent pyridine (89.97 mg, 1.14 mmol) was added, then 4-methyl-1,2,3-thiadiazole-5-carbonyl chloride (0.11 g, 0.682 mmol) was added dropwise, and the mixture was reacted at 25° C. for 3 hours. The reaction mixture was quenched with 10 mL of water, then the aqueous phase was extracted with ethyl acetate (10 mL×2), and the organic phases were combined, washed with 10 mL of saturated brine, dried over anhydrous sodium sulfate, filtered, and concentrated to obtain a crude product. The crude product was purified by preparative HPLC (column: Phenomenex Luna C18 150*30 mm*5 μm; mobile phase: [water (0.05% HCl)-ACN]; ACN %: 45%-75%, 12 min) to obtain compound 15. $^{1}$H NMR (400 MHz, $CDCl_3$) δ ppm 9.68 (s, 1 H), 8.75 (s, 1 H), 8.26 (s. 1 H), 7.66 (s, 1 H), 7.57 (s, 1 H), 6.38 (s, 1 H), 3.07 (s, 3 H), 2.01-2.11 (m, 1 H), 1.25 (m, 1 H), 1.01-1.09 (m, 4 H).

Embodiment 13: Preparation of Compound 16

16

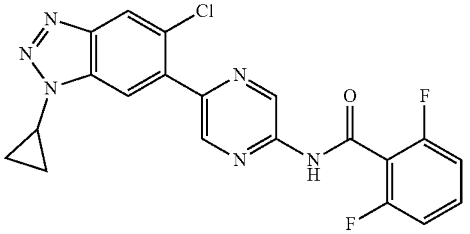

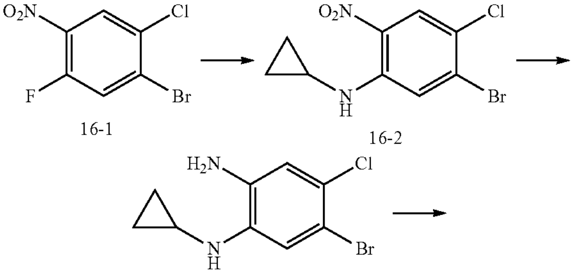

16-1

16-2

16-3

-continued

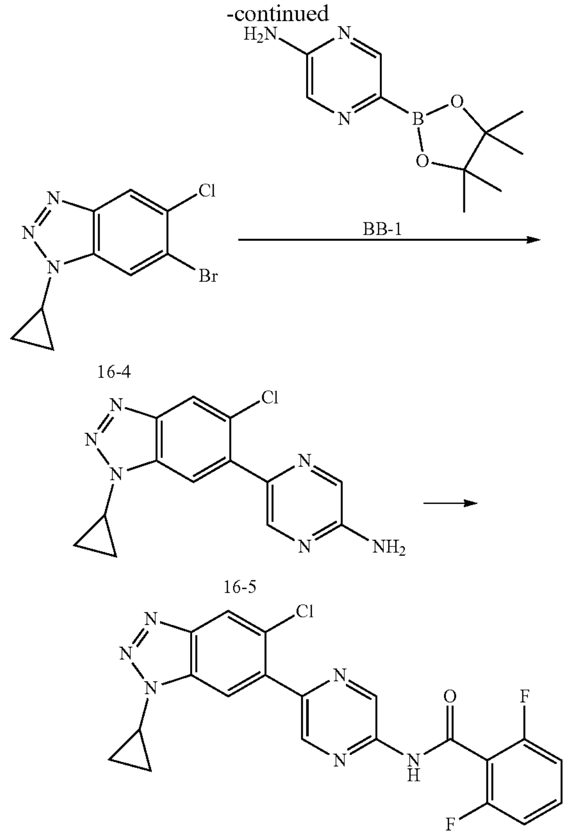

16-4

16-5

16

Step 1: Synthesis of compound 16-2

Compound 16-1 (5 g, 19.65 mmol) and solvent 1,2-dichloroethane (15 mL) were added to a reaction flask, then cyclopropylamine (2.24 g, 39.30 mmol) was added, and the mixture was reacted at 80° C. for 12 hours. The reaction mixture was diluted with 20 mL of water, extracted with ethyl acetate (30 mL×3), and the organic phase was washed with saturated brine (20 mL), dried over anhydrous sodium sulfate, filtered, concentrated to obtain compound 16-2. MS m/z: 291, 293 $[M+H]^+$.

$^1$NMR (400 MHz, $CDCl_3$) δ ppm 8.25 (s, 1 H), 7.98 (br s, 1 H), 7.63 (s. 1 H), 2.54-2.61 (m. 1 H), 0.94-1.01 (m, 2 H), 0.66-0.72 (m, 2 H).

Step 2: Synthesis of compound 16-3

Compound 16-2 (1.1 g, 3.77 mmol) and solvents ethanol (10 mL) and water (2 mL) were added to a reaction flask, then reagents ammonium chloride (807.32 mg, 15.09 mmol) and iron powder (842.94 mg, 15.09 mmol) were added, and the mixture was reacted at 80° C. for 2 hours. The reaction mixture was filtered through celite, then the filtrate was extracted with ethyl acetate (30 mL×3), and the organic phase was washed with saturated brine (10 mL), dried over anhydrous sodium sulfate, filtered, and concentrated to obtain compound 16-3. MS m/z: 261, 263 $[M+H]^+$.

Step 3: Synthesis of Compound 16-4

Compound 16-3 (0.6 g, 2.29 mmol) and solvent glacial acetic acid (15 mL) were added to a reaction flask, then reagent sodium nitrite (237.43 mg, 3.44 mmol) was added, and the mixture was reacted at 25° C. for 12 hours. The reaction mixture was diluted with water (10 mL), and the resulting mixture was extracted with ethyl acetate (20 mL×2). The organic phase was washed with saturated sodium bicarbonate solution (15 mL) and saturated brine (15 mL) respectively, dried over anhydrous sodium sulfate, filtered, and concentrated to obtain compound 16-4. MS m/z: 272, 274 $[M+H]^+$. $^1$H NMR (400 MHz, $CDCl_3$) δ ppm 8.17(s, 1 H), 8.02(s, 1 H), 3.72-3.78(m, 1 H), 1.33-1.38(m, 4 H).

Step 4: Synthesis of Compound 16-5

Compound 16-4 (973.39 mg, 4.40 mmol), BB-1 (0.6 g, 2.20 mmol) and solvents tetrahydrofuran (16 mL) and water (4 mL) were added to a reaction flask, then reagent potassium phosphate (1.17 g, 5.50 mmol) and catalyst [1,1-bis (di-tert-butylphosphino)ferrocene] dichloropalladium (II) (215.23 mg, 330.24 μmol) were added wider the protection of nitrogen, and the mixture was reacted at 85° C. for 12 hours. The reaction mixture was filtered off the catalyst through celite, then the filtrate was extracted with ethyl acetate (100 mL×2), and the organic phase was washed with saturated brine (100 mL), dried over anhydrous sodium sulfate, filtered, and concentrated to obtain compound 16-5. MS m/z: 287, 289 $[M+H]^+$. $^1$H NMR (400 MHz, $CDCl_3$) δ ppm 8.18 (s, 1 H), 8.13 (s, 1 H), 8.01, (s, 2 H), 7.92 (s, 1 H), 7.87 (s, 1 H), 3.76-3.81 (m, 1 H), 1.38-1.44 (m, 2 H), 1.24-1.35 (m, 2 H).

Step 5: Synthesis of Compound 16

Compound 16-5 (0.1 g, 348.77 μmol) and solvent dichloromethane (2 mL) were added to a reaction flask then reagents pyridine (98.00 mg, 1.24 mmol) and 2,6-difluorobenzoyl chloride (98.00 mg, 555.09 μmol) were added, and the mixture was reacted at 25° C. for 12 hours. The reaction mixture was diluted with water (20 mL), and the resulting mixture was extracted with ethyl acetate (25 mL×2), and the organic phase was washed with saturated brine (15 mL), dried over anhydrous sodium sulfate, filtered, and concentrated to obtain a crude product. The crude product was purified by preparative HPLC (column: Waters Xbridge Prep OBD C18 150*40 mm*10 μm; mobile phase: [water (10 mM $NH_4HCO_3$)-ACN]; ACN %: 40%-60%, 8 min) to obtain compound 16. MS m/z: 426, 428 $[M+H]^+$. $^1$H NMR (400 MHz, CDCl3) δ ppm 9.84 (s, 1 H), 8.76 (s, 1 H), 8.46 (s, 1 H), 8.22 (s, 1 H), 7.98 (s, 1 H), 7.48-7.57 (m, 1 H), 7.09 (t, J=8.40 Hz, 2 H), 3.83 (m, 1 H), 1.40-1.47 (m, 2H). 1.31-1.39 (m, 2 H).

Embodiment 14: Preparation of Compound 17

17

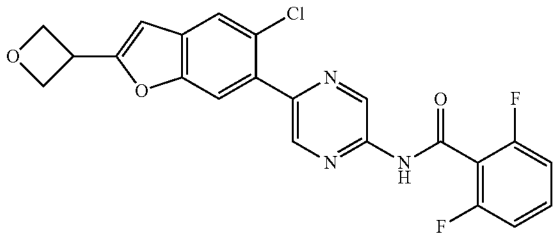

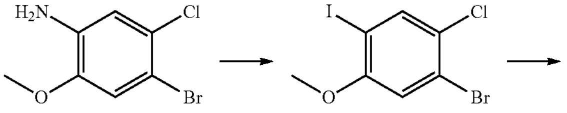

17-1

17-2

-continued

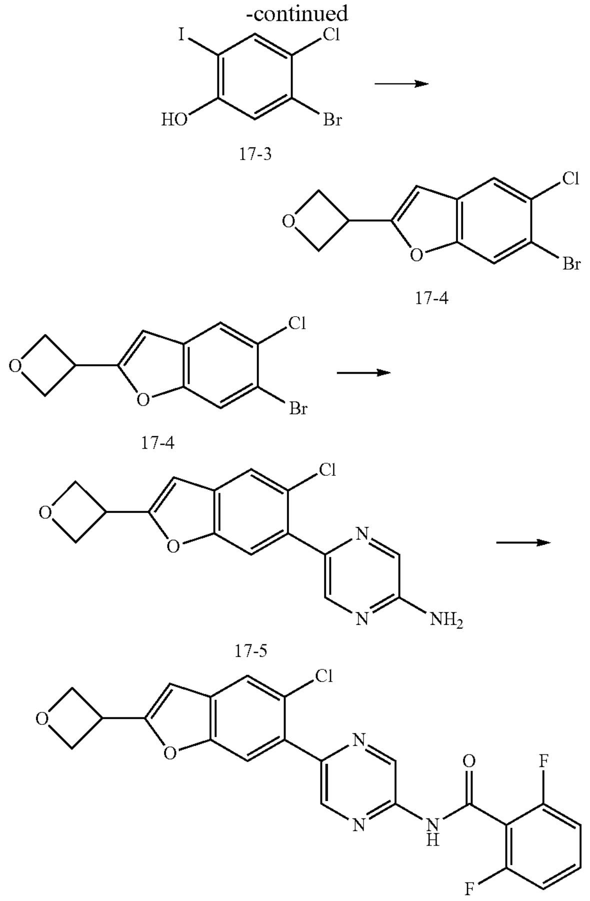

17-3

17-4

17-4

17-5

17

Step 1: Synthesis of Compound 17-2

Starting material 17-1 (25 g, 105.71 mmol) and solvent acetonitrile (250 mL) were added to a pre-dried flask, then reagents text-butyl nitrite (32.70 g, 317.13 mmol, 37.72 mL), and copper iodide (40.27 g, 211.42 mmol) were added. The reaction mixture was stirred for at 60° C. 12 hours and filtered through celite, and the mother liquor was diluted with water (200 mL), and the resulting mixture was extracted with ethyl acetate (50 mL×3); the organic phases were combined, dried over anhydrous sodium sulfate, filtered, and concentrated to obtain a crude product of compound 17-2.

Step 2: Synthesis of Compound 17-3

The substrate compound 17-2 (3.5 g, 10.08 mmol) and boron tribromide (7.57 g, 30.23 mmol, 2.91 mL) were dissolved in dichloromethane (70 mL), and the mixture was stirred at 50° C. for 12 hours. The reaction was directly diluted with water (200 mL), extracted with ethyl acetate (50 mL), dried over anhydrous sodium sulfate, filtered, and concentrated to obtain a product of compound 17-3.

Step 3: Synthesis of Compound 17-4

Compound 17-3 (406.03 mg, 1.22 mmol), 3-ethynyloxetane (0.08 g, 974.42 μmol), and diisopropylamine (1.18 g, 11.69 mmol, 1.65 mL) were dissolved in toluene (5 mL). To the reaction system were added copper iodide (92.79 mg, 487.21 μmol) and dichloro bis(triphenylphosphine) palladium (II) (102.59 mg, 146.16 μmol), and the mixture was stirred at 80° C. for 12 hours. The reaction was diluted with water (30 mL), extracted with ethyl acetate (15 mL×3), dried over anhydrous sodium sulfate, filtered, and concentrated to obtain a product of compound 17-4.

Step 4: Synthesis of Compound 17-5

Compound 17-4 (0.4 g, 1.39 mmol) and compound BB-1 (615.05 mg, 2.78 mmol) were dissolved in tetrahydrofuran (15 mL) and water (3 mL), and the system was replaced with nitrogen. To the system were added potassium phosphate (738.24 mg, 3.48 mmol) and 1,1-bis(tert-butylphosphino) ferrocene palladium chloride (136.00 mg, 208.67 μmol), and the reaction was stirred at 85° C. for 12 hours. The reaction was diluted with water (40 mL), extracted with ethyl acetate (20 mL×3), and the organic phase was dried over anhydrous sodium sulfate, filtered, and concentrated to obtain a product of compound 17-5.

Step 5: Synthesis of Compound 17

Compound 17-5 (0.19 g, 629.71 μmol) was dissolved in pyridine (3 mL), to the reaction system was added 2,6-difluorobenzoyl chloride (166.76 mg, 944.56 μmol) at 0° C., and the mixture was stirred at 15° C. for 8 hours. The reaction mixture was diluted with water (30 mL), and the resulting mixture was extracted with ethyl acetate (10 mL×3); the organic phase was dried over anhydrous sodium sulfate, filtered, and concentrated to obtain a crude product. The crude product was separated and purified by silica gel column chromatography (eluent: petroleum ether:ethyl acetate=20:1-1:1) to obtain product 17.

$^1$H NMR (400 MHz, DMSO-$d_6$) δ ppm 11.73-11.81 (m, 1 H), 9.48 (br s, 1 H), 8.72 (s, 1 H), 7.85 (s, 1 H), 7.83 (s, 1 H), 7.55-7.63 (m, 1 H), 7.20-7.27 (m, 2 H), 6.92 (s, 1 H), 4.87-4.95 (m, 2 H), 4.75 (t, J=6.36 Hz, 2 H), 4.46-4.56 (m, 1 H).

Embodiment 15: Preparation of Compound 18

18

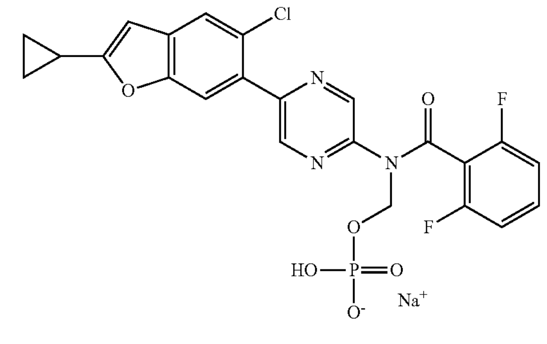

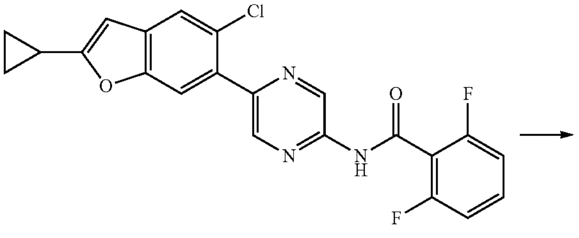

6

-continued

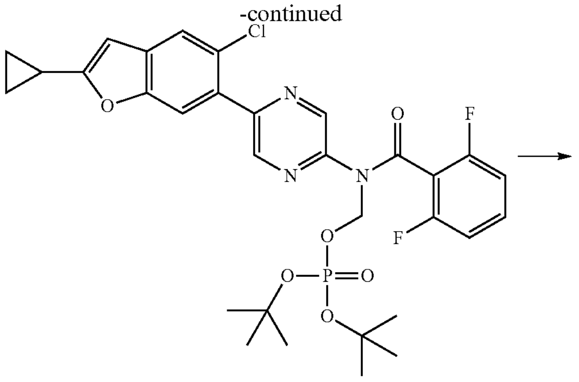

18-2

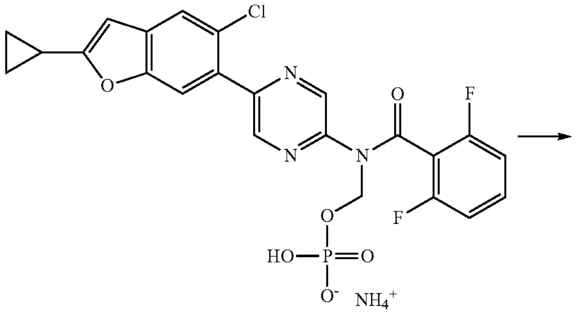

18-3

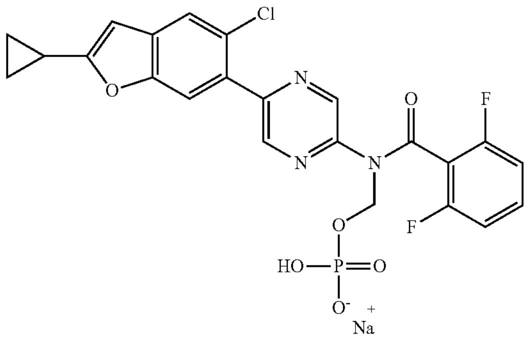

18

Step 1: Synthesis of Compound 18-2

Di-tert-butyl chloromethyl phosphate (36.45 mg, 140.91 μmol) and compound 6 (0.05 g, 117.42 μmol) were dissolved in DMF (0.5 mL), to the reaction system was added KOH (9.22 mg, 164.39 μmol), and the mixture was stirred at room temperature 25° C. for 24 hours. The reaction was cooled, diluted with water (10 mL) and saturated brine (10 mL), and the resulting mixture was extracted with ethyl acetate (10 mL×3); the organic phase was dried over anhydrous sodium sulfate, filtered, and concentrated to obtain product 18-2. MS m/z: 438[M−210]$^+$, 536[M−112]$^+$, 648 [M+H]$^+$. $^1$H NMR (400 MHz, $CDCl_3$) δ ppm 9.67-9.72 (m, 1 H), 8.98 (br s, 1 H), 8.44 (s, 1 H), 7.54 (s, 1 H), 7.45-7.47 (m, 1 H), 7.30-7.40 (m, 1 H), 6.94 (t, J=8.32 Hz, 2 H), 6.28 (s, 1 H), 5.56 (d, J=15.01 Hz, 2 H), 1.94-2.01 (m, 1 H), 1.43 (s, 18 H), 0.95 (br dd, J=5.50, 1.75 Hz, 4 H), Step 2: Synthesis of Compound 18-3

Compound 18-2 (0.1 g, 154.31 μmol) was dissolved in MeOH (0.51 mL) and glacial acetic acid (0.05 mL), to the reaction was added a solution of sodium acetate in acetic acid (1 M, 925.88 μL), and the reaction was stirred at 75° C. for 16 hours. The reaction mixture was diluted with 10 mL of water, and the resulting mixture was extracted with ethyl acetate (5 mL×4); the organic phase was dried, and concentrated to obtain a crude product. The crude product was purified by (preparative HPLC: chromatographic column: Phenomenex Gemini-NX 150*30 mm*5 μm; mobile phase: [$H_2O$ (10 mM $NH_4HCO_3$)-ACN]; ACN %: 20%-50%, 10 min) to obtain 18-3. MS m/z: 438[M+H−98]$^+$, 536[M+H]$^+$, $^1$H NMR (400 MHz, DMSO-$d_6$) δ ppm 8.83-9.01 (m, 1 H) 8.51-8.71 (m, 1 H) 7.66-7.78 (m, 2 H) 7.45-7.55 (m, 1 H) 7.11 (br s. 2 H) 6.66 (s, 1 H) 5.56 (br s, 2 H) 2.12-2.25 (m, 1 H) 1.03-1.12 (m, 2 H) 0.93-1.01 (m, 2 H).

Step 3: Synthesis of Compound 18

The Dowex50WX8-100 cation exchange hydrogen resin was placed in a glass preparation column with a diameter of 3 cm and a height of about 5 cm. a 1N HCl solution (100 mL) prepared with deionized water in advance was added slowly to the column to rinse over the entire resin layer slowly. The resin layer was then rinsed to neutral with deionized water. Then, 1 N NaOH solution (100 mL) prepared with deionized water in advance was slowly poured into the column to over the entire resin layer slowly. The resin layer was then rinsed to neutral with deionized water. The above operation was repeated once to obtain a sodium ion exchange resin, 18-3 was dissolved in deionized water (5 mL), then the prepared sodium ion resin was slowly poured into the mixture, and rinsed with deionized water (100 mL) to obtain compound 18. MS m/z: 438[M+H−98]$^+$, 536[M+H]$^+$, H NMR (400 MHz, $CD_3OD$) δ ppm 8.50-9.08 (m, 2 H), 7.56-7.71 (m, 2 H), 7.34-7.54 (m, 1 H), 6.85-7.17 (m, 2 H), 6.46-6.58 (m, 1 H), 5.72-5.93 (m, 2 H), 2.04-2.20 (m, 1 H), 0.93-1.17 (m, 4 H).

Embodiment 16: Preparation of Compound 19

16

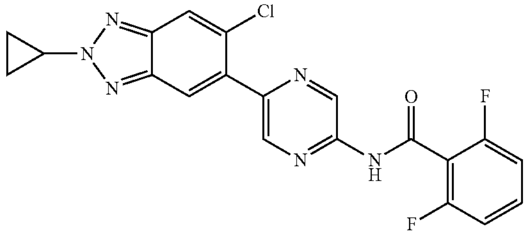

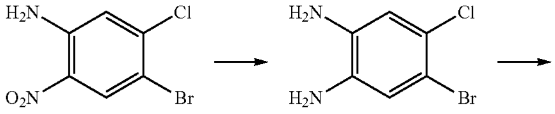

3-3 19-2

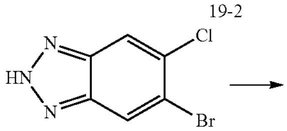

19-3

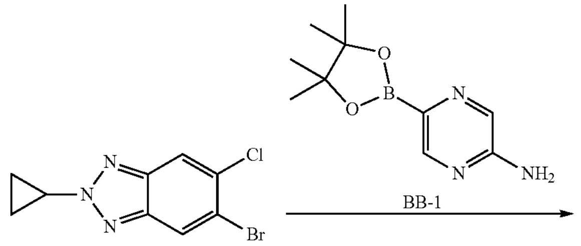

19-4

-continued

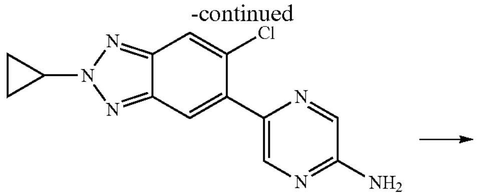

19-5

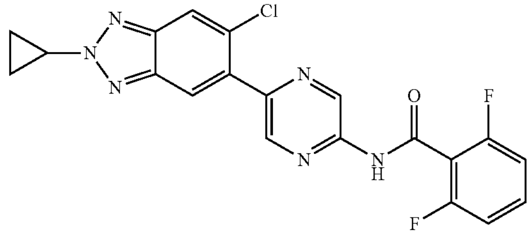

19

Step 1: Synthesis of Compound 19-2

Compound 3-3 (4 g, 15.91 mmol) and solvents ethanol (40 mL) and water (8 mL) were added to a reaction flask, then ammonium chloride (3.40 g, 63.63 mmol) and iron powder (3.55 g, 63.63 mmol) were added, and the mixture was reacted at 80° C. for 2 hours. The reaction mixture was filtered through celite, and the filtrate was concentrated on a water pump to remove most of the solvent; 50 mL of ethyl acetate and 30 mL of water were added, then the phases were separated, and the aqueous phase was extracted with ethyl acetate (50 mL×2); the organic phase was washed with saturated brine (50 mL), dried over anhydrous sodium sulfate, filtered, and concentrated to obtain compound 19-2. MS m/z: 221, 223 $[M+H]^+$.

$^1H$ NMR (400 MHz, DMSO-$d_6$) δ: 6.75 (s, 1 H), 6.65 (s, 1 H), 4.90 (s, 2 H), 4.86 (s, 2 H).

Step 2: Synthesis of Compound 19-3

Compound 19-2 (0.5 g, 2.26 mmol) and solvents acetic acid (6 mL) and water (2 mL) were added to a reaction flask, then an aqueous solution (1 mL) of sodium nitrite (233.65 mg, 3.39 mmol) was added at 0° C., and the mixture was reacted at 25° C. for 12 hours. The reaction was filtered directly, and the filter cake was washed with water (5 mL×2), and evaporated to dryness by rotary evaporation on a water pump to obtain compound 19-3. MS m/z: 232, 234 $[M+H]^+$. $^1H$ NMR (400 MHz, DMSO-$d_6$) δ: 8.46 (s, 1 H), 8.31 (s, 1 H).

Step 3: Synthesis of compound 19-4

Compound 19-3 (0.2 g, 860.34 μmol) and solvent 1,2-dichloroethane (2 mL) were added to a reaction flask, then cyclopropylboronic acid (147.80 mg, 1.72 mmol), copper acetate (156.26 mg, 860.34 μmol), 2,2-bipyridine (134.37 mg, 860.34 μmol), and sodium carbonate (182.38 mg, 1.72 mmol) were added, and the mixture was reacted at 80° C. for 12 hours. The reaction mixture was diluted with water (10 mL), and the resulting mixture was extracted with ethyl acetate (20 mL×2); and the organic phase was washed with saturated brine (20 mL), dried over anhydrous sodium sulfate, filtered, and concentrated to obtain compound 19-4. MS m/z: 272, 274 $[M+H]^+$. $^1H$ NMR (400 MHz, $CDCl_3$) δ: 8.16 (s, 1 H), 7.98 (s, 1 H), 4.34-4.41 (m, 1 H), 1.60-1.62 (m, 2 H), 1.27-1.32 (m, 2 H).

Step 4: Synthesis of Compound 19-5

Compound 19-4 (0.1 g, 366.93 μmol), BB-1 (0.16 g, 0.73 mmol), and solvents tetrahydrofuran (4 mL) and water (1 mL) were added to a reaction flask, then reagents potassium phosphate (0.19 g, 0.92 mmol) and catalyst [1,1-bis(di-tert-butylphosphino)ferrocene] dichloropalladium (II) (35.88 mg, 55.05 μmol) were added under the production of nitrogen, and the mixture was reacted at 85° C. for 12 hours. The reaction mixture was filtered off the catalyst through celite, then the filtrate was extracted with ethyl acetate (20 mL×2), and the organic phase was washed with saturated brine (20 mL), dried over anhydrous sodium sulfate, filtered, and concentrated to obtain compound 19-5. MS m/z: 287, 289 $[M+H]^+$. $^1H$ NMR (400 MHz, $CDCl_3$) δ: 8.31 (s, 1 H), 8.13 (s, 1 H), 7.97 (s, 1 H), 7.96 (s. 1 H), 4.77 (s, 2 H), 4.37-4.42 (m, 1 H), 1.62-1.66 (m, 2 H), 1.29-1.33 (m, 2 H).

Step 5: Synthesis of compound 19

Compound 19-5 (0.08 g, 279.02 μmol) and solvent dichloromethane (2 mL) were added to a reaction flask, then reagents pyridine (55.18 mg, 0.70 mmol) and 2,6-difluorobenzoyl chloride (73.89 mg, 418.53 μmol) were added, and the mixture was reacted at 25° C. for 12 hours. The reaction mixture was diluted with water (20 mL), the resulting mixture was extracted with ethyl acetate (25 mL×2), and the organic phase was washed with saturated brine (15 mL), dried over anhydrous sodium sulfate, filtered, and concentrated to obtain a crude product. The crude product was purified by preparative HPLC (column: Kromasil C18 (250*50 mm*10 μm; mobile phase: [water (10 mM $NH_4HCO_3$)-ACN]; ACN %: 20%-50%, 10 min) to obtain compound 19. MS m/z: 427 $[M+H]^+$. $^1H$ NMR (400 MHz, $CDCl_3$) δ: 9.81 (s, 1 H), 8.63 (s, 1 H), 8.44 (s, 1 H), 8.07 (s, 1 H), 8.01 (s, 1 H), 7.47-7.56 (m, 1 H), 7.08 (t, J=8.4 Hz, 2 H), 4.40-4.45 (m, 1 H), 1.62-1.68 (m, 2 H), 1.28-1.36 (m, 2 H).

Embodiment 17: Preparation of Compound 20

20

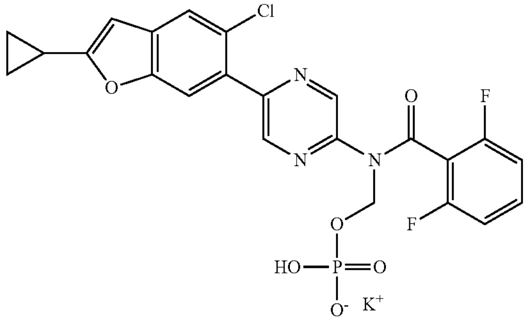

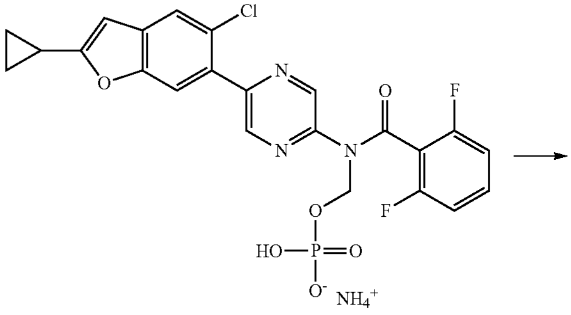

18-3

-continued

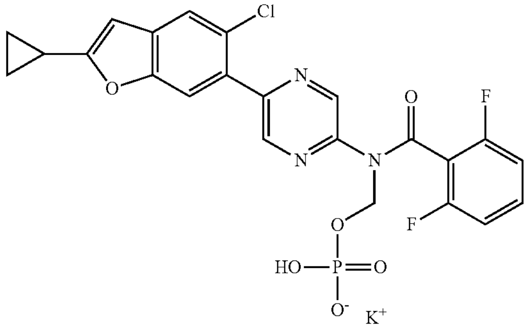

20

Step 1: Synthesis of Compound 20

Potassium ion exchange resin was prepared firstly: the Dowex50WX8-100 cation exchange hydrogen resin was placed in a glass preparative column with a diameter 3 cm and a height of about 5 cm, then a 1N HCl solution (100 mL) prepared with deionized water in advance was slowly added to the column to rinse over the entire resin layer slowly. The resin layer was then rinsed to neutral with deionized water. Then, 1 N KOH solution (100 mL) prepared with deionized water in advance was slowly poured into the column to rinse over the entire resin layer slowly. The resin layer was then rinsed to neutral with deionized water. This operation was repeated once to obtain a potassium ion exchange resin. 30 mg of 18-3 was dissolved in deionized water (5 mL) and treated with the potassium ion exchange resin prepared above-mentioned to obtain compound 20. MS m/z: 438[M+H-98]$^+$, 536[M+H]$^+$, $^1$H NMR (400 MHz, DMSO-$d_6$) δ ppm 8.94 (s, 1 H) 8.48-8.66 (m, 1 H) 7.71 (br s, 2 H) 7.43-7.55 (m, 1 H) 7.01-7.17 (m, 2 H) 6.59-6.71 (m, 1 H) 5.44-5.61 (m, 2 H) 2.11-2.23 (m, 1 H) 1.02-1.10 (m, 2 H) 0.87-0.99 (m, 2 H).

Embodiment 18: Preparation of Compound 21

21

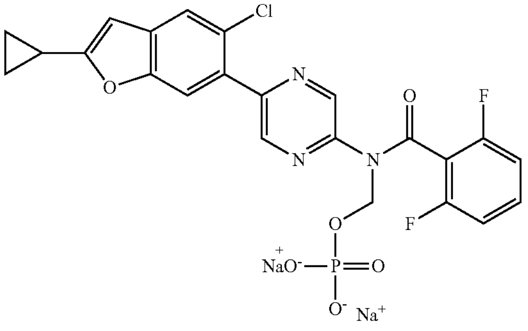

-continued

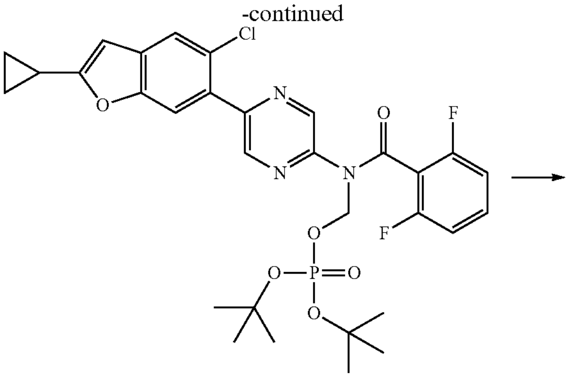

18-2

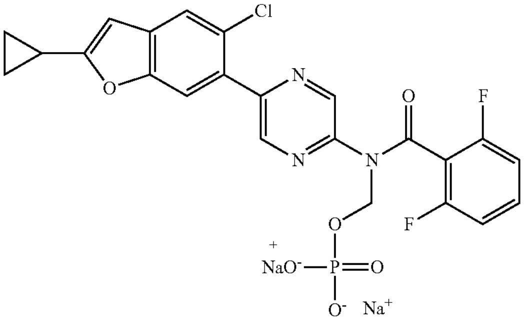

21

Step 1: Synthesis of Compound 21

Compound 18-2 (1 g, 1.59 mmol, 1 eq) was dissolved in 27 mL of a mixed solvent of acetic acid, acetonitrile, and water (acetic acid:acetonitrile:water=7:10:10), then the mixture was stirred at 40° C. for 16 hours, and 100 mL of ethyl acetate and 100 mL of water were added to the reaction mixture; the phases were separated, and the organic phase was obtained; 50 mL of 1N NaOH solution was added, then the phases were separated, and the aqueous phase was obtained. The aqueous phase was acidified to pH=5-6 with 1N HCl, extracted with 30 mL of fresh ethyl acetate, and the organic phase was evaporated to dryness by rotary evaporation to obtain a residue. The residue was dissolved in 10 mL of ethyl acetate, then 2 mL of sodium hydroxide aqueous solution (140 mg, 2.2 eq) was added to carefully separate the aqueous phase; 40 mL of isopropanol was added to mix well, and the mixture was stood at 0° C. for 24 hours, filtered, then the filter cake was washed with 2 mL of isopropanol, and dried to obtain compound 21. MS m/z: 438[M+H-98]$^+$, 536[M+H]$^+$. $^1$H NMR (400 MHz, $D_2O$) δ ppm 8.69 (br s, 1 H) 8.35 (br s, 1 H) 7.19 (br s, 1 H) 7.06-7.15 (m, 1 H) 6.92-7.06 (m, 1 H) 6.60-6.88 (m, 2 H) 5.97 (br s, 1 H) 5.55 (br s, 2 H) 1.78 (br s, 1 H) 0.82 (br d, J=7.45 Hz, 2 H) 0.46-0.74 (m, 2 H).

Embodiment 19: Preparation of Compound 22

22

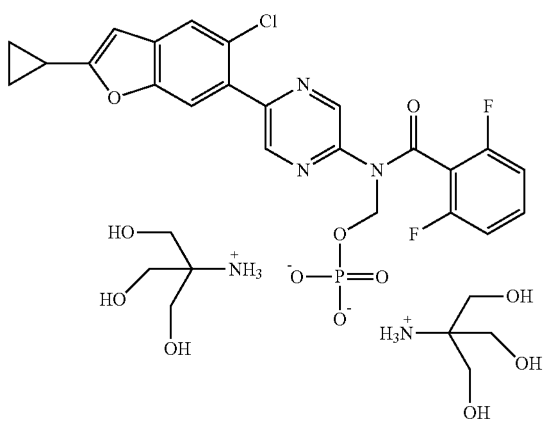

-continued

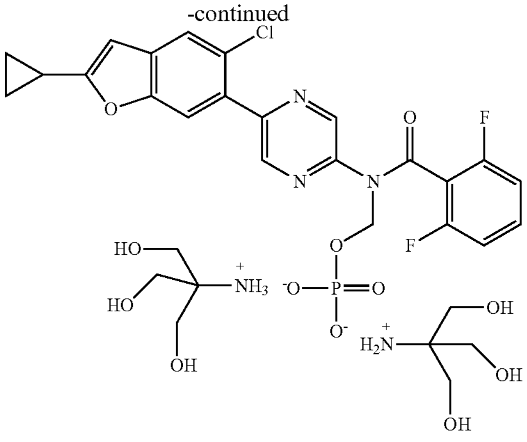

22

Synthetic Route:

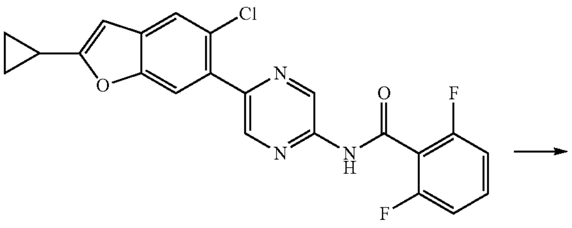

6

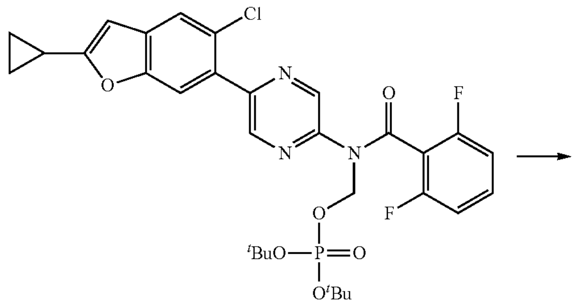

18-2

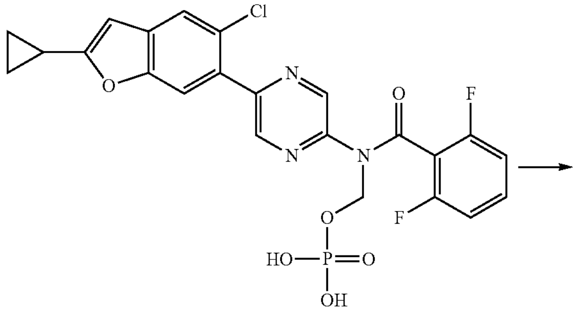

22-1

Step 1: Synthesis of Compound 18-2

To the reaction mixture were added starting compound 6 (24.7 g, 58.01 mmol) and N,N-dimethylacetamide (250 mL), then di-tert-butyl chloromethyl phosphate (37.51 g, 145.02 mmol), cesium carbonate (47.25 g, 145.02 mmol), and potassium iodide (962.91 mg, 5.80 mmol) were added sequentially, and the reaction was stirred at 40° C. for 16 hours. To the reaction mixture were added 2000 mL of water and 300 mL of ethyl acetate; after stirring for 3 hours, the reaction mixture was extracted with ethyl acetate (300 mL×3); the organic phases were combined, dried over anhydrous sodium sulfate, and concentrated under reduced pressure to obtain a crude product. The crude product was recrystallized with dichloromethane and n-heptane (dichloromethane:n-heptane=1:6, 600 mL) and concentrated under reduced pressure to obtain a crude product, which was slurried with ethyl acetate and n-heptane (ethyl acetate:n-heptane=1:5, 100 mL) and filtered, and the filter cake was washed with ethyl acetate and n-heptane (ethyl acetate:n-heptane=1:5), and then the filter cake was collected to remove the residual solvent under vacuum to obtain compound 18-2. MS m/z: 438 $[M-\mathbf{209}]^+$.

Step 2: Synthesis of Compound 22-1

Compound 18-2 (2.0 g, 3.09 mmol) and acetonitrile (10 mL) were added to a reaction flask, then a buffer solution of disodium hydrogen phosphate and citric acid (pH=3, 10 mL) was added, and the reaction mixture was stirred at 50° C. for 16 hours. The reaction mixture was filtered after cooling, then 400 mL of ethyl acetate and 400 mL of deionized water were added; the mixture was allowed to stand to form two separate layers, and the organic phase was washed with deionized water (100 mL×3) until the pH was about 7. To the organic phase was added saturated sodium bicarbonate aqueous solution (200 mL), after the mixture was allowed to stand to form two separate phases, the aqueous phase was extracted with ethyl acetate (100 mL×3), and the organic phase was discarded. To the sodium bicarbonate aqueous phase was added 200 mL of ethyl acetate, and then 1 M potassium hydrogen sulfate was slowly added to neutralize to pH=4; after standing to separate phases, the aqueous phase was extracted with ethyl acetate (200 mL×3); the organic phases were combined, dried over anhydrous sodium sulfate, filtered, and concentrated under reduced pressure to obtain compound 22-1. MS m/z: 438 $[M-971]^+$. $^1H$ NMR (400 MHz, $CDCl_3$) δ 8.64-8.91 (m, 2 H), 7.51-7.61 (m, 1 H), 7.45 (s, 1 H), 7.28-7.3(m, 1 H), 6.82 (br s, 3 H), 6.29 (s, 1 H), 5.84 (br s, 2 H), 1.96-2.04 (m, 1 H), 0.94-1.06 (m, 4 H).

Step 3: Synthesis of Compound 22

Starting compound 22-2 (0.6 g, 1.03 mmol), acetone (10 mL), and deionized water (1 mL) were added to a reaction flask, then tris(hydroxymethyl)aminomethane (249.58 mg, 2.06 mmol) was added, and the reaction mixture was stirred at 25° C. for 16 hours. The reaction mixture was filtered, and the filter cake was transferred to a flask, and concentrated under vacuum to remove residual solvent to obtain compound 22. $^1$H NMR (400 MHz, $D_2O$) δ: 8.75 (br s, 1 H), 8.44 (br s, 1 H), 7.19-7.36 (m, 2 H), 7.13 (br s, 1 H), 6.82 (br s, 2 H), 6.07 (s, 1 H). 5.65 (br s, 2 H), 3.65 (s, 12 H), 1.87 (br d, J=4.4 Hz, 1 H), 0.88 (br d, J=7.2 Hz, 2 H), 0.74 (br d, J=3.2 Hz, 2 H), MS m/z: 438[M+H−98]$^+$, 536[M+H]$^+$.

Embodiment 20: Preparation of Compound 23

23

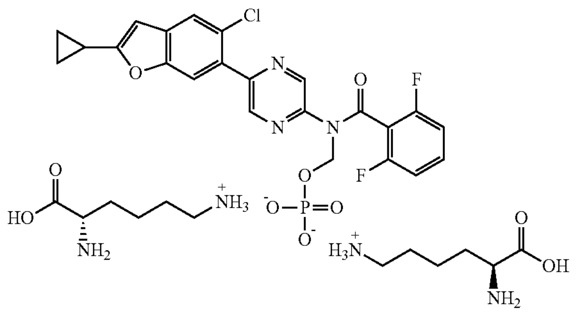

Synthetic Route:

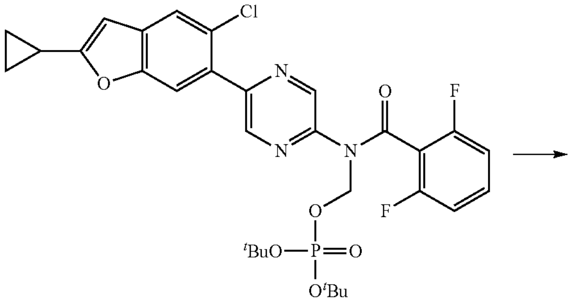

18-2

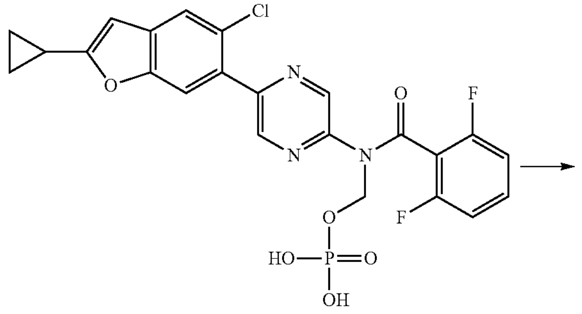

22-1

-continued

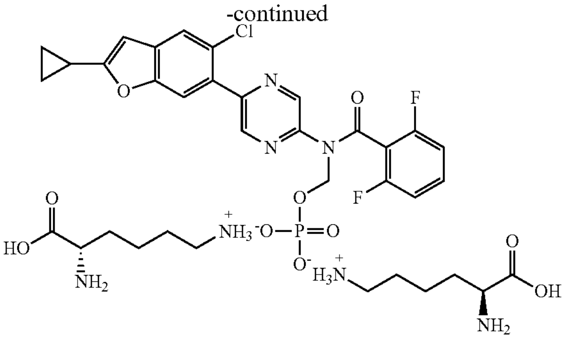

23

Step 1: Synthesis of Compound 22-1

Compound 18-2 (2.0 g, 3.09 mmol) and acetonitrile (10 mL) were added to a reaction flask, then a buffer solution of disodium hydrogen phosphate and citric acid (pH=3, 10 mL) were added, and the reaction mixture was stirred at 50° C. for 16 hours. The reaction mixture was filtered after cooling, then 400 mL of ethyl acetate and 400 mL of deionized water were added; the mixture was allowed to stand to form two separate layers, and the organic phases was washed with deionized water (100 mL×3) until the pH was about 7. To the organic phase was added saturated sodium bicarbonate aqueous solution (200 mL); after the mixture was allowed to stand to form two separate layers, the aqueous phase was extracted with ethyl acetate (100 mL×3), and the organic phase was discarded. To the sodium bicarbonate aqueous phase was added 200 mL of ethyl acetate, and then 1 M potassium hydrogen sulfate was slowly added to neutralize to pH=4; after the mixture was allowed to stand to form two separate layers, the aqueous phase was extracted with ethyl acetate (200 mL×3); the organic phases were combined, dried over anhydrous sodium sulfate, filtered, and concentrated under reduced pressure to obtain compound 22-1. MS m/z: 438 [M−97]$^+$. $^1$H NMR (400 MHz, $CDCl_3$) δ 8.64-8.91 (m, 2 H), 7.51-7.61 (m, 1 H), 7.45 (s, 1 H), 7.28-7.3(m, 1 H), 6.82 (br s, 3 H), 6.29 (s, 1 H), 5.84 s, 2 H), 1.96-2.04 (m, 1 H), 0.94-1.06 (m, 4 H).

Step 2: Synthesis of Compound 23

Substrate L-lysine (95.13 mg, 579.34 μmol) was dissolved in ethanol (0.2 mL) and deionized water (0.2 mL), then substrate 22-1 (206.95 mg, 289.67 μmol, 75% purity) was mixed well with ethanol (0.18 mL) and added to the reaction system. The reaction mixture was stirred at 25° C. for 16 hours. The reaction mixture was filtered, and the filter cake was transferred to a flask, and concentrated under vacuum to remove residual solvent to obtain compound 23. $^1$H NMR (400 MHz, $D_2O$) δ ppm 8.68-8.76 (m, 1 H), 8.49-8.60 (m, 1 H), 7.43-7.49 (m, 1 H), 7.38 (br s, 2 H), 6.80-7.00 (m, 2 H), 6.28-6.40 (m, 1 H), 5.50-5.67 (m, 2 H), 3.64-3.70 (m, 2 H), 2.94 (br t, J=7.28 Hz, 4 H), 1.95-2.05 (m, 1 H), 1.78-1.85 (m, 4 H), 1.60-1.67 (m, 4 H), 1.34-1.46 (m, 4 H), 0.93-1.01 (m, 2 H), 0.82-0.91 (m, 2 H). MS m/z: 438[M+H−98]$^+$, 536[M+H]$^+$.

Bioassay Data:

Experimental Embodiment 1: CRAC In Vitro Cell Activity Test of Compounds of the Present Disclosure 1. Experimental Materials 1.1 Reagents and Consumables:

| | Names of Reagents and Consumables | Brand | Article Number |
|---|---|---|---|
| 1 | 384-well transparent bottom black microplate | Corning | 3712 |
| 2 | 384-well flat bottom transparent microplate | Greiner | 781201 |
| 3 | 384-well pointed bottom transparent microplate | Corning | 3656 |
| 4 | Cell culture dish 10 cm | Corning | 430167 |
| 5 | Centrifuge tube 15 mL | Corning | 430791 |
| 6 | 1.5 mL transparent tube | Axegen | MCT-150-C |
| 7 | Fluo-8 Calcium flux assay reagent | Abeam | Ab112129 |
| 8 | HEPES | Gibco | 15630-080 |
| 9 | Probenecid | Thermo | P36400 |
| 10 | Sodium chloride | Sinopharm Group | 10019318 |
| 11 | Potassium chloride | Sinopharm Group | 10016318 |
| 12 | Sodium bicarbonate | Sinopharm Group | 10018390 |
| 13 | Magnesium chloride hexahydrate | Sinopharm Group | 1001218 |
| 14 | Calcium chloride | Sinopharm Group | 10005861 |
| 15 | Sodium hydroxide | Sinopharm Group | 10019718 |
| 16 | Glucose | Sigma | 101185414 |
| 17 | EGTA | Amresco | 732 |
| 18 | MEME cell culture fluid | Gibco | 61100 |
| 19 | FBS serum | Biosera | FB-1058/500 |
| 20 | DPBS | Invitrogen | 14190 |
| 21 | 0.25% Trypsin-EDTA | Invitrogen | 25200 |
| 22 | DMSO | Sigma | D5879 |
| 23 | Penicillin/streptomycin | Biosera | 70013 |

1.2 Apparatus:

| | Apparatus | Brand |
|---|---|---|
| 1 | Bravo Pipetting Workstation | Agilent |
| 2 | Echo 550 Liquid Workstation | Labcyte |
| 3 | FLIPR Assay Platform | MD |
| 4 | Cell Incubator | Thermo |
| 5 | Table-type high-speed centrifuge | Eppendorf |

1.3 Cell Strain: RBL-2H3, Derived from the HDB Cell Bank.

2. Experimental Procedure and Method:

2.1 Cell Plating

1) Preparing a biosafety cabinet and preheating relevant reagents. Cells were observed daily and passaged until 85% area of the 10 cm culture dish was covered with cells.
2) The cell culture dish was taken out and the culture medium was removed. The cell surface was washed with DPBS, and DPBS was then removed. The cells were digested with 1 mL of 0.25% Trypsin-EDTA for 1-3 minutes, and digestion was stopped by adding 2 mL of culture medium. A pipetting gun was used to gently blow cells until the cells fall off the surface of the culture dish.
3) The cell density was adjusted to 15000 cells per well using growth culture medium in a volume of 25 μL culture medium per well.
4) The cell culture plates were incubated to 80% density in an incubator at 37° C. and 5% $CO_2$.

2.2 Detection

1) The cell culture plates were removed from the incubator, centrifuged upside down at RPM 300 rpm for 30 seconds to remove the culture medium, and 20 μL of buffer (ultrapure water, 40 mM sodium chloride, 100 mM potassium chloride, 17 mM sodium bicarbonate, 0.1 mM ethylene glycol bisaminoethyl ether tetraacetic acid (EGTA), 12 mM glucose, 1 mM magnesium chloride, 5 mM hydroxyethyl piperazine ethylsulfuric acid (Hepes), 2.5 mM probenecid, 2 μM Fluo8) was added to each well, and placed in the incubator for 30 minutes.
2) Compound plates were prepared. Compounds were dissolved in DMSO, and prepared in compound plates (Greiner784201) using an Echo 550 according to the concentration to be tested, and dissolved in buffer without calcium ions (ultrapure water, 40 mM NaCl, 100 mM KCl, 17 mM $NaHCO_3$, 12 mM glucose, 1 mM $MgCl_2$, 5 mM cell culture medium, conclusion: the compounds of the present disclosure have significant inhibitory effect on KDM5A, 4 μM thapsigargin), 10 μL of compound was added to the cell culture plate using the FLIPR, and the cells were incubated for 20 minutes at room temperature.
3) An induction buffer containing calcium ions (4 mM $CaCl_2$, 40 mM NaCl, 100 mM KCl, 17 mM $NaHCO_3$, 12 mM glucose, 1 mM $MgCl_2$, 5 mM Hepes) was prepared, then 10 μL of the induction buffer was added to the cell culture plate using the FLIPR, and a calcium flux signal was collected for 260 seconds.

Data Processing: the collected signal results were analyzed and graphed using ScreenWorks, Excel, Xlfit. and GraphPad. Experiment results are shown in Table 1.

TABLE 1

RBL-3H cell assay $IC_{50}$ test results for inhibition of $Ca^{2+}$ by FLIPR assay

| Test Compounds | $IC_{50}$ (nM) |
|---|---|
| Compound 2 | 257 |
| Compound 3 | 78 |
| Compound 4 | 84 |
| Compound 5 | 351 |
| Compound 6 | 136 |
| Compound 11 | 38 |
| Compound 12 | 46 |
| Compound 9 | 30 |
| Compound 10 | 223 |
| Compound 13 | 124 |
| Compound 14 | 283 |
| Compound 15 | 273 |
| Compound 16 | 684 |
| Compound 17 | 230 |
| Compound 19 | 150 |

Conclusion: the compounds of the present disclosure have significant inhibitory effect on CRAC channel.

Experimental Embodiment 2: Pharmacokinetic Evaluation Experiment in Mice

Purpose of the experiment: male C57BL/6 mice were used as test animals, and the plasma drug concentrations of the test compounds were determined by LC/MS/MS at different time points after intravenous or intraperitoneal injection. The pharmacokinetic behavior of the test compound in mice was studied to evaluate its pharmacokinetic characteristics.

Drug preparation: an appropriate amount of sample was weighed to prepare 0.3 mg/mL or 0.5 mg/mL clear solution with 40% PEG400+20% Solutol+40% $H_2O$ (volume ratio).

Administration scheme: two healthy male C57BL/6 mice purchased from Beijing Vital River Laboratory Animal Technology Co., Ltd. was on a normal diet. The intravenous injection group was administered with 0.5 mg/mL solution, with a dose volume of 2 mL/kg and a dose of 1 mg/kg. The intraperitoneal injection group was administered with 0.3 mg/mL solution, with a volume of 10 mL/kg and a dose of 3 mg/kg.

Procedure: after animal administration, 25 μL of blood was collected at 0.083, 0.25, 0.5, 1, 2, 4, 8, 12, and 24 hours, respectively and placed in a commercial anticoagulative tube pre-loaded with EDTA-K2. The tubes were centrifuged for 10 minutes to separate plasma and stored at −60° C. The content of target compound in plasma samples was determined by LC/MS/MS.

Experimental results:

TABLE 2

Pharmacokinetic parameters of compound 6 in mice

| Groups | | Compound 6 |
|---|---|---|
| Intravenous injection group | $Vd_{ss}$ (L/kg) | 1.77 |
| | CL (mL/min/kg) | 2.05 |
| | $T_{1/2}$ (h) | 10.6 |
| | $AUC_{0-last}$ (nM · h) | 15570 |
| Intraperitoneal injection group | $C_{max}$ (nM) | 5530 |
| | $T_{max}$ (h) | 2.0 |
| | $AUC_{0-last}$ (nM · h) | 62744 |
| | F% | 125% |

Test conclusion: in the mice pharmacokinetic evaluation experiment, compound 6 administered via intravenous and intraperitoneal routes has higher plasma exposure and desirable pharmacokinetic properties.

Experimental Embodiment 3: Pharmacokinetic Evaluation in Mice

Purpose of the experiment: male C57BL/6 mice were used as test animals, and the LC/MS/MS method was applied to determine the plasma drug concentrations of the compounds at different time points after intravenous administration. The pharmacokinetic behavior of the compounds in mice was studied, and their pharmacokinetic characteristics were evaluated.

Drug preparation: an appropriate amount of sample was weighed to prepare 5 mg/mL of clear solution with sterile normal saline.

Administration scheme: two healthy male C57BL/6 mice purchased from Beijing Vital River Laboratory Animal Technology Co., Ltd. was on a normal diet, with a volume of 10 mL/kg and a dose of 50 mg/kg.

Procedure: after animal administration, 25 μL of blood was collected at 0.083, 0.25, 0.5, 1, 2, 4, 8, 12, and 24 hours, respectively and placed in a commercial anticoagulative tube pre-loaded with EDTA-K2. The tubes were centrifuged for 10 minutes to separate plasma and stored at −60° C. The content of the corresponding compounds in plasma samples was determined by LC/MS/MS.

Experimental results are shown in Table 3 and FIG. 1.

TABLE 3

Pharmacokinetic parameters of compound in mice

| | Compound 18, 50 mg/kg | | Compound 22, 50 mg/kg | |
|---|---|---|---|---|
| PK Parameters | Compound 18 | Compound 6 | Compound 22 | Compound 6 |
| $C_{max}$ (μM) | NA | 75.9 | NA | 42.2 |
| $T_{max}$ (h) | NA | 0.083 | NA | 0.04 |
| $T_{1/2}$ (h) | 2.49 | 18.1 | 2.53 | 45.9 |
| $Vd_{ss}$ (L/kg) | 0.84 | NA | 1.05 | NA |
| CL (mL/min/kg) | 25.1 | NA | 28.9 | NA |
| $AUC_{0-last}$ (μM · h) | 57.2 | 448 | 37.1 | 368 |
| $DNAUC_{0-last}$ (μM · h) | 0.69 | 5.42 | 0.58 | 5.72 |

Note:
NA represents the absence of this data, and DNAUC represents the exposure normalized to molar dose.

Experimental conclusion: in the mice pharmacokinetic evaluation experiment, compound 18 or 22 was rapidly eliminated in plasma after administration. At the same time, a large amount of compound 6 formation could be detected from 5 min of administration; at the same molar dose, the exposure of compound 6 in vivo was comparable as compound 18 or 22 after administration.

Experimental Embodiment 4: Thermodynamic Solubility Test

About 2 mg of test compound was weighed into a whatman vial, and 450 μL of phosphate buffer (50 mM, pH=7.4) was added. The stopper of whatman vial was pressed to near the liquid level so that the filter membrane in the stopper is in uniform contact with the liquid level. The vial was shaken well up and down on vortex for two minutes, and the dissolution of test compound in the whatman vial was recorded. The whatman vial was shaken in a shaker at ambient temperature for 24 hours at a rotational speed of 600 r/min. The stopper of whatman vial was slowly pressed to the lowermost part to obtain the supernatant. All compounds were checked to ensure there was no precipitate in the supernatant to prevent rupture of the filter membrane in the stopper. A linear solution (3 standard solutions, 1, 20, 200 μM, n=1) was prepared with diluent. The supernatant was taken out, and 10 μL of the supernatant was accurately taken out and diluted 100 times. The obtained diluent and stock solution and linear solution were simultaneously put into HPLC for detection and analysis, and the results were calculated by an external standard method according to peak area and dilution factor.

Experimental results are shown in Table 4:

TABLE 4

Solubility of compound of the present disclosure

| Compounds | Thermodynamic solubility (pH: 7.4) |
|---|---|
| Compound 18 | >200 mg/mL |
| Compound 21 | >200 mg/mL |
| Compound 22 | >200 mg/mL |
| Compound 23 | >200 mg/mL |

Conclusion: the solubility of compounds 18, 21, 22, 23 in the present disclosure in water is very good.

Experimental Embodiment 5: Inhibitory Activity of Compounds on Cytokines

1 Experimental Materials 1.1 Cell

Human peripheral blood mononuclear cells (hPBMC); supplier: HemaCare; Article Number: PB009C-2

1.2 Reagents

| Name | Supplier | Article Number |
|---|---|---|
| Anti-human CD3 antibody | BioLegend | 317326 |
| Anti-human C283 antibody | BioLegend | 302934 |
| Human IL-2 Fiex Set | BD | 558270 |
| Human TNF Flex Set | BD | 558273 |
| CBA Human Soluble Protein Master Buffer Kit | BD | 558265 |

1.3 Experimental Apparatus

| Name | Brand | Model |
|---|---|---|
| Flow cytometer | BD | Canto |

2 Experimental Procedures 2.1 Coating Culture Plate 96-well plates were coated with 5 μg/mL anti-human CD3 antibody (in DPBS) at 50 mL/well overnight at 4° C.

2.2 Seeding Plate

PBMC were removed from liquid nitrogen and immediately placed in a 37° C. water bath for recovery. To a 15 mL centrifuge tube, 5 mL culture medium (RPMI1640 culture medium+10% fetal bovine serum+1% non-essential amino acids+1% penicillin streptomycin+0.05 mM β-mercaptoethanol) was added, and the cell suspension was pipetted to the centrifuge tube, and the mixture was centrifuged at 320 g for 5 minutes. The cells were resuspended with culture medium and counted, and the cell concentration was then adjusted to $5\times10^5$ cells/mL with the culture medium, To the cell suspension was added anti-human CD28 antibody (final concentration 2 μg/mL), and the mixture was inoculated into a 96-well plate at 200 μL/well.

2.3 Drugs Incubation

Compounds were prepared at the desired concentration and added to the cells. The mixture was incubated at 37° C., 5% $CO_2$ for 2 days.

2.4 Determination of the Content of IL-2 and TNFα in the Supernatant of Cultured Cells by CBA Method The standards were prepared according to the instructions of IL-2 and TNFα Flex Set kit. The supernatant of the cultured cells was diluted 5-fold with the buffer provided in the kit and added to a 96-well plate together with the standards. The plated was added with magnetic beads containing antibody from the kit, and incubated at room temperature for 1 hour. The fluorescein PE-labeled secondary antibody in the kit was added and incubated at room temperature for 2 hours. The average fluorescence intensity of the PE channel was detected by flow cytometry. Based on the average fluorescence intensity of the standards, the contents of IL-2 and TNF-α of the samples were calculated.

Results are shown in Table 5:

TABLE 5

Inhibition of cytokines by compounds of the present disclosure

| Cytokines | Compound 4 | Compound 6 | Compound 13 | Compound 17 |
|---|---|---|---|---|
| IL-2 $IC_{50}$ (nM) | 280 | 63.8 | 201 | 173 |
| TNF-α $IC_{50}$ (nM) | ND | 138 | 303 | 328 |

Conclusion: the compounds of the present disclosure have a strong inhibitory effect on the release of the inflammatory cytokines IL-2 and TNF-α, which is important for alleviating the fatal systemic inflammation caused by acute pancreatitis.

Experimental Embodiment 6: Pharmacodynamic Test of Bombesin-Induced Acute Pancreatitis in Mice Purpose of the experiment: male C57BL/6 mice were used as test animals, and acute pancreatitis was induced by intraperitoneal injection of bombesin. The efficacy of compound 6 on acute pancreatitis was studied.

Drug preparation: an appropriate amount of sample was weighed, and compound 6 was prepared to a 4 mg/mL clear solution with 40% PEG-400+20% Solutol+40%+$H_2O$ (v/v).

Experiment scheme: healthy male C57BL/6 mice were injected with bombesin intraperitoneally to induce pancreatitis model, at a dose of 50 μg/kg each time, with 7 injections at an interval of 1 hour. One hour after the seventh injection of bombesin, serum was taken and the levels of amylase and lipase were measured. Compound 6 was administered by intraperitoneal injection at a dose of 20 mg/kg.

Figure 2:
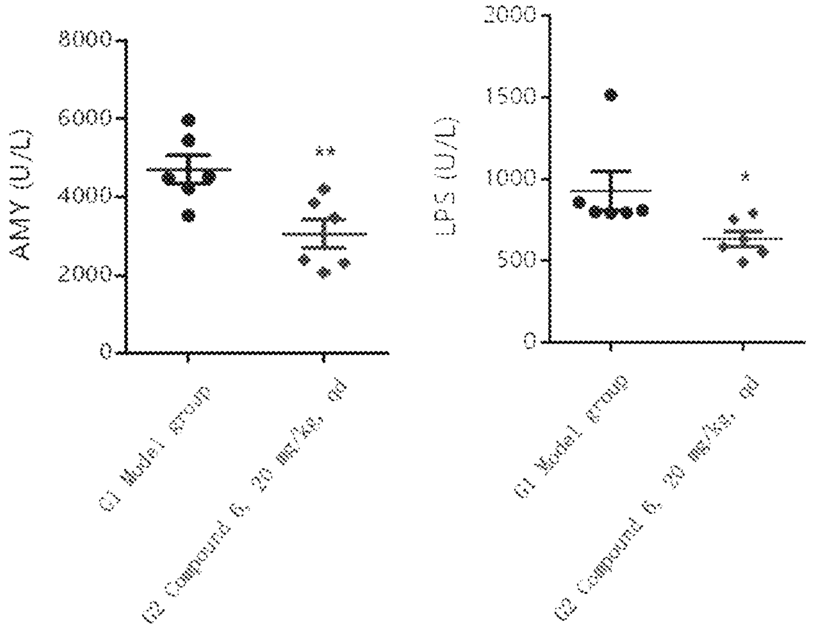
FIG. 2 shows test results for serum amylase (AMY) and serum lipase (LPS) levels of compound 6.

Experimental results: see FIG. 2. The levels of plasma amylase (AMY) and lipase (LPS) were analyzed by one-way ANOVA, * * indicates significant difference with G1 ($P<0.01$), * indicates significant difference with G1 ($P<0.05$).

Test conclusion: in the bombesin-induced acute pancreatitis model in mice. compound 6 is able to significantly reduce the levels of serum amylase (AMY) and lipase (LPS), indicating its ability to significantly improve the typical symptoms of acute pancreatitis and showing potential for the treatment of acute pancreatitis.

Experimental Embodiment 7: Pharmacodynamic Test of Bombesin-Induced Acute Pancreatitis in Mice Purpose of the experiment: male C57BL/6 mice were used as test animals, and acute pancreatitis was induced by intraperitoneal injection of bombesin. The efficacy of compound 22 on acute pancreatitis was studied.

Drug preparation: an appropriate amount of sample was weighed, and compound 22 was prepared to a 5 mg/mL clear solution with sterile normal saline.

Figure 3:
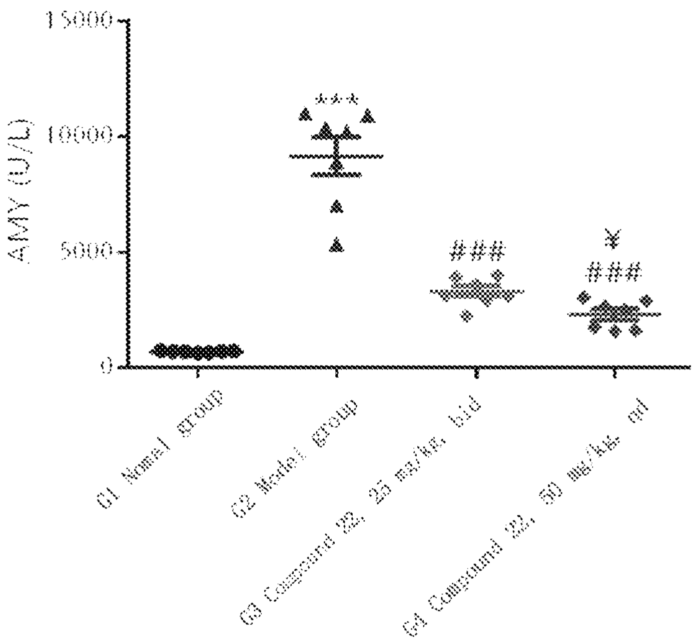
FIG. 3 shows test results for serum amylase (AMY) level of compound 22.
Figure 4:
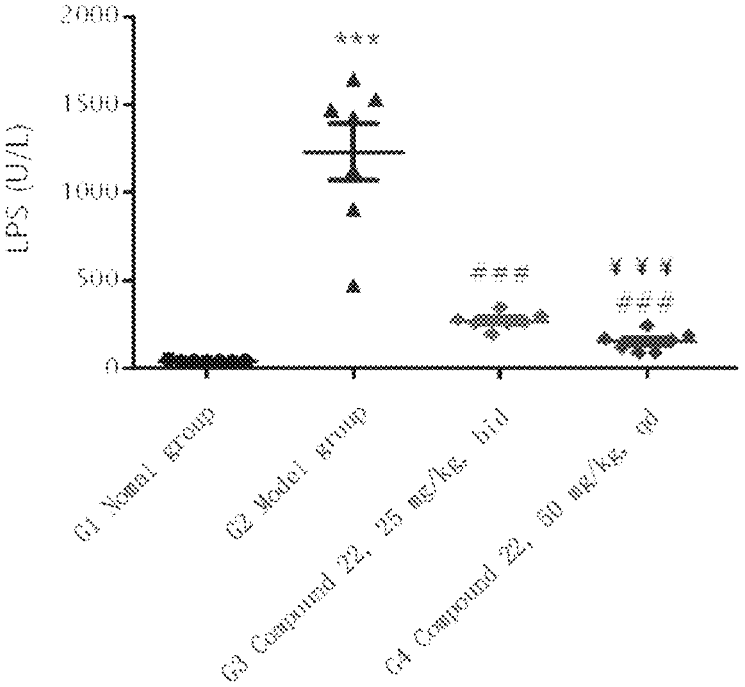
FIG. 4 shows test results for serum lipase (LPS) levels of compound 22.

Experiment scheme: healthy male C57BL/6 mice were injected with bombesin intraperitoneally to induce pancreatitis model, at a dose of 50 μg/kg each time, with 7 injections at an interval of 1 hour. One hour after the seventh injection of bombesin, serum was taken and the levels of amylase and lipase were measured. Compound 22 was administered intravenously in a total of 4 groups (G1-G4). G1 was the healthy group G2 was the model group, and G3-4 was the treatment group. G1-3 was given a first dose of drug or vehicle 0.5 h before the time point of the first injection of bombesin and a second dose of drug or vehicle 0.5 h after the fourth injection of bombesin. G4 was administered 0.5 h before the first injection of bombesin, without the second administration Experimental results: see FIG. 3. Plasma amylase (AMY) level was analyzed by one-way ANOVA, * * * indicates significant difference with G1 ($P<0.001$); # # # indicates significant difference with G2 ($P<0.001$); ¥ indicates significant difference with G3 ($p<0.05$). See FIG. 4, plasma lipase (LPS) level was analyzed by one-way ANOVA, * * * indicates significant difference with G1 ($P<0.001$); # # # indicates significant difference with G2 ($P<0.001$); ¥ ¥ ¥ indicates significant difference with G3 ($p<0.001$).

Test conclusion: in a bombesin-induced acute pancreatitis model in mice, compound 22 is able to reduce the levels of serum amylase (AMY) and lipase (LPS) very significantly, indicating its ability to significantly improve the typical symptoms of acute pancreatitis, showing excellent potential for the treatment of acute pancreatitis.

What is claimed is:

1. A compound represented by formula (VII), an isomer thereof or a pharmaceutically acceptable salt thereof, (VII)

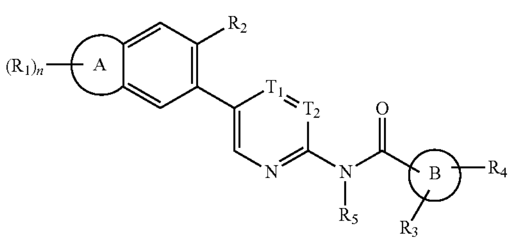

wherein, each of $T_1$ and $T_2$ is independently selected from CH and N;

$R_1$ is cyclopropyl, and each of the cyclopropyl is independently optionally substituted with 1, 2, or 3 $R_a$;

$R_2$ is selected from H, F, CI, Br, I and $C_{1-3}$ alkyl, and the $C_{1-3}$ alkyl is optionally substituted with 1, 2, or 3 $R_b$;

$R_3$ is selected from H, F, CI, Br, I, CN and $C_{1-3}$ alkyl, and the $C_{1-3}$ alkyl is optionally substituted with 1, 2, or 3 $R_c$;

$R_4$ is selected from H, F, CI, Br, I, CN and $C_{1-3}$ alkyl, and the $C_{1-3}$ alkyl is optionally substituted with 1, 2, or 3 $R_d$;

$R_5$ is selected from H,

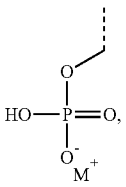 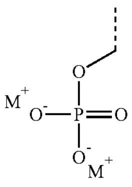 and 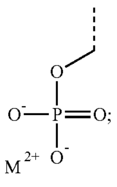

each of $M^+$ is independently selected from $Na^+$, $NH_4^+$, $K^+$, choline,

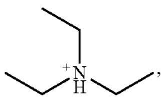 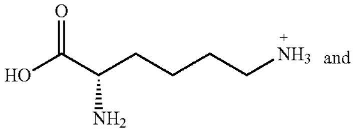 and

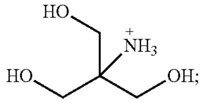

each of $M^{2+}$ is independently selected from $Ca^{2+}$, $Mg^{2+}$, $Zn^{2+}$ and

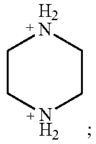

ring A is selected from 5- to 6-membered heteroaryl;

ring B is selected from phenyl, 5-to 6-membered heteroaryl, $C_{3-6}$ cycloalkyl and 4- to 6-membered heterocycloalkyl;

n is 1;

each of $R_a$, $R_b$, $R_c$ and $R_d$ is independently selected from F, CI, Br, I, OH, $NH_2$ and $C_{1-3}$ alkyl, and the $C_{1-3}$ alkyl is optionally substituted with 1, 2, or 3 R;

each of R is independently selected from F, CI, Br and I;

each of the 5-to 10-membered heteroaryl, 5- to 6-membered heteroaryl and 3-to 10- membered heterocycloalkyl independently contains 1, 2, or 3 heteroatoms or heteroatom groups independently selected from —O—, —NH—, —S— and N.

2. The compound represented by formula (VII) according to claim 1, the isomer thereof or the pharmaceutically acceptable salt thereof, wherein, each of $R_a$, $R_b$, $R_c$ and $R_d$ is independently selected from F, CI, Br, I, $CH_3$, $CF_3$, $CHF_2$, $CH_2F$, $CH_2CH_3$, $CH_2CF_3$, $CH_2CH_2CH_3$,

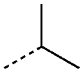 and 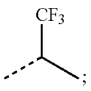

or, $R_5$ is selected from H,

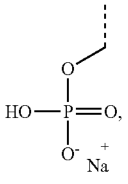 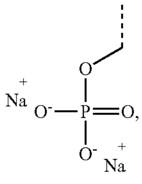 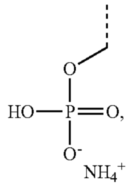 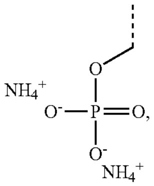

-continued

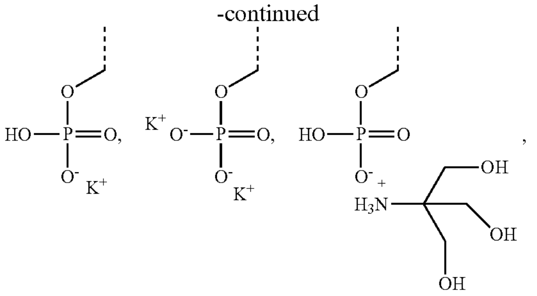

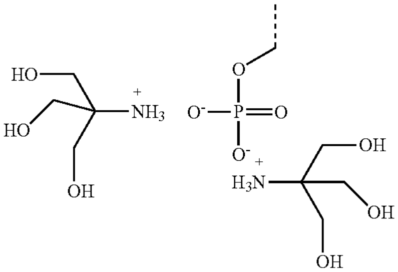

and

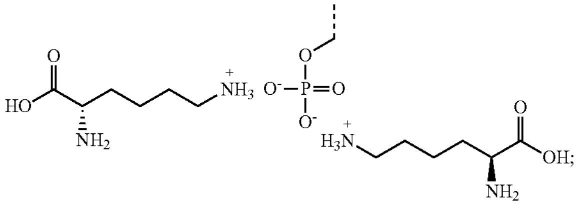

or, ring A is selected from oxazolyl, isoxazolyl, furanyl, pyridinyl and 1,2,3-triazolyl.

3. The compound represented by formula (VII) according to claim 1, the isomer thereof or the pharmaceutically acceptable salt thereof, wherein, R2 is selected from H, F, CI, Br, I, $CH_3$, $CF_3$, $CHF_2$, $CH_2F$, $CH_2CH_3$, $CH_2CF_3$, $CH_2CH_2CH_3$,

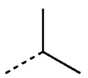

and

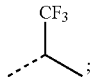

;

or, $R_3$ is selected from H, F, CI, Br, I, CN, $CH_3$, $CF_3$, $CHF_2$, $CH_2F$, $CH_2CH_3$, $CH_2CF_3$, $CH_2CH_2CH_3$,

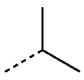

and

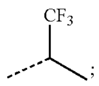

;

or, $R_4$ is selected from H, F, CI, Br, I, CN, $CH_3$, $CF_3$, $CHF_2$, $CH_2F$, $CH_2CH_3$, $CH_2CF_3$, $CH_2CH_2CH_3$,

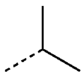

and

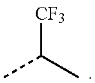

.

4. The compound represented by formula (VII) according to claim 3, the isomer thereof or the pharmaceutically acceptable salt thereof, wherein, $R_2$ is selected from CI;

or, $R_2$ is selected from H, F, $CH_3$ and CN;

or, $R_4$ is selected from H, F, $CH_3$ and CN.

5. The compound represented by formula (VII) according to claim 1, the isomer thereof or the pharmaceutically acceptable salt thereof, wherein, the structural unit

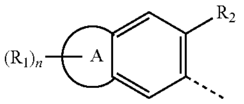

is selected from

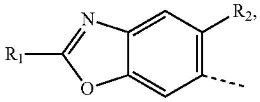

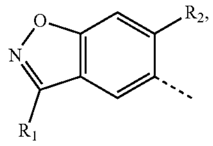

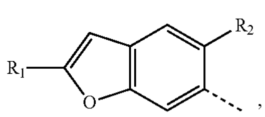

,

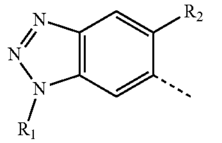

and

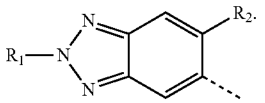

6. The compound represented by formula (VII) according to claim 5, the isomer thereof or the pharmaceutically acceptable salt thereof, wherein, structural unit

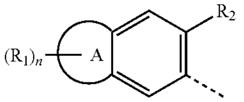

is selected from

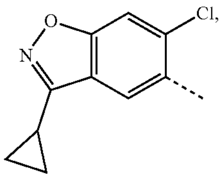

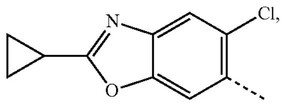

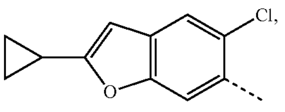

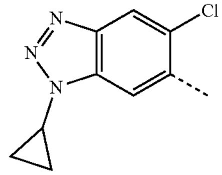

and

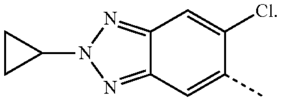

7. The compound represented by formula (VII) according to claim 1, the isomer thereof or the pharmaceutically acceptable salt thereof, wherein, ring B is selected from phenyl,

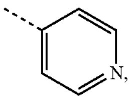
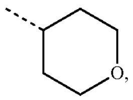
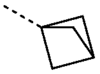
and
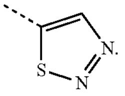

8. The compound represented by formula (VII) according to claim 7, the isomer thereof or the pharmaceutically acceptable salt thereof, wherein, the structural unit

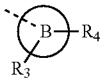

is selected from

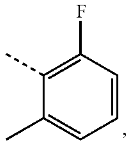
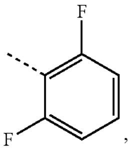
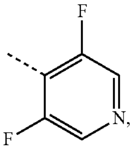
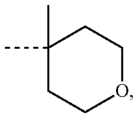
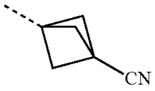
and
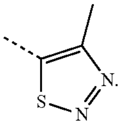

9. The compound represented by formula (VII) according to claim 1, the isomer thereof or the pharmaceutically acceptable salt thereof, and the compound is selected from:

(I-1)

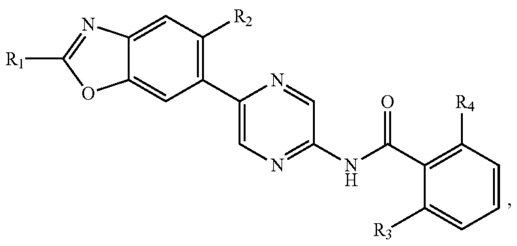

(I-2)

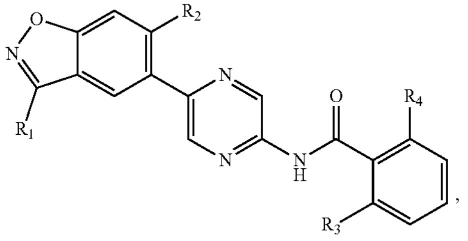

-continued (I-3)

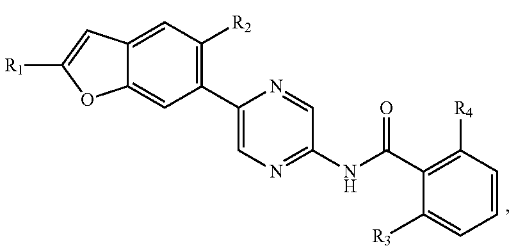

(II-2)

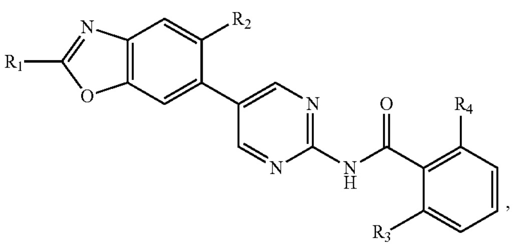

(II-3)

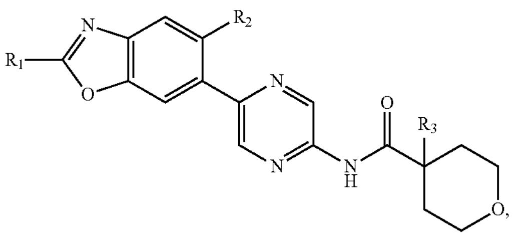

(II-4)

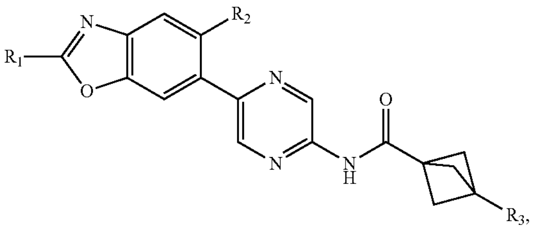

(III-1)

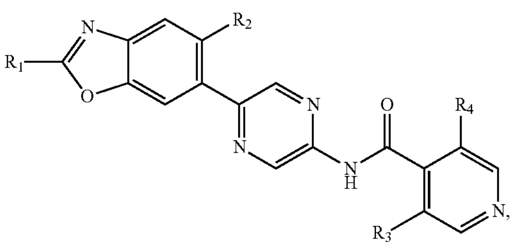

(V-1)

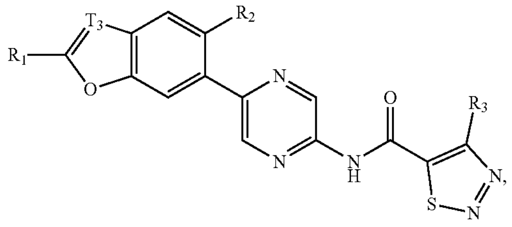

-continued
(VI-1)
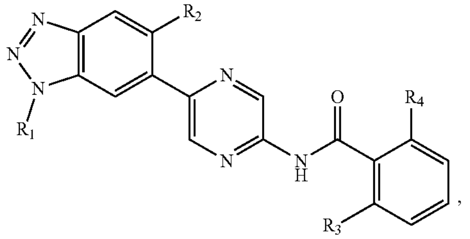
(VII-1)
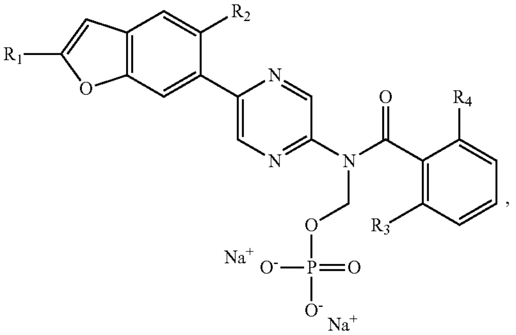
(VIII-1)
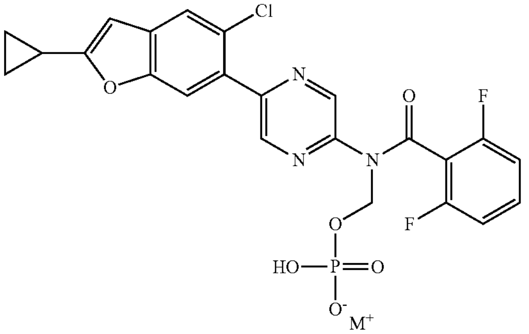
and
(VIII-2)
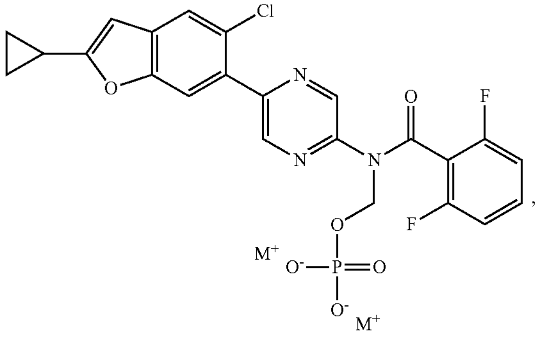
wherein,
$T_3$ is selected from CH and N;
$R_1$, $R_2$, $R_3$, $R_4$ and $M^+$ are defined as above.
10. The compound represented by following formula (VII) according to claim 1, the isomer thereof or a pharmaceutically acceptable salt thereof, wherein, the compound is selected from
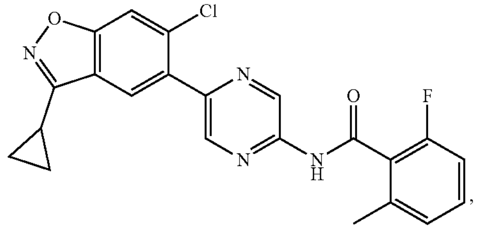
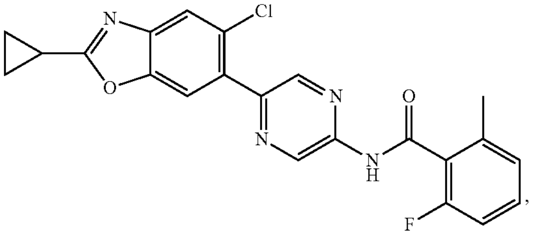
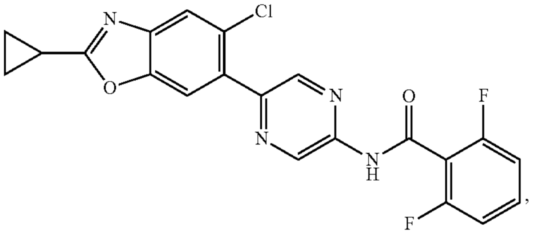
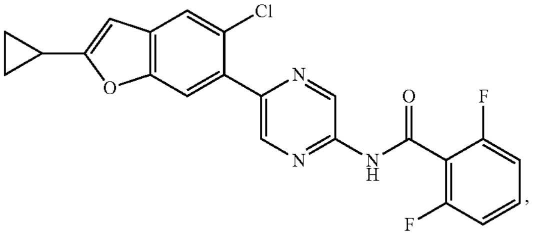
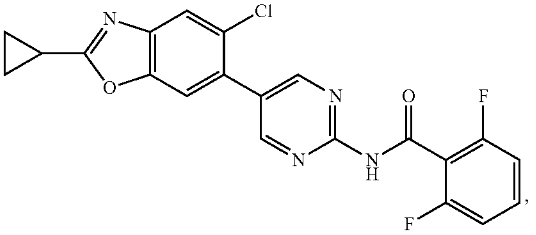
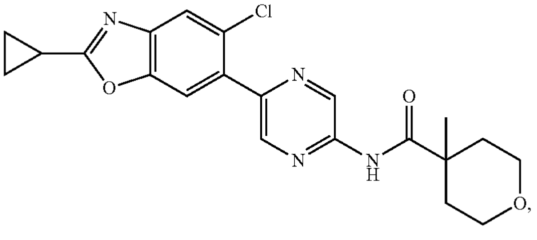
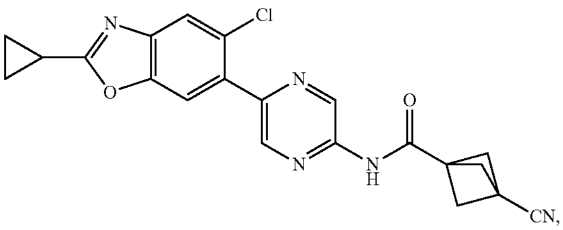

-continued
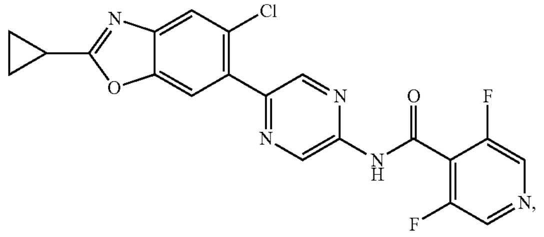
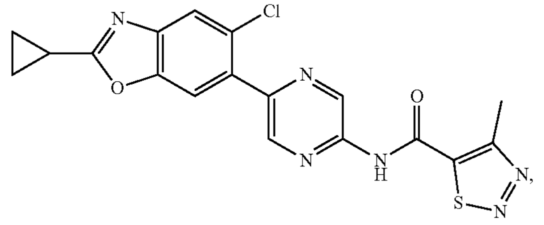
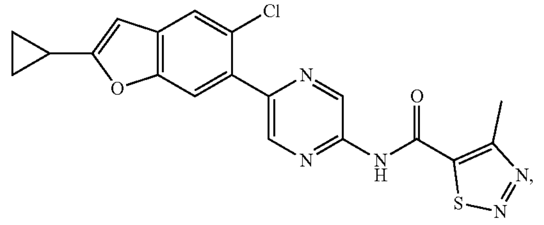
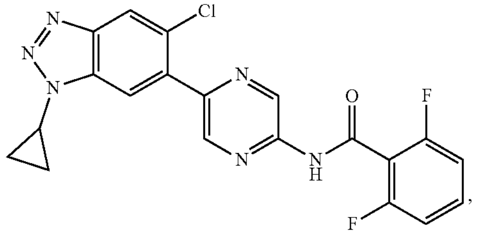
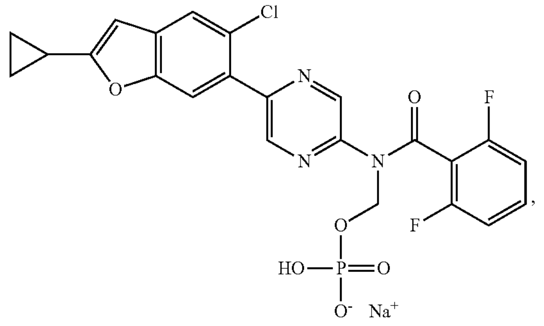
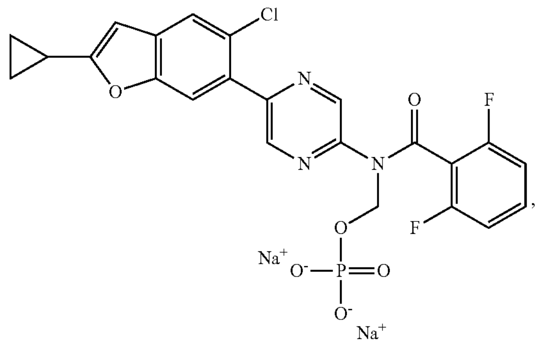
-continued
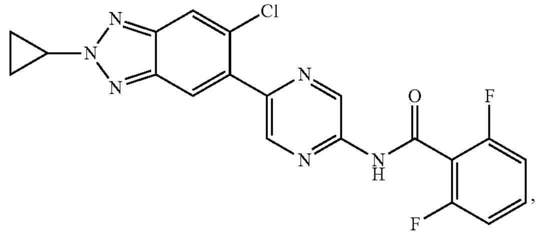
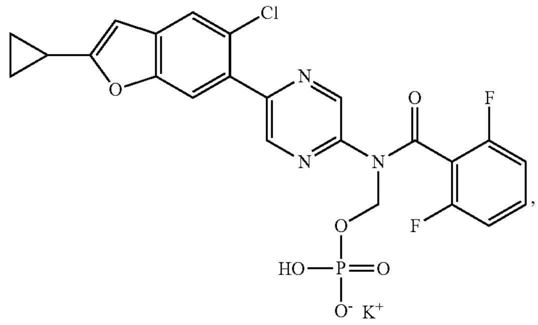
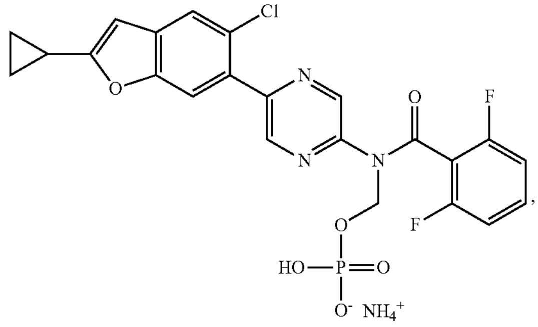
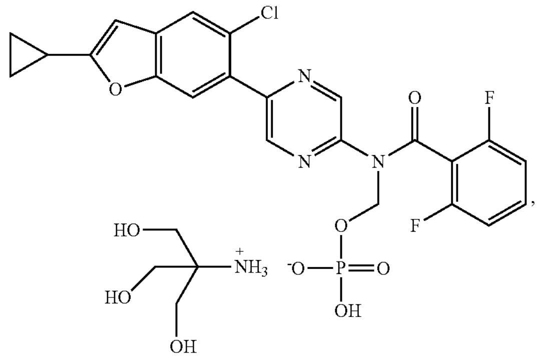
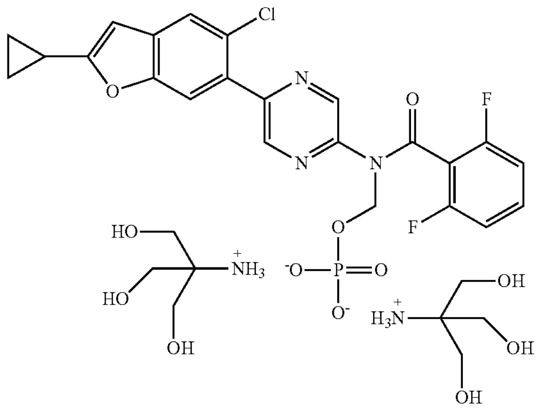
and -continued

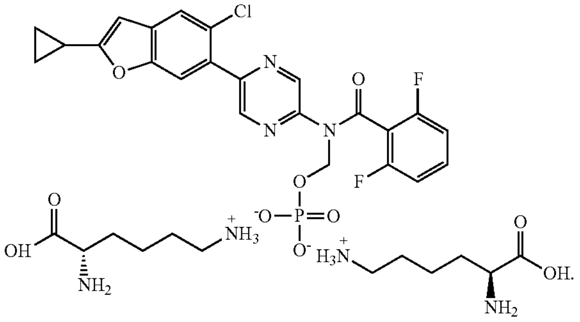

11. A pharmaceutical composition comprising a therapeutically effective amount of the compound according to claim 1, the isomer thereof or the pharmaceutically acceptable salt thereof as an active ingredient and a pharmaceutically acceptable carrier.

12. The compound represented by formula (VII) according to claim 1, the isomer thereof or the pharmaceutically acceptable salt thereof, wherein, $R_2$ is selected from H, F, CI, Br, I and $C_{1-3}$ alkyl.

13. The compound represented by formula (VII) according to claim 1, the isomer thereof or the pharmaceutically acceptable salt thereof, wherein, $R_2$ is selected from H, F, CI, Br, and I.

14. The compound represented by formula (VII) according to claim 1, the isomer thereof or the pharmaceutically acceptable salt thereof, wherein, $R_2$ is selected from F, CI, Br, and I.

15. A method for inhibiting CRAC in a subject in need thereof, comprising administering an effective amount of the compound according to claim 1, the isomer thereof or the pharmaceutically acceptable salt thereof to the subject.

16. A method for treating acute pancreatitis in a subject in need thereof, comprising administering an effective amount of the compound according to claim 1, the isomer thereof or the pharmaceutically acceptable salt thereof to the subject.

* * * * *